US007919257B2

(12) United States Patent
Hoogenboom et al.

(10) Patent No.: US 7,919,257 B2

(45) Date of Patent: *Apr. 5, 2011

(54) METHOD FOR SELECTING A SINGLE CELL EXPRESSING A HETEROGENEOUS COMBINATION OF ANTIBODIES

(75) Inventors: Hendricus Renerus Jacobus Mattheus Hoogenboom, Maastricht (NL); Ton Logtenberg, Driebergen (NL)

(73) Assignee: Merus Biopharmaceuticals, B.V.i.o., Werkhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 11/292,414

(22) Filed: Nov. 30, 2005

(65) Prior Publication Data

US 2006/0160184 A1 Jul. 20, 2006

Related U.S. Application Data

(63) Continuation of application No. PCT/NL2004/000386, filed on May 28, 2004.

(30) Foreign Application Priority Data

May 30, 2003 (EP) .................................... 03076671

(51) Int. Cl.

| | |
|---|---|
| ***G01N 33/53*** | (2006.01) |
| ***C12P 21/04*** | (2006.01) |
| ***C07K 16/00*** | (2006.01) |
| ***A61K 39/00*** | (2006.01) |
| ***C12N 5/07*** | (2006.01) |
| ***C12P 21/08*** | (2010.01) |
| *A01N 25/00* | (2006.01) |

(52) U.S. Cl. ..... 435/7.1; 435/70.1; 435/328; 530/387.1; 530/387.3; 530/388.1; 530/389.1; 424/136.1; 436/547

(58) Field of Classification Search ........................ None
See application file for complete search history.

(56) References Cited

U.S. PATENT DOCUMENTS

| | | | |
|---|---|---|---|
| 4,399,216 | A | 8/1983 | Axel et al. |
| 4,599,311 | A | 7/1986 | Kawasaki |
| 4,634,665 | A | 1/1987 | Axel et al. |
| 4,801,687 | A | 1/1989 | Ngo |
| 4,816,567 | A | 3/1989 | Cabilly et al. |
| 4,868,103 | A | 9/1989 | Stavrianopoulos et al. |
| 4,937,190 | A | 6/1990 | Palmenberg et al. |
| 5,137,809 | A | 8/1992 | Loken et al. |
| 5,151,504 | A | 9/1992 | Croze |
| 5,179,017 | A | 1/1993 | Axel et al. |
| 5,223,409 | A | 6/1993 | Ladner et al. |
| 5,627,037 | A | 5/1997 | Ward et al. |
| 5,631,169 | A | 5/1997 | Lakowicz et al. |
| 5,641,640 | A | 6/1997 | Hanning |
| 5,667,988 | A | 9/1997 | Barbas et al. |
| 5,733,779 | A | 3/1998 | Reff |
| 5,772,997 | A | 6/1998 | Hudziak et al. |
| 5,783,186 | A | 7/1998 | Arakawa et al. |
| 5,789,208 | A | 8/1998 | Sharon |
| 5,888,789 | A | 3/1999 | Rodriguez |
| 5,965,371 | A | 10/1999 | Marasco et al. |
| 6,004,940 | A | 12/1999 | Marasco et al. |
| 6,080,560 | A | 6/2000 | Russell et al. |
| 6,180,357 | B1 | 1/2001 | Young et al. |
| 6,207,446 | B1 | 3/2001 | Szostak et al. |
| 6,265,150 | B1 | 7/2001 | Terstappen et al. |
| 6,291,740 | B1 | 9/2001 | Bremel et al. |
| 6,303,341 | B1 | 10/2001 | Hiatt et al. |
| 6,335,163 | B1 | 1/2002 | Sharon |
| 7,067,284 | B1 | 6/2006 | Barbas et al. |
| 7,262,028 | B2 * | 8/2007 | Van Berkel et al. ......... 435/69.6 |
| 7,429,486 | B2 | 9/2008 | Van Berkel et al. |
| 2003/0039958 | A1 | 2/2003 | Holt et al. |
| 2003/0091561 | A1 | 5/2003 | van de Winkel et al. |
| 2003/0194403 | A1 | 10/2003 | van de Winkel et al. |
| 2003/0207346 | A1 | 11/2003 | Arathoon et al. |
| 2003/0224408 | A1 | 12/2003 | Hoogenboom et al. |
| 2007/0054362 | A1 | 3/2007 | Van Berkel et al. |
| 2007/0059766 | A1 | 3/2007 | Logtenberg et al. |
| 2009/0263864 | A1 | 10/2009 | Van Berkel et al. |

FOREIGN PATENT DOCUMENTS

| | | |
|---|---|---|
| CA | 2 405 961 | 11/2001 |
| CA | 1 341 364 | 6/2002 |
| CA | 2 445 255 | 10/2002 |
| CA | 2 114 353 | 1/2006 |
| EP | 0120694 | 10/1984 |
| EP | 0314161 | 5/1989 |
| EP | 0402029 | 12/1990 |
| EP | 0445625 | 9/1991 |
| EP | 0481790 | 4/1992 |
| EP | 0523949 | 1/1993 |

(Continued)

OTHER PUBLICATIONS

Hoogenboom et al., Antibody phage display technology and its applications, 1998, Immunotechnology, vol. 4, pp. 1-20.* Kwaks et al., Identification of anti-repressor elements that confer high and stable protein production in mammalian cells, 2003, Nature Biotechnology, vol. 21, pp. 553-558.*

Krebs et al., High-throughput generation and engineering of recombinant human antibodies, 2001, Journal of Immunological Methods, vol. 254, pp. 67-84.*

(Continued)

*Primary Examiner* — Bo Peng
*Assistant Examiner* — Benjamin P Blumel
(74) *Attorney, Agent, or Firm* — TraskBritt

(57) ABSTRACT

The present invention provides combinations of specific binding proteins, such as immunoglobulins, that are designed to be true combinations, essentially all components of the combination being functional and compatible with each other. The invention further provides a method for producing a composition comprising at least two different proteinaceous molecules comprising paired variable regions, the at least two proteinaceous molecules having different binding specificities, comprising paired variable regions, at least two proteinaceous molecules having different binding specificities, comprising contacting at least three different variable regions under conditions allowing for pairing of variable regions and harvesting essentially all proteinaceous molecules having binding specificities resulting from the pairing.

13 Claims, 25 Drawing Sheets

FOREIGN PATENT DOCUMENTS

| | | |
|---|---|---|
| EP | 0724639 | 1/2001 |
| EP | 1 325 932 B1 | 4/2005 |
| FR | 2 817 875 | 6/2002 |
| WO | 9002809 | 3/1990 |
| WO | 9108216 | 6/1991 |
| WO | 9117271 | 11/1991 |
| WO | 9201047 | 1/1992 |
| WO | 9209690 | 6/1992 |
| WO | 9215679 | 9/1992 |
| WO | 9218619 | 10/1992 |
| WO | 9220791 | 11/1992 |
| WO | 9301288 | 1/1993 |
| WO | 9402610 | 2/1994 |
| WO | 9425591 | 11/1994 |
| WO | 9517085 | 6/1995 |
| WO | 9517500 | 6/1995 |
| WO | 9520401 | 8/1995 |
| WO | 9627011 | 9/1996 |
| WO | 9742313 | 11/1997 |
| WO | 9747739 | 12/1997 |
| WO | 9815627 | 4/1998 |
| WO | 9815833 | 4/1998 |
| WO | 9839416 | 9/1998 |
| WO | 9841645 | 9/1998 |
| WO | 9850431 | 11/1998 |
| WO | 9920749 | 4/1999 |
| WO | 9923221 | 5/1999 |
| WO | 9936569 | 7/1999 |
| WO | 9964582 | 12/1999 |
| WO | 0063403 | 10/2000 |
| WO | 0070023 | 11/2000 |
| WO | 0071694 | 11/2000 |
| WO | 0119394 | 3/2001 |
| WO | 0127279 | 4/2001 |
| WO | 0132901 | 5/2001 |
| WO | 0148485 | 7/2001 |
| WO | 0164929 | 9/2001 |
| WO | WO 01/88132 A2 | 11/2001 |
| WO | 0218948 | 3/2002 |
| WO | WO 02/46233 A1 | 6/2002 |
| WO | 02074969 | 9/2002 |
| WO | 02096948 | 12/2002 |
| WO | 03004704 | 1/2003 |
| WO | WO 03/016501 A2 | 2/2003 |
| WO | 03048306 | 6/2003 |
| WO | WO 03/102157 A2 | 12/2003 |
| WO | 2004106375 | 12/2004 |
| WO | WO 2004/106375 A1 | 12/2004 |
| WO | 2005068622 | 7/2005 |

OTHER PUBLICATIONS

Norderhaug et al., Balanced expression of single subunits in a multisubunit proteins, achieved by cell fusion of individual transfectants, 2002, European Journal of Biochemistry, vol. 269, pp. 3205-3210.*

Huse et al., Purification of antibodies by affinity chromatography, 2002, Journal of Biochemical and Biophysical Methods, vol. 51, pp. 217-231.*

Burioni et al., Nonneutralizing Human Antibody Fragments against Hepatitis C Virus E2 Glycoprotein Modulate Neutralization of Binding Activity of Human Recombinant Fabs, Abstract, Virology, Sep. 2001, pp. 245, vol. 288, No. 1.

Lu et al., Selection of high affinity human neutralizing antibodies to VEGFR2 from a large antibody phage display library for antiangiogenesis therapy, Abstract, International Journal of Cancer, Jan. 20, 2002, pp. 39399, vol. 97, No. 3.

Sidhu et al., Phage-displayed antibody libraries of synthetic heavy chain complementarity determining regions, Abstract, Journal of Molecular Biology, Apr. 23, 2004, pp. 299310, vol. 338, No. 2.

Kang et al., Linkage of recognition and replication functions by assembling combinatorial antibody Fab libraries along phage surfaces, Proc. Natl. Acad. Sci., May 1991, pp. 4363-4366, vol. 88.

PCT International Search Report, PCT/NL2004/000386 dated Nov. 23, 2004.

U.S. Appl. No. 11/490,545, filed Jul. 20, 2006, Logtenberg et al., Mixture of Binding Proteins.

U.S. Appl. No. 11/593,280, filed Nov. 6, 2006, Van Berkel et al., Recombinant Production of Mixtures of Antibodies.

U.S. Appl. No. 11/977,954, filed Oct. 26, 2007, Houtzager et al., Chimaeric Phages.

U.S. Appl. No. 12/221,021, filed Jul. 29, 2008, Van Berkel et al., Recombinant Production of Mixtures of Antibodies.

Heintges et al., Cloning, Bacterial Expression and Sequencing of Human Antibody Fragments Against Hepatitis C Virus NS3 by Phage Display of a Combinatorial Phagemid Library, Hepatology, p. 497, vol. 28, No. 4, 1998.

Boel et al., Functional human monoclonal antibodies of all isotypes constructed from phage display library-derived single-chain Fv antibody fragments, Journal of Immunological Methods, 2000, pp. 153-166, vol. 239.

De Kruif et al., Rapid selection of cell subpopulation-specific human monoclonal antibodies from a synthetic phage antibody library, Proc. Natl. Acad. Sci., USA, Apr. 1995, pp. 3938-3942, vol. 92.

de Kruif et al., Selection and Application of Human Single Chain Fv Antibody Fragments from a Semi-synthetic Phage Antibody Display Library with Designed CDR3 Regions, Journal of Molecular Biology, 1995, pp. 97-105, vol. 248.

Figini et al., In Vitro Assembly of Repertoires of Antibody Chains on the Surface of Phage by Renaturation, Journal of Molecular Biology, 1994, pp. 68-78, vol. 239.

Franconi et al., Functional expression in bacteria and plants of an scFv antibody fragment against tospoviruses, Immunotechnology, 1999, pp. 189-201, vol. 4.

French, et al., Cancer Research, 1991, pp. 2353-2361, vol. 51.

Holliger et al., "Diabodies": Small bivalent and bispecific antibody fragments, Proc. Natl. Acad. Sci., Jul. 1993, pp. 6444-6448, vol. 90.

Lekkerkerker, Phage antibodies against human dendritic cell subpopulations obtained by flow cytometry-based selection on freshly isolated cells, Journal of Immunological Methods, 1999, pp. 53-63, vol. 231.

Kortt et al., Abstract, Dimeric and trimeric antibodies: high avidity scFvs for cancer targeting, Biomol. Eng., Oct. 15, 2001, pp. 95-108, vol. 18, No. 3.

Lindhofer et al., Preferential Species-Restricted Heavy/Light Chain Pairing in Rat/Mouse Quadromas, Journal of Immunology, 1995, pp. 219-225, vol. 155.

Ma et al., Assembly of monoclonal antibodies with IgG1 and IgA heavy chain domains in transgenic tobacco plants, Eur. J. Immunol., 1994, p. 131-138, vol. 24.

Merchant et al., An efficient route to human bispecific IgG, Nature Biotechnology, Jul. 1998, pp. 677-681, vol. 16.

Morrison, Sherie L., Transfectomas Provide Novel Chimeric Antibodies, Science, Sep. 20, 1985, pp. 1202-1207, vol. 229.

Muyldermans, Reviews in Molecular Biotechnology, 2001, pp. 277-302, vol. 72.

Pau et al, The human cell line PER.C6 provides a new manufacturing system for the production of influenza vaccines, Vaccine, 2001, pp. 2716-2712, vol. 19.

PCT International Preliminary Examination Report, PCT/EP03/07690, dated Nov. 11, 2004.

PCT International Search Report, PCT/EP03/07690, dated Apr. 16, 2004.

PCT International Search Report, PCT/NL2005/000036, dated Jan. 19, 2005.

Schmitz et al., Phage Display: A Molecular Tool for the Generation of Antibodies—A Review, Placenta, 2000, pp. S106-S112, Supplement A, Trophoblast Research, vol. 14.

Sugita, et al., Int. J. Cancer, 1986, pp. 351-357, vol. 37.

Vaughan et al., Human Antibodies with Sub-nanomolar Affinities Isolated from a Large Non-immunized Phage Display Library, Nature Biotechnology, Mar. 1996, pp. 309-314, vol. 14.

Ward et al., Nature, 1989, pp. 544-546, vol. 341.

Warnaar et al., Hybridoma, 1994, pp. 519-526, vol. 13, No. 6.

Office Action for U.S. Appl. No. 11/593,280 dated Apr. 28, 2008.

Office Action for U.S. Appl. No. 11/593,280 dated Oct. 29, 2008.

Office Action for U.S. Appl. No. 11/593,280 dated Apr. 17, 2009.

Office Action for U.S. Appl. No. 11/593,280 dated Dec. 11, 2009.

Notice of Allowance for U.S. Appl. No. 11/593,280 dated Apr. 6, 2010.

Office Action for U.S. Appl. No. 12/221,021 dated May 12, 2010.
Office Action for U.S. Appl. No. 11/490,545 dated Mar. 25, 2008.
Office Action for U.S. Appl. No. 11/490,545 dated Jul. 30, 2008.
Office Action for U.S. Appl. No. 11/490,545 dated May 29, 2009.
Office Action for U.S. Appl. No. 11/490,545 dated Jan. 13, 2010.
Friedenson et al., Immunoglobulin G Antibodies from an Individual Rabbit in Which Several Heavy Chain Variants Are Paired with One Light Chain Sequence, The Journal of Biological Chemistry, 1973, pp. 7073-7079, vol. 248, No. 20.

* cited by examiner pSCFV polylinker sequence

```
--pel B leader -----------  -- VH insertion ----------------------- ----linker--
 A   A   A   P   A   M   A   Q   V   Q   L   Q   V   T   V   S   S   G   G   G
GCG GCC CAG CCG GCC ATG GCA CAG GTC CAA CTG CAG GTC ACC GTC TCG AGT GGT GGA GGC
---SfiI------------                        --PstI-       --XhoI--
                 --NcoI---                        --BstNI-

----linker------------------------------------ --- VL insertion -------------
 G   S   G   G   G   G   S   G   G   G   G   S   D   I   E   L   T   E   I   K
GGT TCA GGC GGA GGT GGC TCT GGC GGT GGC GGA TCG GAT ATC GAG CTC ACT GAG ATC AAA
                                                -EcoRV- -SalI--

---         ---------------------- c-myc tag ---------
 R   A   A   A   E   Q   K   L   I   S   E   E   D   L   N   *  (SEQ ID NO: 47)
CGG GCG GCC GCA GAA CAA AAA CTC ATC TCA GAA GAG GAT CTG AAT TAA (SEQ ID NO: 46)
    ---NotI---
```

Enzyme sites :

```
SfiI  : GGCCNNNN/NGGCC (SEQ ID NO: 48)
NotI  : GC/GGCCGC      (SEQ ID NO: 49)
ApalI : GTGCA/C        (SEQ ID NO: 50)
XhoI  : C/TCGAG        (SEQ ID NO: 51)
SacI  : GAGCT/C        (SEQ ID NO: 52)
PstI  : CTGCA/G        (SEQ ID NO: 53)
NcoI  : C/CATGG        (SEQ ID NO: 54)
SalI  :GTCGAC          (SEQ ID NO: 55)
BstEII: GGTNACC        (SEQ ID NO: 56)
EcoRV : GAT/ATC        (SEQ ID NO: 57)
```

• The polylinker sequence of pSCFV, a pUC119-based plasmid suitable for stepwise cloning of antibody variable regions and expression of scFv fragments.

FIG. 13

Comparison of light chains of three hybridomas

| Clone | | CDR1 | | CDR2 | | CDR3 | |
|---|---|---|---|---|---|---|---|
| JA : | EIVLTQSPATLSLSPGERATLAC | RASQTASRYLA | WYQQKPGQAPRLLIY | DTSNRAT | GIPARFSGSGSGTDFTLSISSLEPEDFAVYYC | QQRFNWPWT | FGQGTKVEFKRT |
| JB : | SYVLTQPPSVSVAPGKTARINC | GGNNIEYRSVH | WYQQKSGQAPVAVIY | DNSDRPS | GIPERFSGSKSGNTATLTISRVEAGDEADYYC | QVWDISSDVV | FGGGTKLTVL |
| M57: | QSALTQPRSVSGSPGQSVTISC | TGTSSDIGGYNFVS | WYQQHPGKAPKLMIY | DATKRPS | GVPDRFSGSKSGNTASLTISGLQAEDEADYYC | CSYAGDYTPGVV | FGGGTKLTVL |

FIG. 16

Design of a hybrid light chain library for h4D5v8 and 2C4 :

```
                                                  CDR1                                CDR2
                                             24     30                                 53
                                             |      |                                  |
(SEQ ID NO: 61) h4D5: DIQMTQSPSSLSASVGDRVTITC RASQDVNTAVA WYQQKPGKAPKLLIY SASFLYS
(SEQ ID NO: 62) 2C4 : ----------------------- K-----SIG-- --------------- ---YR-T

(SEQ ID NO: 63) HYB1: ----------------------- X-----XXX-- --------------- ---XX-X
(SEQ ID NO: 64) HYB2: ----------------------- ------S---- --------------- ---XX-X

                                                        CDR3
                                                      91   95
                                                      |    |
h4D5: GVPSRFSGSRSGTDFTLTISSLQPEDFATYYCQQ HYTTPPT FGQGTKVEIKR
2C4 : ---------------------------------- Y-IY-Y- -----------

HYB1: ---------------------------------- X-XX-X- -----------
HYB2: ---------------------------------- F------ -----------
```

FIG. 23

METHOD FOR SELECTING A SINGLE CELL EXPRESSING A HETEROGENEOUS COMBINATION OF ANTIBODIES

CROSS-REFERENCE TO RELATED APPLICATIONS

This application is a continuation of PCT International Patent Application No. PCT/NL2004/000386, filed on May 28, 2004, designating the United States of America, and published in English, as PCT International Publication No. WO 2004/106375 A1 on Dec. 9, 2004, which application claims priority to European Patent Application No. 03076671.1 filed on May 30, 2003, the contents of the entirety of each of which is incorporated herein by this reference.

INCORPORATION-BY-REFERENCE OF MATERIAL SUBMITTED ON A COMPACT DISC

Pursuant to 37 C.F.R. §1.52(e)(5), the sequence listing has been submitted by CD-R, and is hereby incorporated by reference in its entirety. The CD-Rs are labeled "Copy 1" and "Copy 2", respectively, and each disc contains one file entitled "2183-7585us seq list.txt" which is 47 KB and was created on Mar. 24, 2006.

TECHNICAL FIELD

The present invention relates to the field of molecular biology, in particular, to medical molecular biology.

BACKGROUND

Specific recognition plays an important role in modern medical biology. Receptor-ligand interactions, immune responses, infections, enzymatic conversions are all based on specific recognition between molecules. Of particular interest are specific protein-protein interactions, which give a vast array of possibilities to interfere in all kinds of biological processes. Throughout nature, biological processes are found that depend on more than one (simultaneous) protein-interaction. At the present time, it seems that interfering at more than one point in a biological process is going to be more effective than a single interference. Particularly in antibody therapy, it is seen that one (monoclonal) antibody is often not effective enough for treating a particular disorder and/or disease. Therefore, the attention of many medical researchers is now focused on combination therapies. Well-known examples of combinations of antibodies that are presently clinically pursued are for the treatment of non-Hodgkin's lymphoma, the combination of the already approved anti-CD20 antibody Rituxan with the anti-CD22 antibody Epratuzumab from AmGen, and for the treatment of Hepatitis B, a combination of two human antibodies being developed by XTL Pharmaceuticals (E. Galun et al., *Hepatology* (2002) 35:673-679). However, the combination of multiple (two or more) drugs (be it antibodies or other) has a number of technical, practical and regulatory drawbacks. The drugs were typically not designed as combinations and development with optimal clinical efficacy and compatibility may be a problem. As an example, conditions for stabilizing the one may be detrimental to stability of the other(s). Furthermore, multiple sources of recombinant production lead to multiple sources of risks, such as, viral contamination, prion contamination and the like.

The present invention provides combinations of specific binding proteins, such as immunoglobulins, that are designed to be true combinations, essentially all components of the combination being functional and compatible with each other. By producing true combinations, the present inventors have opened up an avenue of further improvements in both the production and properties of the combinations. These improvements and their advantages will become apparent from the following description.

SUMMARY OF THE INVENTION

Thus, the invention provides a method for producing a composition comprising at least two different proteinaceous molecules comprising paired variable regions, the at least two proteinaceous molecules having different binding specificities, comprising contacting at least three different variable regions under conditions allowing for pairing of variable regions and harvesting essentially all proteinaceous molecules having binding specificities resulting from the pairing. Binding specificities are defined as interactions between molecules that can be distinguished from background interactions. Typically, specific interactions between molecules have higher binding affinity than background interactions between molecules.

Specific binding molecules, which for an important part are made up of amino acid residues (proteinaceous molecules), often require the pairing of different amino acid sequences in order to build a binding site. An amino acid sequence that pairs with another amino acid sequence to build a binding site is referred to as a variable region herein. Of course, such a sequence may be part of a larger amino acid sequence, which may again be part of a larger proteinaceous molecule, e.g., as a subunit. As an example, in an antibody a complementarity-determining region (CDR) may be a variable region, but a combination of three CDRs with their framework regions may also be considered as a variable region. According to the present invention, at least two different binding sites are built in one system, in one method. Thus, variable regions (amino acid sequences) are brought together under conditions in which they may pair to build two different binding sites. This requires at least three variable regions, of which one is capable of pairing with both other variable regions, thus building two specific binding sites. The two specific binding sites may be in one proteinaceous molecule or in different proteinaceous molecules, or both.

In antibodies of the IgG isotype, for example, this would be an antibody having two identical or two different binding sites. By producing the two desired binding specificities in one system, there is only one source of the products and thereby less risk of contamination with viruses, prions and the like. Such a system may be a cell-free system, such as a wheat germ system, but it is preferred to carry out methods according to the invention inside a cell, or more cells of the same origin, preferably the origin of the subjects to be treated, typically human. For production and selection purposes, other cells, such as, bacteria, insect cells, yeasts and other eukaryotes may typically be preferred.

If the pairing of the variable regions takes place in a cell, then it is preferred that the production of the variable regions also takes place in a cell, preferably the same cell. A particularly useful way of producing variable regions is through the expression of nucleic acids encoding these variable regions. It is preferred that all variable regions in one cell are produced by such expression, it is, however, also possible to produce a number of variable regions in this manner and have other variable regions brought in, based on different techniques of production, or the same means of production, but in another cell. For most purposes, the nature of the nucleic acid is not critical, it may be RNA, is preferably DNA, may be episomal or integrated, part of a viral vector or a plasmid, etc. However, for the final production system of the combination of proteins having different binding specificities, it is preferred that the nucleic acid or acids encoding the variable regions are stably integrated into the host genome. Production of variable regions through expression of nucleic acids encoding them gives the possibility to manipulate the encoding sequences, thereby enabling the designing of new binding specificities, better pairing properties, exchanging useful sequences from one encoding sequence to another and the like. It also gives the possibility for selection for improved or different binding and/or pairing properties after alterations have been made, giving rise to the creation of libraries of many different nucleic acids in systems with easy selection mechanisms.

In this manner, the number of variable regions to be expressed for obtaining different binding sites may be reduced. One may design and/or select for a so-called promiscuous variable region, which is capable of pairing with more than one different binding region. "Pairing" is defined herein as any kind of coming together to build a binding site, be it through covalent or noncovalent bonding, conformational arrangement, folding, dimerization, multimerization or any other way. It thus encompasses terms such as associating, assembling, binding, combining and the like, be it directly or indirectly. Particularly when more than two different binding specificities are made in one cell, it is useful to have promiscuous variable regions in such a system, reducing the number of different nucleic acids that have to be expressed. In such a system, the promiscuous variable region should not contribute significantly to the binding specificity of the paired regions. Preferably, it is mostly involved in folding and stability of the binding site, thereby, of course, indirectly influencing the binding specificity.

Apart from reducing the number of nucleic acids to be expressed, by choosing one or more promiscuous variable regions, the number of paired variable regions which are not functional can be reduced to essentially zero.

Particularly in the field of immunoglobulins, which typically comprise two pairs of two different paired variable regions, the production of more than one immunoglobulin inside the same cell often leads to pairing of variable regions that does not lead to a desired binding specificity. In the present invention, pairs are designed such that in one system essentially all variable regions can pair with another in the system to form a useful specific binding site. In methods of the prior art wherein four variable regions were expressed in hybrid-hybridomas or quadromas, the result was a low percentage of desired bispecific antibodies, a percentage of either original antibodies and a substantial percentage of paired regions without significant useful binding specificity. Bispecific antibodies may be produced with the methods according to the present invention, either together with or without the concomitant production of the original antibodies, but typically essentially without production of non-functional pairs. In addition, mixtures of multiple monoclonal and multiple bispecific antibodies may be produced with the methods according to the present invention.

The methods as disclosed in the detailed description provide for adaptation of the nucleic acids encoding variable regions to the desired end result. Using promiscuous pairing or the opposite, monogamous pairing, the end result can be designed. Where bispecific antibodies or other certain pairings are to be excluded, the use of pairs of variable regions that can pair only with each other is used. Further, methods as disclosed in the detailed description provide for adaptation of the nucleic acids encoding the constant regions to lead to a preferential pairing of the binding sites formed by the variable regions when attached to the constant regions.

Antibodies in the present invention are intended to refer to all variations of immunoglobulins that retain specific binding, such as Fabs, Fab'2, scFvs, but typical for antibodies according to the invention is the presence of a pair of amino acid sequences (at least two CDRs) that are paired to form a binding site. Thus, the invention also provides a method wherein the variable regions are derived from heavy chains and/or light chains of immunoglobulins, engineered versions of variable regions with elements of heavy and/or light, chains of immunoglobulins and/or a method wherein the proteinaceous molecules are antibodies, fragments and/or derivatives of antibodies.

The methods according to the invention are typically preferred for the production of multiple (i.e., three or more) binding specificities in one system. Because of the specific design of the contributing variable regions this has now become technically and commercially feasible.

Another element of the invention useful for control of the production is placing expression of different variable regions under control of different elements such as promoters, (trans) activators, enhancers, terminators, anti-repressors, repressors, and the like. These control elements may be inducible or repressible. Thus, the production of variable regions can be regulated, thus optimizing pairing conditions as desired. Different combinations of variable regions can be made by separation in time of expression of various variable regions and/or ratios between different paired variable regions may be manipulated by regulating expression levels. Variations are described in the detailed description. The invention also provides an expression system for carrying out a method according to the invention, comprising nucleic acids encoding variable regions together with all elements required for gene expression and pairing, preferably such an expression system comprises at least one recombinant cell, such as a bacterium, a yeast cell, a fungal cell, an insect cell, a plant cell or another eukaryotic cell, in particular, a mammalian cell, more in particular, a human cell.

Such a system can be provided with all necessary and useful control elements as disclosed herein before and as well known in the art. Selection elements and suicide elements may also be introduced into such a system as desired.

A collection of expression systems according to the invention comprising a variety of combinations of different specificities is also provided, typically as a library for use in selecting desired combinations of variable regions.

Such selection methods are also part of the present invention. Thus, the invention in one embodiment also provides a method for selecting combinations of proteinaceous molecules having specific affinity for at least two target epitopes, comprising contacting a collection according to the invention with the two target epitopes and selecting combinations showing the specific affinity.

Such methods are particularly useful when the two target epitopes are associated with one disease or disorder. It is preferred to combine such a method with subjecting a selected combination of proteinaceous molecules to a biological assay indicative of an effect of the combination on the disease and/or disorder.

Compositions obtainable by the methods of the invention are also part of the present invention. Preferred are compositions comprising at least three different paired variable regions, having different binding specificities, in particular, those wherein the variable regions are derived from immunoglobulin light chains and/or immunoglobulin heavy chains. A combination composition that targets both TNF-α as well as IL-1β is an exemplary combination of the invention. In such typical therapeutic uses it is important that the combination preparations do not lead to severe immune responses in the subject to be treated. At least some of the antigenic parts of the binding molecules, such as the constant regions in antibodies should be of human origin. In the alternative, antigenic parts may be omitted or masked by molecules such as PEG. Thus, the invention also provides in one embodiment a composition according to the invention, which is a pharmaceutical composition. Although antibodies have found use in other areas, and antibody combinations according to the present invention can be used in other areas, the pharmaceutical use of the invented combinations is preferred, both diagnostic and therapeutic, with a preference for the latter. However, in industrial applications the combinations of the invention may also be superior to existing separation techniques, because of ease of production, consistency of production and the availability of many combinations of specificities, capable of separating almost anything from any mixture. In testing, be it in pharmaceutical diagnostics or in any other field (environmental, agricultural, to name a few) the combinations of the invention can be used advantageously as well. Both partners of a sandwich assay can be made in one cell. Agglutination mixtures can be made in one cell. When using the IgG format, the expression in the same cell will lead to a substantial fraction of bispecific compounds, which offer unique applications in combination with the monoclonals present in the same mix. For example, when a monoclonal antibody can only bind with one arm to an antigen, a bispecific molecule with binding sites capable of binding to two different epitopes on the same antigen, may more consistently than the monoclonal antibody mixture immobilize or trap antigen. Again, ease and consistency of production, as well as the diversity of specificities is an asset of the combinations of the invention. These advantages of course also apply in selecting and producing combinations of specificities for therapeutic and/or prophylactic use, with additional advantages in ease of selection, efficacy of selected combinations and the mentioned safety aspects.

A simple combination according to the invention starts with two specificities present in the combination. When a promiscuous variable region is present, such a combination requires only three different variable regions. The combination can be made such that all resulting paired variable regions in one proteinaceous molecule have the same specificity, giving monospecific molecules, or the variable or, if appropriate, the constant regions can be designed such that bispecific molecules are also present. It can also be designed such that one monospecific and one bispecific molecule are present, but that the other possible monospecific molecule does not arise, because the variable regions cannot assemble in that manner. Thus, the invention in one embodiment comprises a composition comprising at least one monospecific antibody and at least one bispecific antibody produced in one cell for use as a pharmaceutical. In some applications bispecific molecules, especially antibodies, may be advantageous for bringing two antigens together on a cell surface. Such aggregation events are often required in biology for transduction of a signal to the inside of a cell. Bispecific antibodies in the mixture may also be used to connect effector molecules with target cells. The uses envisaged for bispecific antibodies in the prior art are also envisaged for bispecific molecules according to the invention. The most advantageous compositions according to the invention comprise more than two different monospecific binding molecules, optionally together with the different possible combinations of bispecific or multispecific molecules that may result from the different possible pairing events. These multispecific mixtures resemble polyclonal mixtures in their efficacy for recognizing antigens, but without the drawbacks of many irrelevant specificities in the mixture. The mixtures resemble monoclonal antibodies in their defined constitution, ease of production and high specificities, but without the concomitant loss of efficacy. The mixtures according to the invention are referred to as Oligoclonics™. Oligoclonics™ can thus contain two, three, or more different binding specificities, and can exist in various formats. In the simplest form, Oligoclonics™ in the IgG format contain a mixture of different monospecific antibodies and bispecific antibodies in a particular given ratio. In the Fab format, Oligoclonics™ contain a mixture of different Fab molecules which are the product of correctly paired variable regions. In the mixed format, Oligoclonics™ contain a mixture of antibodies and antibody fragments.

As disclosed herein, the methods and means of the invention in one embodiment are the production of combinations of specificities. Before production of combinations, suitable combinations must be designed and/or selected. These methods for designing and selection are also part of the present invention. Thus, in a further embodiment, the invention provides a method for producing nucleic acids encoding variable regions for use in a method for production of combinations of specificities according to the invention comprising synthesizing nucleic acids encoding variable regions, expressing the nucleic acids and allowing the expression products to pair and selecting nucleic acids encoding variable regions having desired pairing behavior.

In an alternative embodiment, the invention provides a method for producing nucleic acids encoding variable regions for use in a method for production of combinations of specificities according to the invention comprising altering existing nucleic acids encoding variable regions, expressing the nucleic acids and allowing the expression products to pair and selecting nucleic acids encoding variable regions having desired pairing behavior. Of course, both methods may be combined and/or repeated in any order. Synthesis, alteration and selection methods are disclosed in more detail in the detailed description.

Preferred nucleic acids (also part of the invention) for use in producing combinations of specificities are those encoding immunoglobulin polypeptides. Of course all types of immunoglobulins, especially antibodies (IgM, IgE, IgGs, etc.) but also fragments (scFv, Fab, single-domain, engineered variants) can be used in the present invention. Variable regions can, for example, be derived from either immunoglobulin heavy chain variable regions, or immunoglobulin light chain variable regions, but can also be engineered hybrids of heavy and light chain variable regions (with, for example, swapped CDR regions or FR regions). Variable regions can, for example, be obtained from hybridomas, by cloning from immune or non-immune donors or can be synthetically constructed variable regions. Even hybrids can be produced using nucleic acids and methods of the invention. For example, hybrids with different yet functional binding sites can be made by providing elements from different isotypes, for example, IgM and IgG, or IgM and IgA. It should be born in mind that T cell receptors, resemble antibodies in many respects. Thus, the methods according to the invention can also be applied advantageously with T cell receptors, their variable regions and their encoding nucleic acids. It is thus preferred that the invention is carried out using immunoglobulins having different chains (T cell receptors), especially antibodies having light chains and/or heavy chains or parts/derivatives thereof. Of course part and/or derivatives according to this invention are such parts and/or derivatives that do have specific binding properties comparable to immunoglobulins.

This means that variable regions according to the invention should at least comprise an element which resembles a complementarity-determining region of an antibody (CDR). Preferably it should have more than a CDR, preferably a variable region resembles in size and physicochemical properties a VH or VL of an antibody. The detailed description describes the invention using antibodies as an exemplary embodiment of the invention.

The invention will be described in more detail in the following detailed description.

BRIEF DESCRIPTION OF THE DRAWINGS

FIG. 13: The sequence of pSCFV (SEQ ID NO:46), a pUC119-based plasmid suitable for stepwise cloning of antibody variable regions and expression of scFv fragments.

FIG. 16: Sequence alignment of the three light chains amino acid sequences of antibodies JA (Kappa) (SEQ ID NO:8), and JB (SEQ ID NO:10) and M57 (SEQ ID NO:12) (both lambdas). The position of the CDRs is indicated.

FIG. 23: Design of a hybrid light chain library for identifying a pairing-compatible light chain for h4D5v8 and 2C4. The amino acid sequences used by Herceptin (trastuzumab, h4D5v8) and pertuzumab (Omnitarg, 2C4) are compared to one another, and to two designer light chain libraries, HYB1 and HYB2 (see Example 17 for details of the design). Residues identical to those of Herceptin are indicated with a dash; amino acids are encoded by the single-letter consensus; X means positions to be targeted for diversification in a library approach. Numbers indicated for the most relevant residue positions (see text for more details).

DETAILED DESCRIPTION OF THE INVENTION

Figure 1:
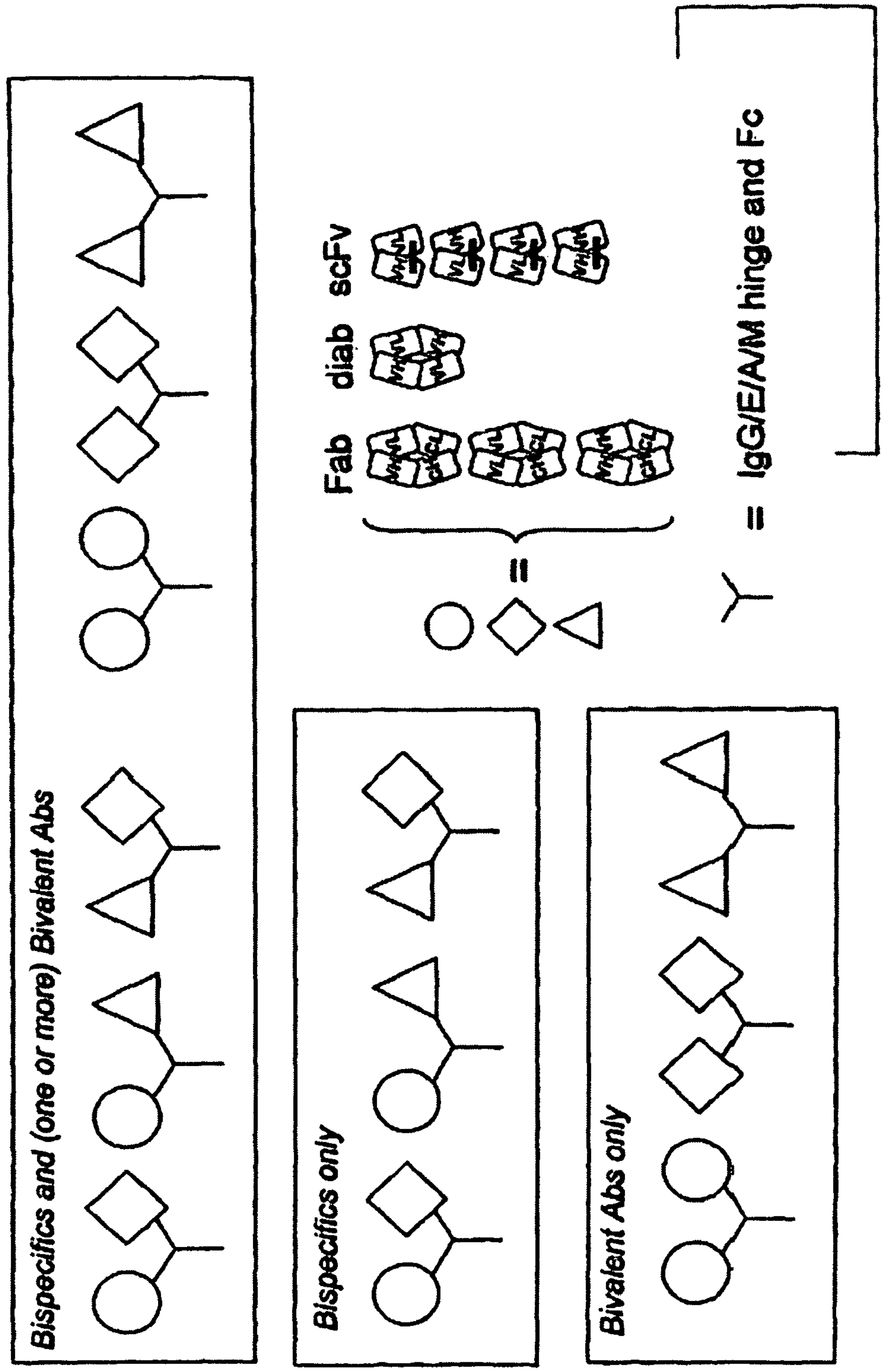
FIG. 1: Examples of composition of three or six proteinaceous molecules with three different binding specificities. The use of antibodies with appropriate pairing between the variable regions yields mixtures of antibodies that are bispecific or monospecific and bivalent (top panel). By appropriate engineering to manipulate the pairing between the variable regions, mixtures of only bispecifics or bivalent molecules arise (left hand side panels). In the legend on the right panel (grey box) it is indicated that the three symbols, the circle, triangle and square, represent binding sites consisting each of variable regions.

In the fight against infection, the immune system creates a cellular and humoral response that can specifically combat the infectious agent. The humoral immune response is based on immunoglobulins, or antibodies, which contact antigens and mediate certain effector functions to clear the infection ((I. M. Roit, et al. (1985)) and all references herein). In the immune system antibodies are generated by B-lymphocytes. Antibodies consist of heavy and light chains that are assembled via inter-domain pairing and interchain disulphide bonds to form multivalent molecules. Various isotypes of natural antibodies exist, including IgG (within humans, four subclasses, IgG1, IgG2, IgG3, IgG4), IgM, IgD, IgA and IgE. An IgG molecule contains two heavy (H) and two light (L) chains, both with a variable (V) and constant (C) regions. A typical IgG antibody comprises two heavy (H) chain variable regions (abbreviated herein as VH), and two light (L) chain variable regions (abbreviated herein as VL). The VH and VL regions can be further subdivided into regions of hypervariability, termed "complementarity-determining regions" ("CDR"), interspersed with regions that are more conserved, termed "framework regions" (FR). The extent of the framework region and CDRs has been precisely defined (see, E. A. Kabat, et al. (1991) *Sequences of Proteins of Immunological Interest, Fifth Edition*, U.S. Department of Health and Human Services, NIH Publication No. 91-3242, and C. Chothia, et al. (1987) *J. Mol. Biol.* 196:901-917, which are incorporated herein by reference).

In the generation of the primary immune response, the pairing of heavy and light variable region sequences of antibodies is a random process. The variable region genes are first assembled by recombining of a set randomly picked V. (D) and J genetic elements represented in the genome as a diverse gene pool. The recombined heavy and light variable regions are then spliced towards their respective constant region genes and the chains expressed, assembled and secreted as immunoglobulin. In this combinatorial library, in principle every heavy chain can pair with every light chain, to create a vast repertoire of different antigen specificities, with diversity derived from the rearrangement process (which also introduces further diversity at some of the segment junctions) and from the combinatorial assembly of the heavy and light chain variable regions. In principle, B-cells produce only one antibody specificity, encoded by one antibody heavy and one antibody light chain sequence. The immune system selects via an efficient antigen-selection process those antibodies that can bind to a given antigen, in particular, when the antigen is foreign and part of a pathogen.

In natural immunoglobulins, the light chain which consists of two domains, is paired to the heavy chain, which consists of at least four domains and a hinge region: non-covalent interactions occur between VH and VL, and between CH1 and CL; between the latter a disulphide bridge provides a covalent linkage between heavy and light chains. Furthermore, the heavy chains are found paired to one another, i.e., in the IgG format, and sometimes further associate with additional elements such as J-chains (i.e., in the IgM format). A strong non-covalent interaction occurs between the CL and CH1 domains, a frequently weaker interaction is present between VL and VH. The heavy chains are paired via interactions in the hinge region (often covalently associated via one or more disulphide bridges) and between the CH2 and CH3 domains. By sequencing large pools of antibody variable genes from isolated B-cell and comparing the frequency of the pairings of VH and VL segments, it was confirmed that this pairing between VH and VL regions is on average a random process. However, since the variable regions are genetically diverse and some of this diversity at the amino acid level is structurally situated at the predicted interface region between the two domains, the pairing of one given VH to another VL is not any more random. For example, pairing of a given VH with another VL than the molecule was initially selected with, may lead to loss of affinity of binding for the antigen, but may also lead to a reduced pairing efficiency. Within one B-cell, typically and normally only one light and one heavy chain is expressed, but in the few instances that other light or heavy chains are expressed (such as in two fused B-cells), mispairing between the chains will occur, and antigen binding is lost in this fraction of the antibody preparation. For example, in the past, the expression of multiple antibody variable domains, as in quadromas or cells transfected with multiple heavy and/or light chain genes, typically yields a large fraction of pairings of variable regions that are not functional. In order to build bispecific antibodies, the pairing of different antibody heavy and light chains when expressed in the same cell was investigated intensively. From studies of the pairing in antibodies derived from hybrid hybridomas made by fusing two antibody-producing hybridomas, the pairing was shown to be based on a random association of light and heavy chains with some cases where a certain level of preferential pairing was seen, but not enough to prevent mispairing to occur.

The present invention describes a variety of methods to select antibodies with optimal pairing behavior of antibody chains. With such methods compositions of multiple antibodies with different binding specificities can be made.

1. Antibodies with Pairing-Compatible Variable Regions a. Summary

Herein, we disclose methods and means for obtaining antibodies with pairing-compatible variable regions. The presence of such variable regions facilitate the predictability and functionality of the resulting pairing between the antibody variable regions. Two antibodies contain pairing-compatible variable regions when the pairing of the variable regions in a mixture of all variable regions combined, occurs in such manner that predominantly functional binding sites arise as a result of the pairing. Two antibodies have pairing-compatible variable regions when, for example, the variable light chain domains of both antibodies can be exchanged by the one of the other antibody, without drastically altering the antigen-binding affinity of the two antibodies. Another example of when antibodies have pairing-compatible variable regions, is when they share an identical or closely related variable region. In that case, pairing of the two partner domains to this shared region will lead to the formation of functional binding sites.

Methods for the identification of antibodies that have pairing-compatible variable regions are described. In the simplest form pairing-compatible variable regions in sets of antibodies are identified by virtue of the sequence identity of the V-regions. In another approach pairing-compatible variable regions are identified by empirical exchange of V-genes or V-gene fragments between given antibodies, and testing antigen binding. In another approach, antibodies with a high likelihood of containing pairing-compatible variable regions can be enriched from antibody repertoires by combinations of selections and re-shuffling. Using appropriate selection strategies, antibody pairing may be selected to become promiscuous or exclusive in the context of the desired multiple antibody variable genes. A method is also described for providing a given antibody with pairing-compatible variable sequencing, using various mutagenesis and selection technologies. In another approach, antibodies with pairing-compatible variable regions are selected from synthetic antibody libraries with a high probability of identifying antibodies with such elements (for example, from a library with only one variegated variable domain). Further, antibodies with pairing-compatible variable regions are created by first selecting an antigen-specific single-domain antibody, and then providing this with a second domain that will pair with the first one to form a two-domain molecule.

Pairing-compatible variable regions can be identified in order to replace sequences in an antibody by the equivalent sequences of another antibody that are thought to mediate more favorable characteristics. The transfer of pairing-compatible variable regions between antibodies can be used to alter the pairing capability and pairing strength of the antibody chains, but it can also be envisaged to alter the immunogenicity, idiotype and expression yield of antibodies. Antibodies bearing such elements are also highly suitable for making pharmaceutical compositions of antibodies with multiple binding sites, for example, for making mixtures of antibodies containing such elements, by co-expression in the same host cell. In particular, when the variable regions share a full variable domain (such as the light chain), co-expression will yield functional binding sites only. Antibodies with pairing-compatible variable regions are suitable for the creation of mixtures of antibodies, in which the antibodies are either solely monospecific, or bispecific, or a mixture of mono- and bispecific antibodies, or even, depending on the choice of isotypes with more than two binding sites (e.g., sIgA, IgM), combinations of multiple specificities within the same antibody molecule. Such approaches provide a means to have in the same pharmaceutical preparation antibodies with multiple specificities, and, if required, combinations of specificities within the same molecule.

b. Sources of Antibodies

Antibodies suitable for the invention can be derived from a variety of sources, including monoclonal antibodies, phage antibodies, antibodies from transgenic animals etc. Monoclonal antibodies are obtained from a population of substantially homogeneous antibodies using the hybridoma method first described by Kohler and Milstein, *Nature* 256:495 (1975) or may be made by recombinant DNA methods. In the hybridoma method, a mouse or other appropriate host animal, is immunized to elicit lymphocytes that are capable of producing antibodies that will specifically bind to the antigen used for immunization. Alternatively, lymphocytes may be immunized in vitro. Lymphocytes are fused with myeloma cells using a suitable fusing agent, such as polyethylene glycol, to form a hybridoma cell. Antibodies can also be isolated from transgenic animals that harbor human immunoglobulin genes.

Antibodies or antibody fragments can also be isolated using display-based antibody library technology, wherein antibody fragments are selected by exposing a library of such antibodies displayed on the surface of phage, yeast or other host cell, to the antigen of interest, and isolating those antibody fragments which bind to the antigen preparation. A display library is a collection of entities; each entity includes an accessible polypeptide component and a recoverable component that encodes or identifies the peptide component. Many antibody fragments have been displayed on the surface of entities that carry the genetic material encoding the antibody fragment inside the entity, such as bacteriophages. This format is termed "phage display." Phage display is described, for example, in Ladner et al., U.S. Pat. No. 5,223,409; Smith (1985) *Science* 228:1315-1317. Other display formats utilize peptide-nucleic acid fusions. Polypeptide-nucleic acid fusions can be generated by the in vitro translation of mRNA that includes a covalently attached puromycin group, e.g., as described in Roberts and Szostak (1997) *Proc. Natl. Acad. Sci. U.S.A.* 94:12297-12302, and U.S. Pat. No. 6,207,446. The mRNA can then be reverse transcribed into DNA and cross-linked to the polypeptide. In still another display format the library is a cell-display library. Proteins are displayed on the surface of a cell, e.g., a eukaryotic or prokaryotic cell. Exemplary prokaryotic cells include *E. coli* cells, *B. subtilis* cells, spores, exemplary eukaryotic cells include yeast such as *Saccharomyces cerevisiae, Hansenula polymorpha, Pichia pastoris, Kluyveromyces lactis*, insect cells and mammalian cells. Methods for the display of antibody fragments and the construction of antibody libraries in a variety of formats are well described in the literature and known to those skilled in the art.

c. Identifying Pairing-Compatible Elements in Panels of Antigen-Reactive Antibodies Antibodies with pairing-compatible variable region sequences and, therefore, suitable pairing behavior of variable regions, are identified by a variety of methods that are disclosed within this document. In a first approach, antibodies with pairing-compatible variable regions are selected from panels of antigen-specific antibodies (in which the antigen can be one defined target antigen but also a collection of different antigens, and the panel contains at least two antibodies), as follows. The sequences of heavy and light variable regions are determined and inspected to find clones with identical or highly similar light or heavy chain variable domains. If the amino acid sequence of part of or the complete variable region is identical for two antibodies, the two given antibodies have a pairing-compatible variable region.

In another approach, pairing-compatible variable regions are identified in amino acid sequences that appear related yet have amino acid differences: for example, if there are differences in the amino acid sequence but the same or related germ line segment is used, or when highly similar CDR regions are used, or if similar canonical folds in some CDR regions are found yet different germ line segments are used, the variable regions may still comprise pairing-compatible variable regions. This is confirmed by swapping the variable region(s) between the antibodies in the panel, and measuring antigen binding of the new pairs. Experimentally light and heavy chains or parts thereof can be exchanged by recombinant DNA methods such as restriction enzyme-based DNA cloning, oligonucleotide-based mutagenesis, gene synthesis and PCR-mediated mutagenesis, methods which are widely available in the art. Binding assays that can be used are well established in the art and known to those skilled in the art; some are described below. This method may identify cases in which both variable regions can be exchanged between two antibodies, such as two related light chains that can be swapped with no or an acceptable effect on the affinity. It can also identify cases in which only one of the variable regions of the two antibodies can tolerate the exchange, for example, one light chain that functionally pairs with one of two heavy chains only, while the other light chain can functionally pair with both heavy chains. In that case the latter light chain can be used to replace the former non-matching one and, thus, create two antibodies with pairing-compatible variable regions. Functional pairing means that the variable region pairing has ideally no effect on antigen-binding affinity or specificity, but allowable may also be a <10-fold reduction in affinity, and at the most a 100-fold reduction in affinity, or any improvement of affinity.

Figure 2:
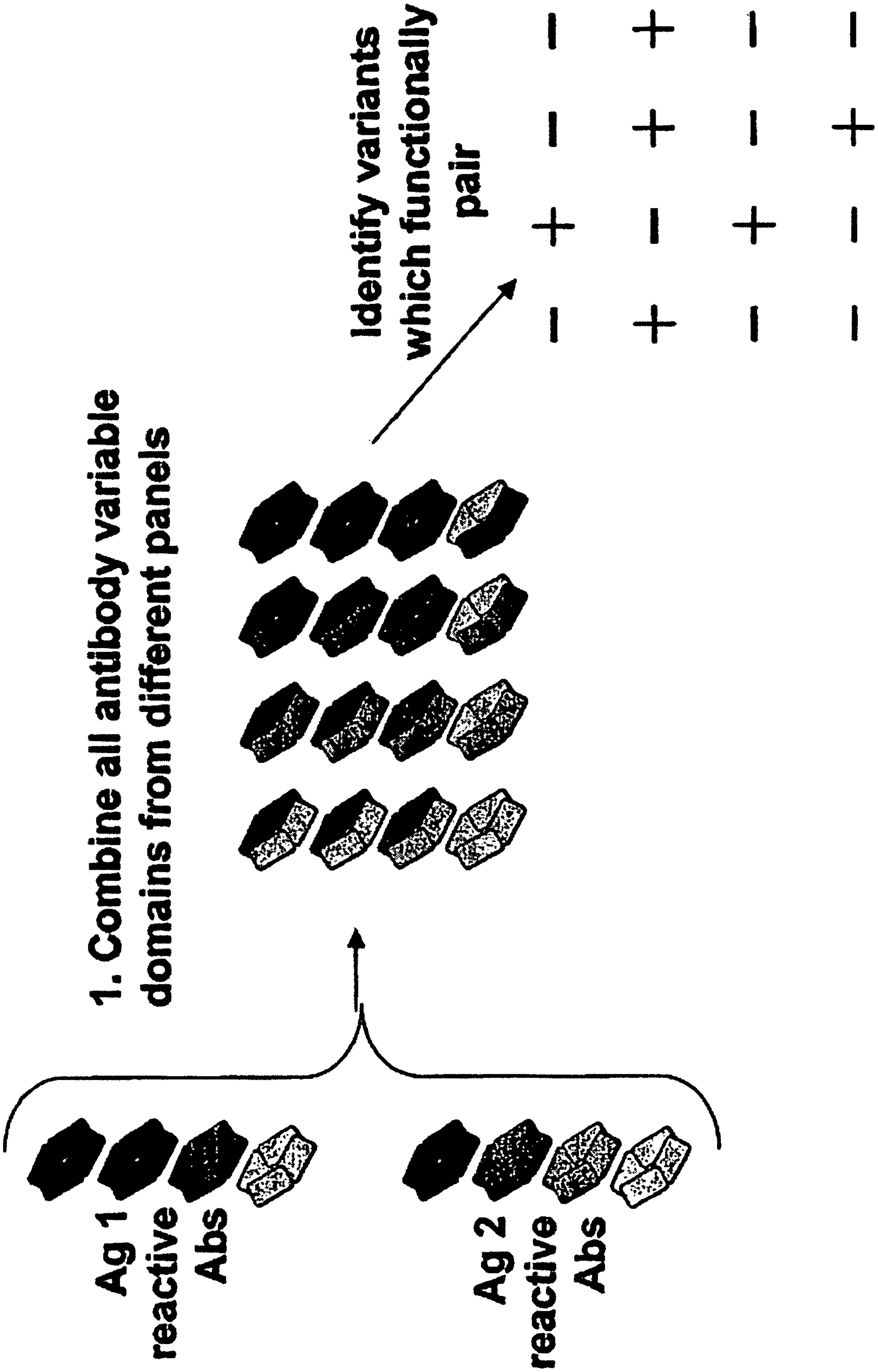
FIG. 2: Method to identify antibodies with pairing-compatible elements by empirical analysis of antibody variable region combinations.

In another embodiment, pairing-compatible variable regions are identified in panels of antibodies without knowing or using the sequence of the variable regions of the antibodies. First a collection of antibody variants is created in which all variable regions are combined with the other partner variable regions of the antibodies in the panel. Then the effect on antigen binding is established empirically, to identify those antibodies with can functionally pair to the variable regions of the other antibodies in the panel (FIG. 2). This method identifies pairing-compatible variable regions that are not immediately identified by sequence comparison. Instead of using the partner variable regions derived of the antibodies in the panel, also other partner variable regions can be used. For example, the heavy chain variable region of each of the antibodies in the panel is combined with a set of chosen light chain variable regions, for example, consisting of mainly germ line encoded segments representative of one or more of the light chain kappa or lambda gene families. Pairing-compatible variable regions are then identified by screening the combinations for antigen binding and scoring whether one common variable region provides antigen binding for the desired set of antibodies in the panel. These methods can be based on assessment of antigen binding of individual combination of the variable region genes, thus co-expression of two variable regions in the desired antibody format, or of antigen binding of multiple combinations of variable regions derived from co-expression in the same host cell. For example, two antibody heavy chain variable regions can be expressed inside the same host cell as Fd chain, and co-expressed with one light chain, and antigen binding for both antibody binding sites assessed. Further, by differentially tagging the two heavy chains, for example, with epitope tags such as tags derived from c-myc, VSV, HA, etc., the pairing of the two H-L combinations can be followed. Such an approach is suitable for finding pairing-compatible variable regions if a limited number of starting antibodies is available and allows the screening of large collections of partner variable regions.

Examples of pairing-compatible variable regions are V-regions based on highly homologous germ line segments, or V-regions that differ by changes in the amino acid sequence (e.g., with somatic or other mutations, minor deletions, additions, substitutions). In such case the effect of the exchange of the homologous region in the first antibody may differ from the effect seen with the exchange of the homologous region in the second antibody; e.g., there are cases where the affinity is changed to an allowable level for only one of the two antibodies, and cases where this occurs for both antibodies. In one embodiment, the pairing-compatible variable region comprises the light chain variable region or part of the light chain variable region. In another embodiment, the pairing-compatible variable regions comprise the heavy chain variable region or part of the heavy chain variable region.

Another embodiment of an approach to identify pairing-compatible variable regions in a panel of antibodies is the following. First the variable region of each of the antibodies is co-expressed with a partner variable region derived from the other antibodies in the panel, and a screen carried out that will detect the presence of intact antibody (thus, not antigen binding). The formation of intact antibody indicates pairing between the two variable regions; if no intact antibody is retrieved, this will indicate that the two variable regions are not pairing inside the host cell. The screening can be used to identify antibodies that display variable regions that cannot pair with one another in the chosen antibody format, i.e., as Fab fragments expressed in *E. coli* or as IgG molecules expressed in eukaryotic cells. When co-expressing the four variable region genes, only the cognate interactions occur, and the variable region genes are pairing-compatible.

d. Antibodies with Pairing-Compatible Variable Regions From Antibody Libraries

In certain embodiments, antibodies with pairing-compatible variable regions are selected from synthetic antibody libraries with a high probability of identifying antibodies with such elements. Synthetic antibody libraries are collections of antibodies which have been synthetically diversified (e.g., using site-directed mutagenesis or PCR-based gene synthesis using mutagenized oligonucleotides) in defined regions/locations within their variable regions. In one embodiment, the design of the diversity introduced into the primary antibody repertoire is such that at least a portion of a variable region and preferably a complete variable region is not diversified, while the remaining area contains the diversity (examples in FIGS. 3, 4(*a*), 4(*c*) and 4(*d*)). Examples of such libraries are libraries based on human variable region genes, for example, a set of 49 different heavy chain genes with diversity introduced in the VH-CDR3, all combined with a single light chain (H. R. Hoogenboom, et al. (1992) *J. Mol. Biol.* 227:381-388). Antibodies selected from such repertoires will contain by design pairing-compatible variable regions. Such repertoires can be created by recombinant DNA methods and displayed on the surface of phage, cells, spores, ribosomes, or can be created in transgenic mice carrying only partial diversity in the V-gene composition. Synthetic diversity can be introduced in all CDR residues, in a subset of CDR residues, i.e., those with significant solvent exposure, and can be designed to encode all or a subset of amino acids, i.e., those that are commonly observed in natural antibody CDRs. An example of such tailored antibody library, with a single heavy chain variable domain scaffold and a fixed light chain variable domain, and with a limited number of heavy chain CDR residues variegated with a limited number of encoding amino acids is described in *J. Mol. Biol.* 338:299-310 and in WO 03/102157A2. Alternatively, to libraries with synthetic diversity in one variable region, also libraries with natural diversity, or combinations of natural and synthetic diversity (e.g., synthetic diversity in CDR1 and CDR2 and natural diversity in CDR3) in one variable region may be used.

Figure 4:
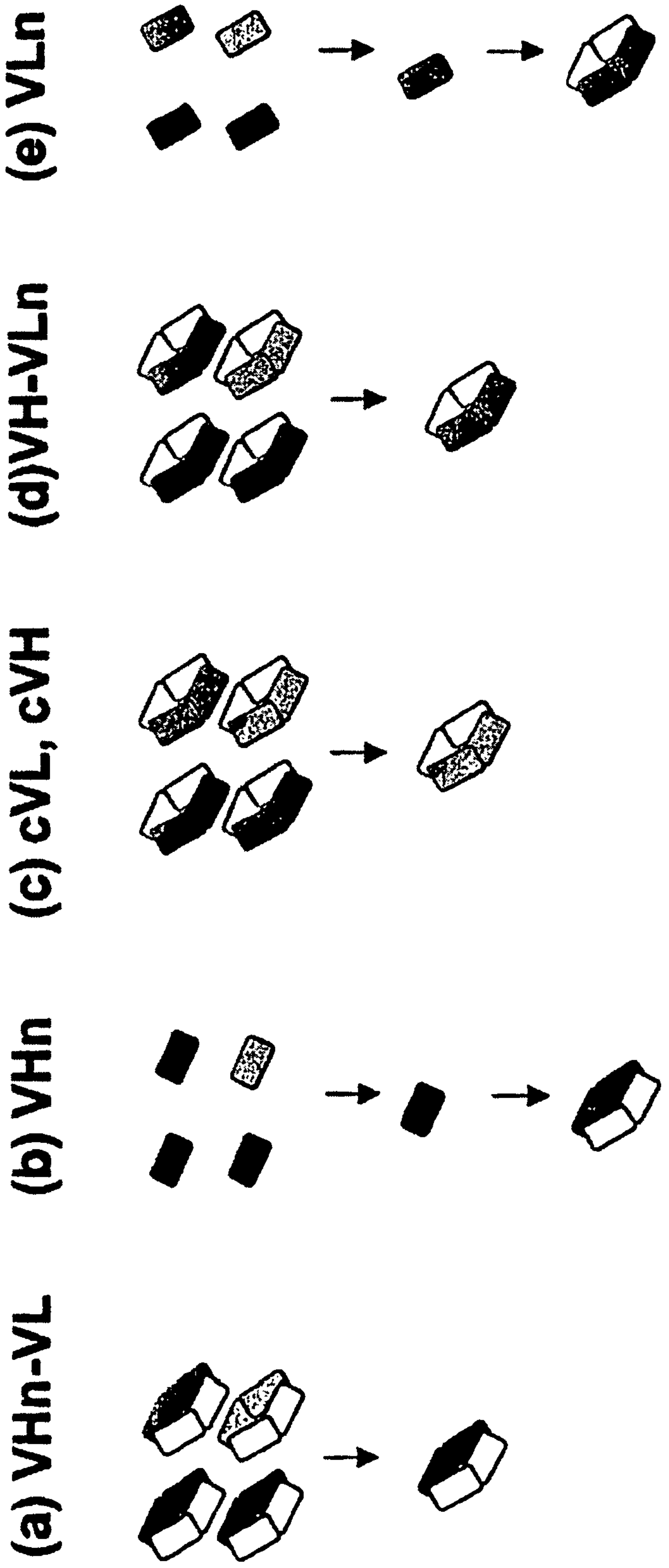
FIG. 4: Different approaches to select antibodies with appropriate pairing behavior. (a) selection of Fab library with constant light chain, and equivalent for Fab library with diversity in light chain only in (d); (b) selection of antigen-binding single-domain antibody from heavy chain only library, and equivalent for VL in (e); (c) selection of library of chimeric chains of VH and VL (in which, for example, some CDR elements are swapped).
Figure 5:
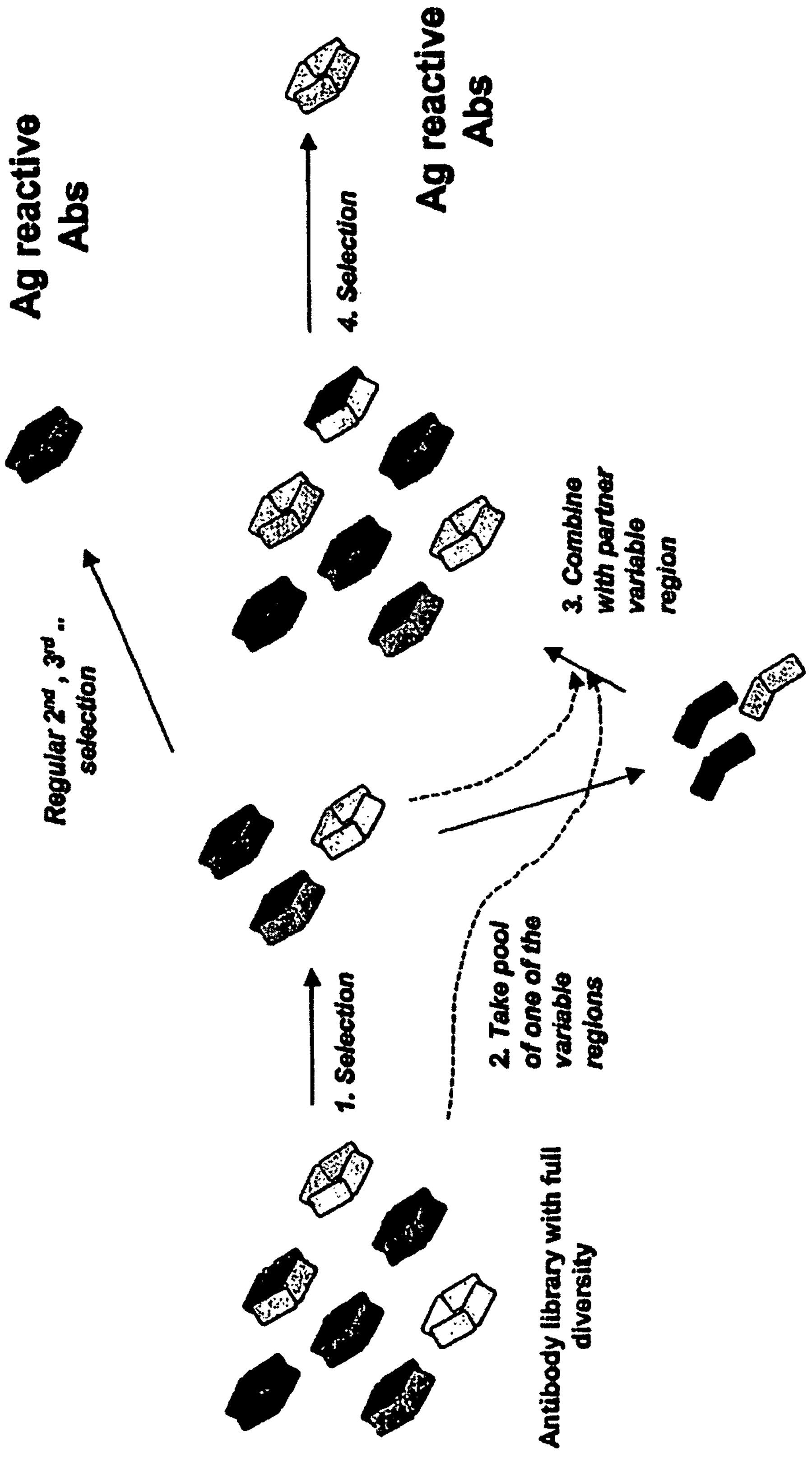
FIG. 5: Selecting antibodies with pairing-compatible variable regions by re-shuffling one chain. Starting point of the method is a repertoire of antibody binding sites, with paired variable regions, such as in this example, an Fab repertoire. Similarly single chain Fv libraries can be used. In a typical selection (top) the initially present pairing of variable regions is maintained throughout the iterative selection process; in the selection followed by reshuffling (steps 1-3), one of the two variable regions (preferably of the heavy chain) of the pairs that have been selected on antigen, is combined with partner domains (preferably light chains) derived from either the selected population or from the original population). After this the selection (step 4), and the subsequent procedure are repeated. Eventually, individual antigen-reactive antibodies are identified by screening methods.

In one embodiment, antibodies with pairing-compatible variable regions are obtained by first selecting an antigen-specific single-domain antibody, and then providing this with a second domain that will pair with the first one to form a two-domain molecule (examples in FIGS. 4(*b*) and 4(*e*)). Single-domain antibodies are preferably isolated from in vitro display repertoires made from single-domain repertoire of certain human variable region fragments, such as human VH or human VL repertoires. In another embodiment, single domain antibodies are isolated from non-immunized, immunized or synthetic VHH repertoires, based on antibody heavy chain domains naturally devoid of light chains (e.g., camel, lama or some shark antibodies). Single-domain VH-based antibodies with antigen-binding activity can be combined via recombinant DNA technology with a single, a small repertoire, a chosen collection or a large repertoire of light chains, preferably of human nature. Antigen-binding variants of single-domains now forced to contain a paired light chain, may be isolated using display technology based or equivalent methods. In another embodiment, single-domain VL-based antibodies with antigen-binding activity are combined via recombinant DNA technology with a single, a small repertoire, a chosen collection or a large repertoire of heavy chains, preferably of human nature. Antigen-binding variants of single-domains now forced to contain a paired heavy chain, may be isolated using display technology-based or equivalent methods. In the embodiments of FIG. 5, the variants derived from the same route of isolation will always share a variable region sequence, thus will be able to provide functional pairing when brought into the context of pairing multiple variable regions.

If at least a portion of a variable region and preferably a complete variable region is not diversified, while the rest of the variable region(s) contain the diversity, the selected antigen-binding antibodies coming from such repertoires will contain by design pairing-compatible variable regions. In many of the approaches in the literature used for building high affinity antibodies from synthetic antibody libraries, diversity in the initial library is built up throughout the antibody variable region genes and, in particular, in most of the six CDRs. Depending on the genetic make-up of these libraries, there will be a higher or lower probability of identifying antibodies with pairing-compatible variable regions. Libraries can be designed to fit specifically this new application, by introducing diversity in one variable region only, and not further diversifying the shared variable region, even in further affinity maturation processes. Preferably, libraries are used in which the diversity is restricted to the three CDRs in one chain. The partner-variable region is then preferably one or a small set of germ line gene-encoded regions without any further diversity. In the primary library or follow-up libraries, diversity can be introduced in those areas of the antibody V-regions that are less likely to interact with the partner chain, so as to increase the chances of finding antigen-binding antibodies with high affinity, yet well pairing variable regions.

Antibodies with a high likelihood of containing pairing-compatible variable regions can also be enriched from antibody repertoires not biased in their genetic make-up, by combinations of selections and re-shuffling of preferably the complete V-region of a given population or clone (exemplified in FIG. 5). This will enrich for those antigen-specific antibodies with a high likelihood of containing pairing-compatible variable regions, for example, because they are tolerant in their pairing with the shuffled region yet retain antigen-binding, or because the shuffled region is less likely to contribute to antigen binding. For example, an antibody Fab library is first enriched on antigen, and the selected heavy chains obtained after one or more rounds of selection are then recombined with the selected or unselected light chain repertoire (dashed lines in FIG. 5), and selected again on antigen (FIG. 5, step 4). In this way the selected antibody variable heavy chain domains will have the propensity to bind to the antigen relatively independently of the light chain to which it is paired. Antibodies to a first and second antigen can be identified by using the above-described selection and re-shuffling experiment, followed by a screening as before, to detect antigen binding of the selected heavy chains in combination with a collection of light chains. One may then identify those antibodies that bind either the first or the second antigen relatively independently of the light chain, or in the present of a related light chain family member. Due to the dominance of the heavy chain in antigen binding in these antibodies, many of the light chains are likely to functionally pair with the multiple heavy chain variable regions. Co-expression of antibodies with a pairing-tolerant variable region that is mediating antigen binding (such as the VH), and in which the partner domain is not involved or not important for antigen binding (such as the VL), will similarly lead to the formation of mainly or only functional binding sites.

In another embodiment, the invention describes a method to obtain antibodies with heavy and light variable regions that preferentially or in the best case, exclusively, pair to one another and not to the respective light and heavy variable regions of one or more other antibodies, for example, those that are co-expressed in the same host. Such selection can be done by display methodology, but also using an intracellular selection route that relies on co-expression of antibody light and Fd chains in the same cell, allowing competition between the chains, and rescue of the intended combination via phage display or any other suitable route. The preferential or ideally exclusive pairing that is encountered in faithful antibodies will aid in the formation of mainly or only functional binding sites when such antibodies are co-expressed. This method essentially allows a high level of functional antibody binding sites to form even when variable region genes are used that have very distinct compositions. A method for identifying antibodies with desired pairing behavior based on competition selection is described here. Antibodies are selected from a library of antibody fragments, by carrying out a selection directly in a host cell that co-expresses different antibodies. For example, when applied to using bacteriophage libraries, this concept is the following: bacteria are provided with a phage or phagemid genome that carries the genes encoding a Fab fragment in such manner that upon expression, one of the chains will be anchored to a phage particle. In the same host cell, other antibody light and/or heavy chain Fd fragments are co-expressed, for example, the Fab genes encoding a given antibody, or any set of multiple antibodies. For example, consider co-expression of two Fabs in the same cell, one of which is anchored via its heavy chain (Fd fragment, essentially VH-CH1) to the phage coat protein. As a consequence of this co-expression, competition occurs inside the same cell (in this case in the periplasm) between the two light chains for the pairing to the phage-anchored Fd chain. Further, the soluble heavy chain of the competing Fab will be able to pair with both light chains present in the same cell. In this system, phage particles with antigen binding activity will occur with different types of pairings. First, if the correct light chain will pair with its partner heavy chain on the phage only (exclusive pairing), and secondly, if the heavy chain on the phage surface is dominant in antigen binding and tolerant for pairing, yielding antigen binding virtually irrespective of which light chain it pairs with. Functionally such antibody pairs will behave in the same manner. In the case of the first situation, the lesser interactions between the partners of the two respective antibody pairs, the higher the proportion of functional Fab on phage. The method described can be further biased towards antibodies with preferably an exclusive pairing, by providing tags on the chains and enriching or depleting for particular combinations (e.g., depleting for those phage that carry the competitor light chains via a unique tag present on these chains). This method when applied to the isolation of antibodies via the selection of a phage library of Fabs, will yield a high frequency of antibodies that will have an appropriate pairing behavior and high functional yield when produced as mixture by co-expression. The use of competition-selection to bias selected antibodies towards being co-expression compatible, may also be applied to other display libraries (e.g., yeast display libraries), and to in vitro library systems based on ribosome display or mRNA display (Puromycin system), with methods of screening or selection of antibodies that recognize antigen as extensively described in the art. Further, the described method of competition-selection of antibody fragments for improved pairing (or antigen-selection and compatible pairing) using phage display can be readily translated into an intracellular (periplasmic) selection system based on protein-or enzyme complementation. In such approaches, fragmented, complementary or self-inhibitory enzymes are used to drive the selection of interacting molecules that are fused to the components of the selection system. Only when there is an interaction of a minimal strength will the protein or enzyme become activated, and under appropriate selection conditions, will the cells survive. Such methods have, for example, been described for the enzymes beta-lactamase and DHFR, with its applications in the selection of antibodies or expressed cDNA fragments that display a particular binding behavior. For example, competitive selection has been described for the affinity maturation of antibodies in the TACZYME system from Kalobios Inc. In the current invention, it is not the antigen binding but the pairing strength that can be made the selective force for a given population of antibodies presented in such system.

Figure 6:
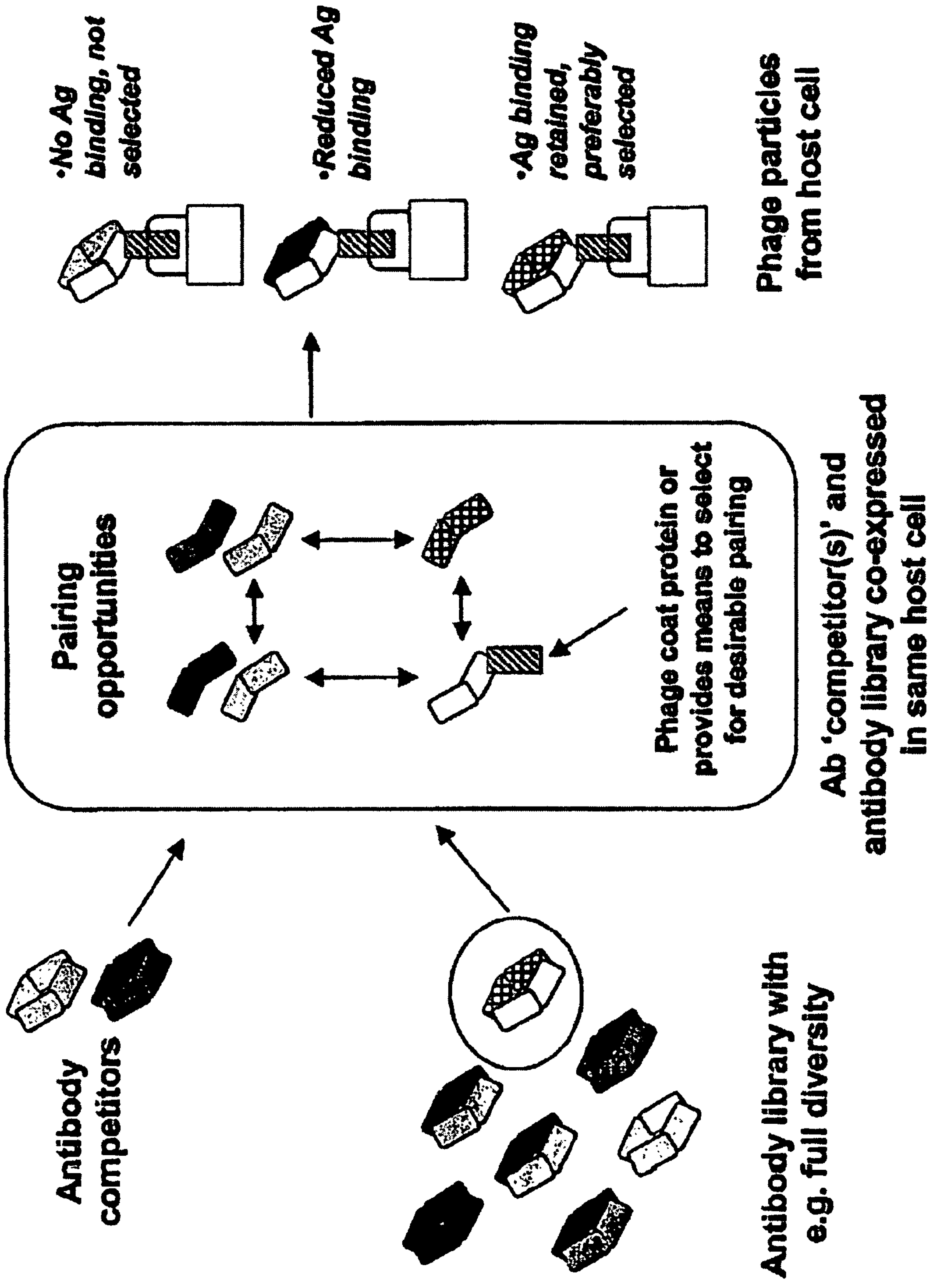
FIG. 6: Example of a competitive selection of antibodies with a desirable pairing behavior. The method involves the co-expression of one or more competing antibodies (top, left) in the same host cell as a member of an antibody library (bottom, left). Depicted is the method for Fab fragments, as described in the text. The result of the pairing opportunities of VHCH1 (white boxes) chain when co-expressed with two other Fab fragments is depicted. The original combination of the VH with its cognate light chain (hatched box), will retain its original binding affinity for antigen and can thus be selected.

In a preferred embodiment, the method is used to identify new antibodies from phage libraries that show pairing-compatible variable regions with an existing antibody that has given variable region sequences. The antibody with the known antigen specificity is cloned for co-expression as Fab fragment in host cell that collectively express a phage display library of human Fab antibodies. This can be done by providing the Fab expression cassette onto a plasmid that is compatible with the presence of a phage or phagemid genome, such as the pBR322-based plasmid. Host cells harboring this plasmid are then infected with the phage particles encoding a library of human Fabs cloned into, for example, a phagemid vector such as pUC119, or a phage vector such as fd-tet-DOG1. While the competing Fab fragment is expressed, new phage particles are harvested (after helper phage infection if appropriate) from this culture. These particles are used for selection on antigen, and the resulting phage reinfected into cells harboring the competitor Fab fragment. After a few iterative rounds, the phage Fabs are screened for antigen binding in a binding assay; the pairing behavior between the reactive Fabs and the variable regions of the competing Fab can be further tested by co-expression and binding assays. The preferred format for this selection is the Fab format and not the scFv format, mainly because for most applications whole IgG-type antibodies will need to be established that have interactions between the chains that harbor the variable regions that mimic those seen in the Fab format. FIG. 6 depicts an example of how this method works for two Fabs competing with antibodies in a phage library.

This method requires some optimization steps, for example, the use of a CH1-mutant with reduced affinity for its CL, and Fabs that do not display an intermolecular disulphide bridge such that the pairing will remain noncovalent. Residues positioned at the CH1-CL interface region may be mutated such that affinity between these two domains is reduced, for example, 10-fold or 100-fold, and as a result in the Fab format the pairing of the variable domains will become more dominant in driving the two chains together. Antibodies selected from such mutated Fab libraries, or from Fv libraries in which there is no covalent association between the two variable regions, may be biased towards having a preferential pairing behavior.

In a further embodiment, the invention comprises the creation of antibody libraries in which provisions are made to mediate unique pairing between the heavy and light chains, such that they are unlikely to interact with antibodies derived from a "regular" or non-purposely biased composition. An example of such provision is a knobs-into-holes engineered CH3—CH3 pair, in which one domain is provided with an amino acid with a large, bulky side chain (e.g., a tyrosine; the knob) that pokes out into the interface region, while the other domain at the equivalent structural position, carries one or more mutations (e.g., three) to create a hole into which the "knob" will fit. Examples of such engineered domain interfaces have also been published for variable regions (Zhu et al. (1997) *Protein Science* 6:781-788). It was shown that the effects of domain interface mutants are context (antibody) dependent, which provides also an opportunity to engineer the variable region domain interactions in an antibody-specific manner, in such way that when multiple antibody variable gene pairs are allowed to pair, mainly or only the cognate pairings are retrieved. Alternatively, installing a disulphide bond between the domains may mediate a preferential pairing. Alternatively, charge replacements are introduced in the framework regions, or combinations of these with sterically complementary mutations, to disfavor mispairing with one, and/or more favorable pairing with the other partner variable region. Selection systems for such mutant libraries have been described earlier, and include the selection of the domain libraries on antigen via phage display of the paired variable regions (in scFv or Fab or, IgG format), or ribosome display of the scFv fragments, or selections based on the interaction itself instead of that with antigen. An example of the latter is described for selecting heterodimers of the immunoglobulin gamma-1 CH3 domain (Atwell et al. (1997) *J. Mol. Biol.* 270:26-35), which is applicable for the present invention as follows: on of the two variable regions that should or should not interact (depending on what one would like to select for, repulsion or attraction/pairing) is displayed on phage (preferably as VLCL or as VHCH1 chain), while the other is genetically tagged and produced in solution (preferably as VHCH1 or as VLCL). The interaction between the two variable regions can than be selected for, using standard phage selection protocols and anti-tag reagents. Co-expression with a pair of non-tagged competitor variable regions as described earlier can be used to drive the selection towards variable region pairs that exclusively pair with one another.

In another embodiment of selecting binding sites with appropriate pairing behavior, we describe here the use of antibodies derived from VH-VH libraries on the one hand and VL-VL libraries on the other; or the use of chimeric libraries in which elements (one or more CDR regions) are swapped between VH and VL. In another embodiment, the invention comprises the creation of two antibody libraries with such provisions made to mediate unique pairing between the heavy and light chains, such that when antibodies from these libraries are co-expressed, they will likely preferentially pair with the right partner.

Cited libraries of antibodies can take various forms. As a source of antibodies, a naive human library may be used, such as the antibody libraries described by Griffiths (A. D. Griffiths, et al. (1993) *EMBO J.* 12:725-734), Vaughan (T. J. Vaughan, et al. (1996) *Nat. Biotechnol.* 14:309-314), or de Haard (H. J. de Haard, et al. (1999) *J. Biol. Chem.* 274:18218-18230). Both heavy and light chains in these libraries are derived from the repertoires of rearranged V-genes derived from the mRNA of peripheral blood lymphocytes (PBLs) from unimmunized humans and are, therefore, highly diverse. Alternatively, as a source of antibodies an immunized host or patient with biased humoral response (e.g., patients with infections, autoimmune diseases, etc.) is used. In immune libraries made from a hapten-immunized animal, it was shown that many of the clones were promiscuous and allowed pairing of the originally selected heavy and light chains with partner chains derived from other selected clones. Thus, antibodies with pairing-compatible variable regions may be more frequent in such immune libraries than in non-immune libraries.

Cited selection and screening technologies of recombinant antibodies and their fragments are well established in the field. Antigen-specific polypeptides can be identified from display libraries by direct screening of the library, or can be first selected on antigen to increase the percentage of antigen-reactive clones. The selection process may be accomplished by a variety of techniques well known in the art, including by using the antigen bound to a surface (e.g, a plastic surface, as in panning), or by using the antigen bound to a solid phase particle which can be isolated on the basis of the properties of the beads (e.g., colored latex beads or magnetic particles), or by cell sorting, especially fluorescence-activated cell sorting (FACS). As will be apparent to one of skill in the art, the antigen-specific affinity reagent may be bound directly or indirectly (e.g., via a secondary antibody) to the dye, substrate, or particle. Selection procedures have been extensively described in the literature (see, e.g, Hoogenboom (1997) *Trends Biotechnol.* 15:62-70). Other publications describe the production of high affinity (nanomolar range) human antibodies from very large collections of antibodies, and the affinity maturation of these antibodies by chain shuffling or other approaches (reviewed in, e.g., H. R. Hoogenboom, et al. (2000) *Immunol. Today* 21:371-378). Binding of antibodies to their respective antigens may be carried out using antibody-based assay techniques, such as ELISA techniques, Western blotting, immunohistochemistry, Surface Plasmon Resonance (SPR) analysis, affinity chromatography and the like, according to methods known to those skilled in the art (see, for example, Sambrook et al., 1989, *Molecular Cloning: A Laboratory Manual, 2nd Ed.*, Cold Spring Harbor Laboratory Press). These techniques are viable alternatives to the traditional hybridoma techniques for isolation of "monoclonal" antibodies (especially when human antibodies are required), which are encompassed by the present invention.

The following describes possible embodiments of exemplary assays for binding assays: ELISA. Polypeptides encoded by a display library can also be screened for a binding property using an ELISA assay. For example, each polypeptide is contacted to a microtiter plate whose bottom surface has been coated with the target, e.g., a limiting amount of the target. The plate is washed with buffer to remove non-specifically bound polypeptides. Then the amount of the polypeptide bound to the plate is determined by probing the plate with an antibody that can recognize the polypeptide, e.g., a tag or constant portion of the polypeptide. The antibody is linked to an enzyme such as alkaline phosphatase, which produces a colorimetric product when appropriate substrates are provided. The polypeptide can be purified from cells or assayed in a display library format, e.g., as a fusion to a filamentous bacteriophage coat. In another version of the ELISA assay, each polypeptide of a library is used to coat a different well of a microtiter plate. The ELISA then proceeds using a constant target molecule to query each well.

Surface Plasmon Resonance (SPR). The binding interaction of a molecule isolated from library of diversity strands with a target can be analyzed using SPR. For example, after sequencing of a display library member present in a sample, and optionally verified, e.g., by ELISA, the displayed polypeptide can be produced in quantity and assayed for binding the target using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance). The changes in the refractivity generate a detectable signal, which are measured as an indication of real-time reactions between biological molecules. Methods for using SPR are described, for example, in U.S. Pat. No. 5,641,640; Raether (1988) *Surface Plasmons*, Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Information from SPR can be used to provide an accurate and quantitative measure of the equilibrium dissociation constant ($K_d$), and kinetic parameters, including $k_{on}$ and $k_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $k_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $k_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Homogeneous Binding Assays. The binding interaction of candidate polypeptide with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos et al., U.S. Pat. No. 4,868,103). Another example of a homogenous assay is Alpha Screen (Packard Bioscience, Meriden Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding. The homogenous assays can be performed while the candidate polypeptide is attached to the display library vehicle, e.g., a bacteriophage.

Automated screening. The methods and compositions provided herein are also suitable for automated screening of diversity libraries for finding clones with likely pairing-compatible variable regions. For example, a display library of Fabs or scFvs can be screened for members that bind to a target molecule. The library can be screened directly or first selected on antigen once or several times. Binders from a first round of screening can be amplified and rescreened, one or more times. Binders from the second or subsequent rounds are individually isolated, e.g., in a multi-well plate. Each individual binder can then be assayed for binding to the target molecule, e.g., using ELISA, a homogenous binding assay, or a protein array. These assays of individual clones can be automated using robotics. Sequences of the selected clones can be determined using robots and oligonucleotide primers that allow to read the variable region sequences of the selected clones. Results of the assay and the sequences can be stored in a computer system and evaluated by eye or by using software, e.g., to identify clones which meet particular parameters (e.g., for binding affinity and/or specificity, and for sequence homology).

e. Forcing Appropriate Pairing of Antibody Variable Regions Via Mutation and Selection There are instances where antibodies with given variable region sequences, antigen specificity and affinity are available, but where no pairing behavior can be achieved with the existing sequences. Some of the methods mentioned earlier can be applied to solve this, in particular, the screening of a combinatorial panel of variable region pairs to find fortuitously compatible pairs, or the selection of new antibodies that do have the desirable pairing behavior, for example, using competition selection with one of the antibodies of defined specificity. In those instances where this is not a desirable option and preferably the existing antibodies are used, the following methods may be used to create pairing-compatible variable regions for the set of antibodies to be produced as an Oligoclonic™ mixture.

First of all the pairing can be biased by using single-chain Fv variants of the antibodies. The provision of a linker between heavy and light chain variable region will increase the chance that the two domains will pair with one another, instead of pairing with unlinked molecules or with other single chain Fv molecules of the same or different specificity present in the same cell. If such molecules are fused to Fc regions and co-expressed in the same host cell, the result is a mixture of scFv-Fc molecules which are paired via the heavy chain Fc region, forming monovalent and bispecific molecules. There is also an alternative solution that does not rely on pairing in the scFv format. With a set of, for example, three given antibodies, an antibody mixture consisting essentially of IgG-formatted molecules can be made by making the variable region genes compatible with one another. First the sequence of the antibody light chains is determined, and the chain that is the most common to the sequence of the two other light chain variable regions, or the closest to its germ line amino acid sequence identified. For the two antibodies that carry the different light chain, a library of heavy chains is created that is diverse in the CDRs including the CDR3 that produces a substantial fraction of the interactions between heavy and light variable region sequences. These heavy chains are combined with the chosen, non-mutated light chain in a format that provides expression and screening, or display and selection capabilities. In such manner, the two remaining antibodies are forced to accept the new light chain, which could affect pairing and affinity; the provision of mutations in the heavy chains and the selection (either separately as scFv or Fab fragments, or as Fab in competition with their original light chain in a method described above for competition selection), will enrich for variants that have corrected a possible deficiency in pairing efficiency and/or affinity loss.

f. Antibodies with Pairing-Compatible Variable Regions from Transgenic Mice

It is possible to produce transgenic animals (e.g., mice) that are capable, upon immunization, of producing a full repertoire of human antibodies in the absence of endogenous immunoglobulin production. Transfer of the human germ-line immunoglobulin gene array in mutant mice that carry a homozygous deletion of the antibody heavy chain joining region (JH) gene and, therefore, do not anymore produce murine antibodies, results in the production of human antibodies upon antigen challenge. See, e.g., Jakobovits et al., *Proc. Natl. Acad. Sci. U.S.A.* 90:2551-255 (1993); Jakobovits et al., *Nature* 362:255-258 (1993). Antibodies with pairing-compatible variable regions may be identified from panels of antibodies made in these animals, or from such antibodies and antibodies derived from other methods. It is envisaged that antibodies with pairing-compatible variable regions may be identified even more readily in transgenic mice carrying only the heavy or only the light chain locus, and only a single or a limited set of chosen partner chains; in that case immunization would lead to the generation of antibodies which all carry a compatible common chain. Antibodies with pairing-compatible variable regions are then identified using the methods described herein. The efficiency with which such antibodies can be identified can be further increased by reducing the extent of somatic hypermutation of the partner chain or chains. This can, for example, be done by removing regulatory sequences surrounding the variable regions, or by mutating the variable region codons such that the gene becomes a less likely substrate for the cellular hypermutation machinery, or by harvesting the B-cells earlier after immunizations.

One further approach is to combine the heavy chains of the three antibodies with a repertoire of highly diverse light chains, and screen the pairings, if necessary after selection on antigen, for light chains that maintain functional pairing (and antigen binding) and share a common sequence. This can be readily carried out using automated facilities for high throughput ELISA screening and sequencing, as presented earlier.

g. Uses of Antibodies with Pairing-Compatible Variable Regions

Antibodies with pairing-compatible variable regions have many applications. It is disclosed herein that the preparation of a desired functional antibody mixture is feasible when the composition of the variable heavy or light chains of the various antibodies is carefully selected to contain antibody variable regions that carry pairing-compatible variable regions such that the pairing of the antibody variable regions yield predominantly functional binding sites. After selection of antibodies with pairing-compatible variable regions as described above, the antibody variable region genes can be cloned into expression vectors that will direct the expression of an antibody of the desired format, e.g., IgG, IgA, IgM. In one embodiment, the invention describes the production of mixtures of antibodies through the co-expression of variable region genes operably linked to constant region genes, in which these variable region genes encode different antibodies with pairing-compatible variable regions. Without the selection of appropriately pairing antibodies with pairing-compatible variable region, co-expression would lead to the formation of a mixture of antibodies with many non-functional heavy-light chain combinations. When appropriate pairing-compatible variable regions have been defined, a high level of functional antibody combining sites will arise. In one embodiment, the heavy chain variable region is operably linked to the first domain of the heavy chain constant region, followed by a hinge region, followed by the remaining domains of the heavy chain constant region. The variable region of the light chain on the other hand is operably linked to an appropriate constant domain of the kappa or lambda family.

In a preferable embodiment, the pairing-compatible variable region is an identical light chain. In that case the co-expression of this light chain and, for example, two different heavy chains derived from antibodies with as pairing-compatible variable region the full light chain, in the same cell will yield a mixture of the two expected bivalent molecules and one bispecific molecule. Similarly, when co-expressing this light chain with more than two heavy chains derived from antibodies that all have functional antigen binding sites when paired to that same light chain, the mixture will contain in a certain fraction each of the bivalent molecules, and a number of bispecific molecules with combinations of all binding sites, e.g., three when three antibody heavy chains are introduced, six when four antibody heavy chains are introduced, ten when five antibody heavy chains are introduced, etc. In this case, the affinity of the monomeric binding sites in these various species is expected to be very similar to the affinity of the original binding sites. In another embodiment, antibodies share a pairing-compatible variable region, but the sequence of this element is different between the two antibodies and, upon swapping, the affinity of one or both of the antibodies may be altered. If such antibodies are used for co-expression, the final antibody mixture will contain antibodies with the original and the altered binding affinity in all of the species that were mentioned above. In the preferred embodiment, such antibodies share a compatible common light chain. In another embodiment, antibodies share a compatible common heavy chain. The expression levels of the individual components can be chosen or can be manipulated to alter the fraction of the species of antibodies containing that component.

2. Protein Mixtures with Optimally Paired Variable Regions

Using the methods according to the invention, antibodies with a pairing behavior suitable for the preparation of well-defined biopharmaceutical mixtures are obtained. Traditionally before use for human therapy, protein drugs are expressed and purified to homogeneity, consisting of one major molecular species. In some cases, therapy is more efficacious with combinations of proteins or other drugs. This invention describes methods to make a proteinaceous mixture that will contain at least two major molecular species, composed of at least three variable regions, and such that some variable regions pair to form a functional binding site. The large-scale manufacturing of the proteinaceous mixture is a prerequisite for their clinical use, and a simple purification procedure is an important feature of the development process. The presence of inappropriately paired variable regions would inevitably lead to a more complicated purification procedure. In one embodiment, the genes encoding the components of the two proteinaceous compounds are co-expressed in the same host cell, and the different major molecular species that are present in the mixture and have a functional binding specificity purified using biochemical/biophysical techniques well known in the art. In one embodiment, the method is used to make a mixture of a defined number of antibodies. The major molecular species that comprise one or more different binding specificities could share a minimal proportion of their encoding genetic information (e.g., an Fc region, a common tag, or another shared domain or feature); such shared feature will provide a common mechanism/assay for following the individual compounds in the mixture. In another embodiment, the major molecular species are preferentially co-purified due to a similar biophysical/biochemical behavior, or due to a shared domain that mediates co-purification (e.g., an Fc). In another approach, the major molecular species are fused to a subunit of a protein such that they can multimerize with each other (e.g., CH2-0H3 region). The invention also provides biopharmaceutical mixtures produced using this method. The preferred application is the co-expression of antibodies, with the choice of the V-genes and pairing behavior between VH and VL domains such that mainly or only functional binding sites are made, and the purification of the mix can occur via the shared feature, an Fc region. Methods for purification of immunoglobulin are well known in the art, including protein A, protein G and other affinity matrices. Other proteinaceous mixtures that could be envisaged to have paired variable regions are fusion proteins between antibodies or antibody fragments and other molecules, single domain antibodies derived from camel, llama or engineered single domain antibodies from murine or human variable region genes, receptor extracellular domains, peptides, proteins equipped with an engineered binding site, or cytokines. Preferably, the proteinaceous compounds share a feature (like by further fusion to an immunoglobulin Fc region; methods well known in the art), such that they can be co-purified using the same procedures. The optimal pairing of the variable regions in the different proteinaceous compounds will also lead to an optimal level of functional binding sites on these compounds, thus minimizing the number of purification steps required to obtain the active component of the protein mixture.

3. Selecting Antigen-Specific Proteinaceous Compounds Using Mixtures of Encoding DNA In a preferred embodiment, the proteinaceous compounds are antibodies. In the invention antibodies are identified in collections or pools of genetically diverse antibodies, in which the pairing of the variable genes is optimized in such manner that upon co-expression of at least two antibodies inside the same cell an optimal pairing arises, providing a maximal amount of functional binding sites. In a preferred embodiment, the pairing of all binding sites is optimized due to the use of a shared variable region gene, preferably the light chain. The diversity of the other elements in the library will be such that antibodies with high affinity can still be selected. Due to this choice of the genetic make up of the variable regions, the pairing of the antibody variable regions will be such that a very high level of functional binding sites will be present when multiple variable regions forming more then one antibody binding site are contacted with one another, for example, when expressed in the same cell. In one embodiment, first a library or collection of different antibody heavy chain genes is made, and cloned into an eukaryotic cell expression vector. This library is introduced into host cells in such a manner that each host cell will be making multiple different antibody heavy chains. In a preferred embodiment, “anti-repressor elements” (Kwaks et al., 2003, *Nat. Biotechnol.* 21:553) are cloned at one or both ends of the antibody heavy chain gene. Such elements confer stable and high level expression of a given transgene as shown in this citation, and in this invention we describe its use to mediate stable and high level expression for each individual copy of the transgene (see also below).

Figure 7:
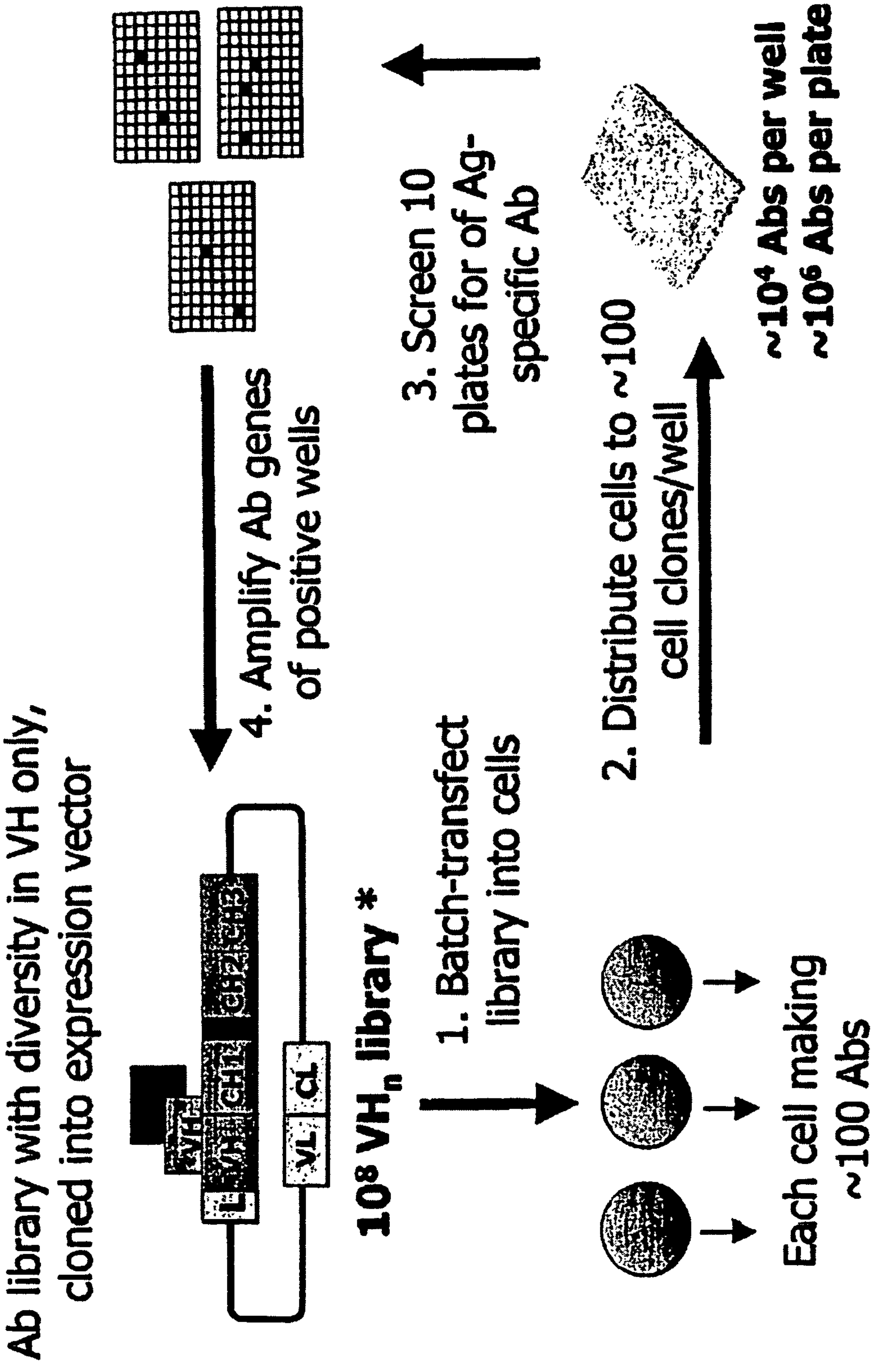
FIG. 7: Identifying antigen-specific antibodies by co-transfecting heavy chain gene libraries with an invariant light chain gene and screening the resulting antibody mixtures for antigen reactive antibodies. With every cycle of transfection and screening, the diversity of the VH library is reduced (at position *), to eventually yield a population of antigen-reactive heavy chain variable genes. The numbers indicate that sampling of a library of $10^8$ different heavy chains can be carried out by screening the wells of ten 96-well tissue culture with each 100 clones per well.
Figure 8:
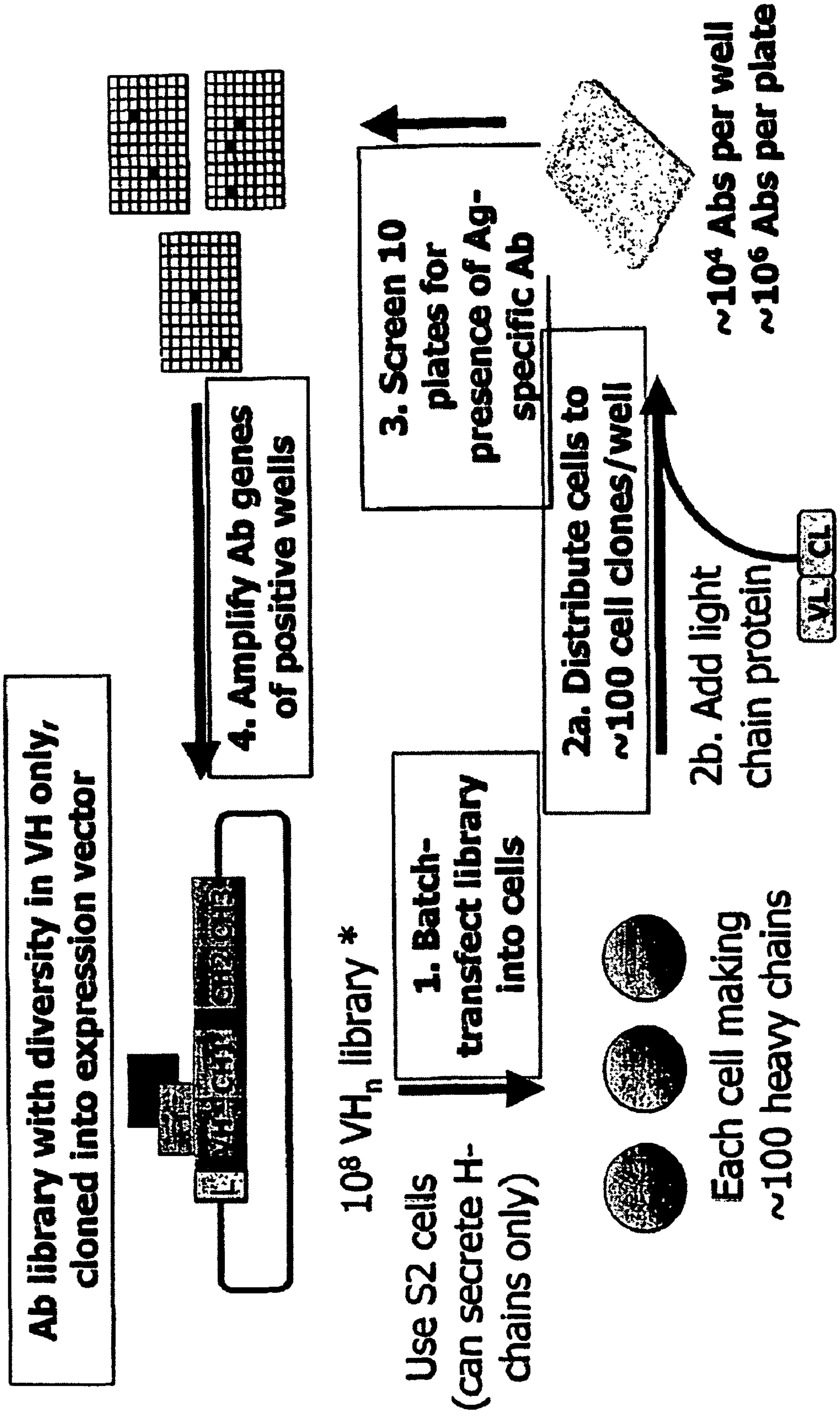
FIG. 8: Identifying antigen-specific antibodies by transfecting secretable heavy chain gene libraries, assembly with an invariant light chain and screening the resulting antibody mixtures for antigen reactive antibodies. With every cycle of transfection and screening, the diversity of the VH library is reduced (at position *), to eventually yield a population of antigen-reactive heavy chain variable genes.

In one embodiment of this invention, depicted in FIGS. 7-8, the variable region or regions with optimized pairing behavior for the other variable regions is or are also genetically encoded in an appropriate expression vector, and introduced into the host cell, either before, during or after the introduction of the other variable region. The expression cassette with the variable regions can also be part of a viral system such that high levels of transfection/infection efficiency can be achieved. In the case that the pool of first variable regions are antibody heavy chains, the second variable region with optimized pairing behavior can be one or more light chains. The host cells which are transfected with both partners of the pairing, e.g., the mix of antibody heavy chains and set of light chains, are expanded and grown under conditions which allow the expression of heavy chains and light chains. Preferably only one light chain is used, as exemplified in FIG. 7. For example, the expansion can occur in tissue culture wells, in such a manner that the tissue culture wells will contain between 10-1000 different originally transfected clones, each of the clones expressing multiple pairings of the antibody variable regions. Antigen-specific antibodies can be retrieved amongst these clones and wells by various methods, preferable by ELISA or equivalent test of the antibody mixtures of each well (see also earlier description of binding assays). If stable transfection is used, with the possibility to select transfected cell lines for stably integrated copies of the antibody encoding DNAs, the relevant antibody or antibodies may be cloned via limiting dilution. Alternatively, the DNA encoding the relevant antibody variable genes can be retrieved by amplifying and sequencing the antibody genes from the cells in the well using methods know in the art. If required, the antibody-heavy chain encoding DNA can be also amplified, recloned for expression in the same system, the DNA amplified and then used to repeat the transfection, expression and screening experiment. With this cycle of transfection and screening, after a few rounds, an antigen-reactive antibodies start dominating the population. At every round, the complexity of the mixture produced by an individual cell can be reduced by reducing the complexity of the DNA introduced into the cell, to eventually become a oligoclonal population. From the transfected wells, the antibody’s V-gene can be rescued directly (e.g., via PCR) and further analysis and/or screening in this system, eventually at conditions that provide expression of the monoclonal antibody. Alternatively, the variable regions from reactive wells can be cloned into other systems for rapid screening of the binding specificity of the individual pairs of variable regions, e.g., via bacterial expression of antibody fragments or whole IgG, expression in other hosts, via in vitro display methods, bacteriophage display methods etc.

In another preferred embodiment, the heavy chains are secreted by the host cell into the supernatant, where they can be reconstituted into functional antigen binding fragments, by the addition of and pairing with a partner light chain. This can be a small family of related chains, but preferably one chain only. In this approach, cells are used that do not prevent secretion of the non-paired heavy chain. This embodiment is depicted in FIG. 8. *Drosophila* S2 cells have been described that contain a BiP (Binding Protein) homologue, hsc72, that specifically interacts with immunoglobulin heavy chains, but does not prevent their secretion. Alternatively, the heavy chains will need to carry amino acid mutations in such a manner that cells that normally retain heavy chains when they are not paired to light chains, will not mediate retention anymore. For example, mutations can be provided for or, selected within, the major recognition sites for BiP sites which are located in the heavy chain CH1 domain. For example, the CH1 domain can be replaced (e.g., by a CL or CH3 region) as long as the light chain can pair with this form of the molecule (or other variants, see also section on antibody cross-over variants), or mutated to avoid retention by BiP. The results of such variations are that the different heavy chains are secreted by the host cell. The chains are then reconstituted with one or more partner chains carrying the partner variable region(s). Methods to establish this have been extensively reviewed in literature on the biochemical analysis and assembly of antibody molecules. Antigen-reactive variable region pairs can be identified in the same way as described for the other embodiment.

In yet another embodiment, antibody the first partner of the two paired variable regions (such as the heavy chain for an antibody) is anchored onto a eukaryotic cell surface, and the other variable region provided by expression in the same host cell or via reconstitution on the cell-surface. This set-up allows a direct screening for antigen-binding on the host cell surface, for example, via flow cytometry with fluorescently-labeled antigen, or a direct selection, for example, via cell sorting methods.

Methods to identify antigen-reactive antibodies from B-cell populations have been described in the literature and can be applied to these transfection-based systems also. In such described systems, random combinatorial diversity is sampled, and antibody variable gene pairing is also not optimized or biased. Use of such random combinatorial pairs of variable regions does not guarantee that upon production of an antibody mixture, the pairing will be optimal; on the contrary, mispaired variable regions will be a substantial fraction of the produced proteinaceous compounds. In this invention an important element is that this random combinatorial diversity is limited, by reducing the diversity of one of the variable region genes. The diversity that is present in the resulting paired repertoire originates mainly from one of the variable regions. Preferably, it is one or a small set of light chains. As a consequence, in the iterative process of selecting the antigen-reactive variable regions, only one of the two partners of the pair will need to be identified. It is not necessary to retrieve both the heavy and light chain variable region sequence from the same cell. Another important difference is that multiple antibody genes are introduced and expressed from the same host cell. When using random diversity, such a feature would lead to a multiplication of the diversity and reduction of the quantity of the individual combinations to the extent that detection let alone cloning of the responsible antibody gene combination would become very difficult, if not impossible. Consider the case in which the cell would be making multiple combinations of heavy and light chain pairs, then the chance to retrieve the correct combination of the antibody that mediates antigen reactivity, would be become smaller as the cell is making a higher number of different chains. If the cell would be expressing ten different heavy and light chains, the combinatorial diversity generated by this one cell would be a 100 different types of antibody binding sites; only 1/10 of the antibody variable genes amplified from such cell will be the relevant one, thus the chance to be able to clone the correct antibody genes is very low. As a consequence of this reduced combinatorial diversity in the present system, there will also be a higher quantity of each of the individual antibodies, which makes a more sensitive detection possible. Thus, in this invention the expression of the different antibodies in the same host cell is a desired feature. First as explained above, it is an important feature for the antigen-selection system to find antigen-reactive antibodies when using transfected cell populations. Secondly, the invention is directed towards the production of mixtures of proteins and more in particular, antibodies or their fragments, which requires optimal pairing of the variable regions, in particular, when producing such mixtures by co-expression in the same host cell. In the preferred method described above, co-transfection of variable region genes inside the same cells leads to the expression of multiple antibodies in the same host cell. The methods are thus useful to select individual antibody variable region pairs that are reactive with a given target epitope, but also to select a mixture of different variable region pairs all reactive with a given target epitope (in the process of the screening, multiple antibody variable region pairs will be selected or identified, but when iterating the process, these antibodies are likely to be eventually mixed and end up in the same host cell). Further if the screening or selection of the mixture is carried out with targets with multiple epitopes, or multiple targets, the mixture can also contain antibodies to multiple epitopes or targets, yet with co-expression-compatible pairing of the variable region genes.

Figure 9:
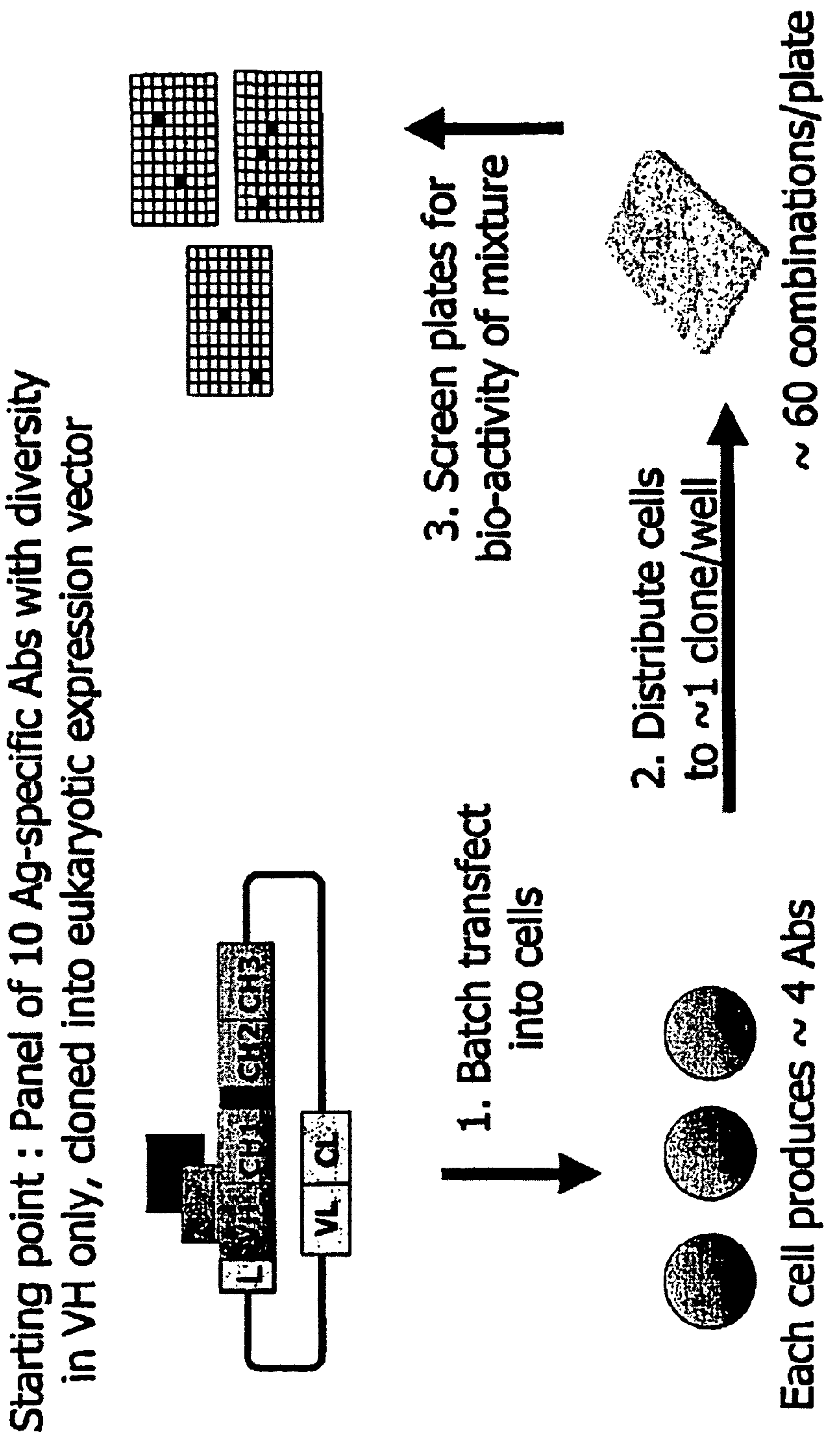
FIG. 9: Screening antibody mixtures produced by the same host cell for optimal bio-activity. Mixtures are made by transfecting heavy chain genes encoding the antibodies of interest (here number is 10) together with optimally paired light chain, followed by cloning of cell lines, selecting stably producing cell lines, and eventually screening the resulting antibody mixtures for optimal bio-activity.

The invention is also suitable for the screening of mixtures of proteins with paired variable regions that have a defined binding specificity (FIG. 9). The genes encoding these compounds are introduced as a mixture into a host cell as above (in FIG. 9 examples is given of ten different antibodies), and individual clones that have integrated some or multiple copies of the genes encoding the various variable regions expanded. In the way described above, applied to antibodies, the supernatants of the resulting cell lines are screened for reactivity towards the various antigens. The levels of each of the individual antibody pairs may vary, and, when the antibody format is the IgG isotype, also the level of the bispecific antibodies resulting from the co-expression may be highly variable. Cells that secrete the mixture comprising the desired composition are identified and used as a stable production host for this mixture. The invention provides a method to quickly screen hundreds of mixtures of different antibodies. The optimized pairing of the heavy and light variable regions will secure a high level of functional binding sites in the antibodies present in such mixtures.

Figure 10:
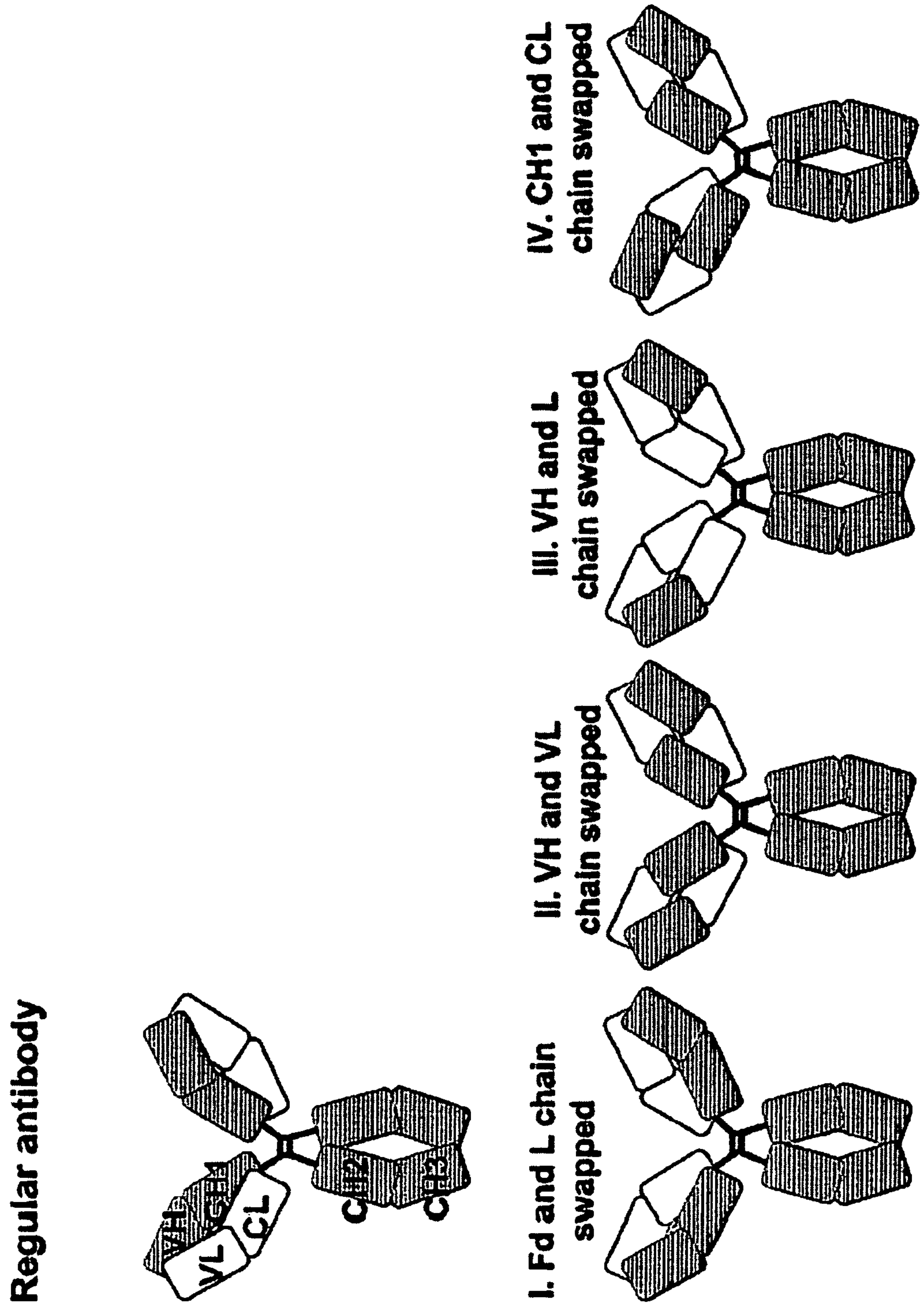
FIG. 10: Examples of antibodies with cross-over domains. Heavy chain domains (grey striped boxes) and light chain domains (white boxes).

4. Antibody-Based Compounds with Paired Variable Regions and Cross-Over or Mutations in the Constant Regions The pairing of the variable and constant regions of an antibody can be further engineered as follows, by crossing-over domains. Antibodies are made by crossing-over or swapping or replacing elements within the Fab region of the antibody (or the antibody heavy chain Fd region and the antibody light chain region), and combining the appropriate elements to establish a binding site in the context of an immunoglobulin molecule (examples are given in FIG. 10). In its simplest format, the L chain and H chain Fd region are swapped. A VL-CL-hinge-CH2-CH3 chain is thus paired to a VH-CH1 domain. In a second format, the constant region genes between H and L are swapped. In another form, the CH1 is replaced by a CL. In another form, the VH and VLs are swapped. In another form, one or more of the CDR regions between VH and VL are swapped. The pairing efficiency can be monitored in such cross-over variants, such that suitable combinations of non-cross-over antibodies with cross-over antibodies, or combinations of different cross-over antibodies, can be used to mediate optimal pairing when making mixtures of at least two antibody molecules (with antibody also including here cross-over variants as described above). In another form the effect of mispairing between different VHs and/or VLs is reduced by linking the VH and VL via a linker to a single-chain Fv variant, which will favor the association between these two domains. Alternatively, the pairing between variable regions can be manipulated by the introduction at the appropriate positions of cysteines which upon pairing of the variable heavy and light variable domains can form a disulphide bridge. The invention also provides methods for selecting antibody fragments that will bind antigen in an appropriate cross-over format, by selecting from appropriately formatted libraries, or by screening one or more antigen-binding antibodies for the activity in the cross-over format. Antibodies in which the CH1 domain is not part of the heavy chain may be secreted as free molecules not paired to light chains, allowing alternative approaches for the production of antibodies and new fusion formats. Antibodies in which the variable regions are swapped may be functionally non-equivalent and yield a more diverse, unnatural or different spectrum of antigen-binding or biological activity (the positioning of the heavy and light chain variable regions is expected to not always be completely equivalent). Besides effects of the exchange of the heavy and light chain genes on affinity and/or specificity, the swapping may alter the antibody flexibility and impact the biological behavior. Finally, an antibody binding site with chimeric VH-VL regions (with CDR or FR regions swapped between the two variable domains) may also yield an alternative, possibly larger but structurally non-overlapping set of antibody paratopes.

Secondly, selective engineering of the constant regions or the interaction of variable regions with constant regions may also affect the pairing behavior of the variable region genes. By modifying the antibody heavy chain constant region, the fraction of functional bispecific antibodies can be increased or decreased. In this approach, antibody heavy chains can be engineered to drive hetero- or homodimerization. This can be done by introducing sterically complementary mutations in the CH3 domain interface, for example, as has been described in the literature for increasing the percentage of functional bispecific antibodies in the mixture of antibodies arising from the co-expression of two heavy and two light chains. The pairing of the antibody binding site variable region may thus be influenced by the pairing of variegated constant regions, of heavy and light constant region domains.

5. Extracellular Pairing of Proteinaceous Mixtures

Figure 11:
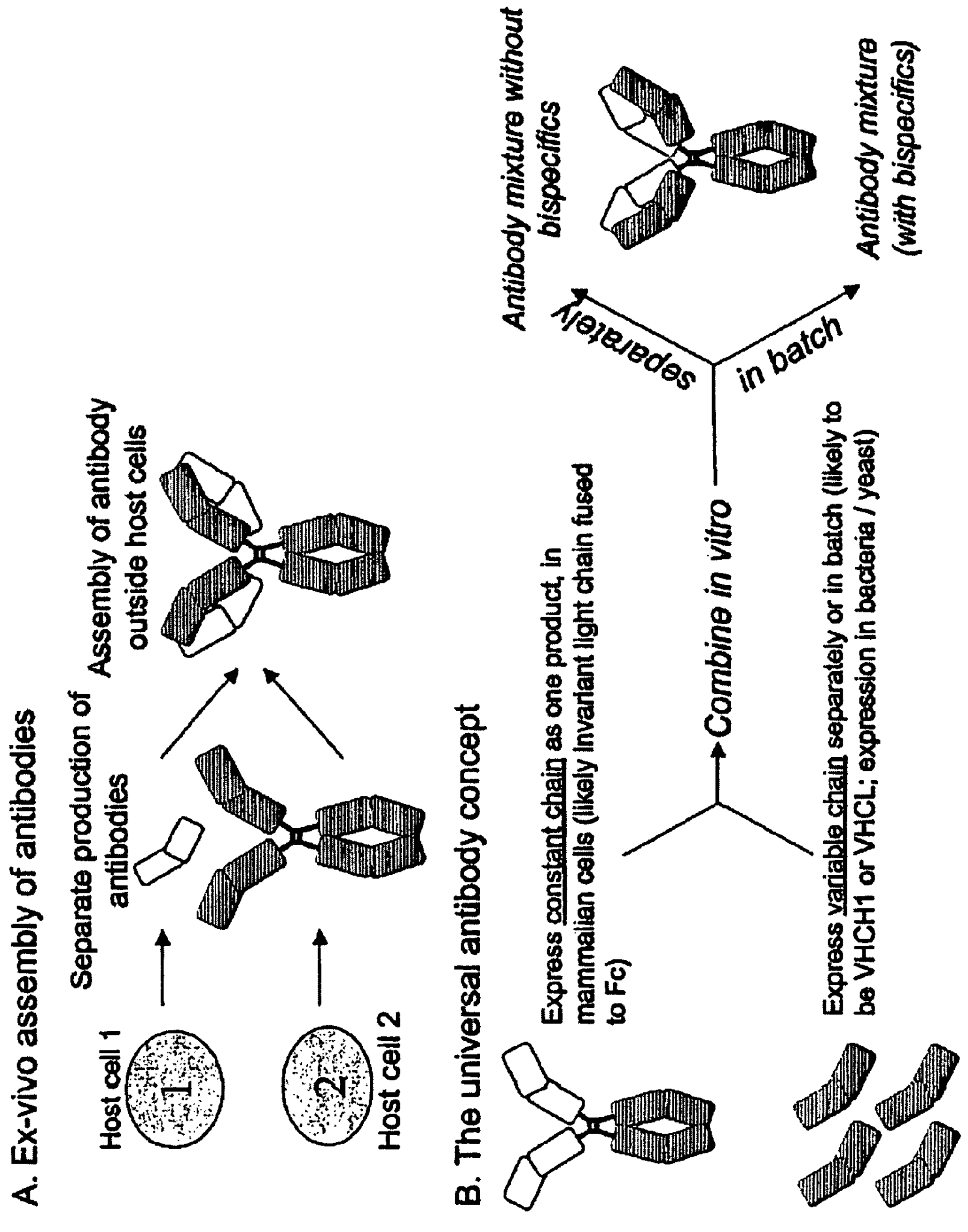
FIG. 11: Ex vivo assembly of antibodies (A) and the universal antibody concept (B). Antibodies are produced as separate chains and then combined to form a functional antibody. This is in particularly interesting when making mixtures of antibodies, as indicated in (B), where depending on the input of the chains and the separation of the mixing reactions.

This invention provides a method for making whole antibodies using an in vitro pairing procedure of heavy and light chains produced in different host cells. In one embodiment, one of the two antibody chains is expressed in a first host cell and the other chain is expressed in a second host cell (FIG. 11A). The antibody chains are then brought together under conditions in which pairing of the two domains will occur, thus outside of the cell. In one embodiment, the pairing occurs in vitro, with purified chains and under conditions that are optimized for the pairing of the desired variable regions. In another embodiment, the expression occurs via the use of one or two dummy-chains, temporarily paired to the respective variable regions, removing the dummies from their partner via a mild and controllable process, and pairing the appropriate unpaired variable regions to one another to form a functional binding site. In one embodiment applied to antibodies, this association is made easier by using heavy-light chain pairs mutated in one or the other chain to facilitate the process of the pairing, e.g., mutated in the cysteine residue that normally forms the bridge between H and L chains (either both mutated, for example, to Ser, or only one mutated and not the other), or mutations that have altered the affinity of one chain for the other or, preferably, mutations in the dummy chain used for the temporary pairing, in particular, the one that pairs with the heavy chain; thus such dummy light chain will pair with a native, non-mutated heavy chain, and may carry mutations such that it can be readily removed from the purified antibody.

An extension of this concept is that it is possible to produce antibodies using universal antibody chains (FIG. 11B). The invention provides a method for expressing a shared, invariant variable region contained into the appropriate chain format (e.g., a VL-CL light chain) in a given host cell, and the other chain (e.g., a heavy chain consisting of VH-CH1 or VH-CH1-hinge-CH2—CH3) that is dominant in or provides most or all of the specificity, in another host cell. For production of two antibodies, three chains need to be made, which can be assembled in vitro to form two different antibodies. For example, if the light chain is identical, only one VL-CL domain will have to be made, and two VH-containing heavy chains. These can then be assembled extracellularly, preferably in vitro. Pairing of the variable regions will have to be optimal such that the proteinaceous mixture yields a high level of functional binding sites. The light chain can be used universally for all antibodies that will accommodate it (and antibodies accordingly selected if required). The heavy chain can be expressed in mammalian cells to provide a suitable glycosylation; for the light chains any suitable expression host cell can be chosen. When using this invention with the cross-over variants described in the previous section, in which the light chain is fused to the hinge and Fc, and the heavy chain variable region is provided as the lightest chain (as VH-CH1 or VH-CL), an important advantage of this set-up is apparent: the light chain fused to the Fc (depicted as "constant" chain in FIG. 11B), with its functionally important glycosylation features, can be made as the universal chain. The heavy chain can carry the dominant features for the specificity, and a mixture of heavy chains which will mediate different binding specificities can now be made in a different host cell that does not need to provide glycosylation. Such feature makes the production of mixtures possible in two steps: a cheaper prokaryotic expression can be used to make mixtures of variable regions each encoding a unique binding specificity, while the more expensive production of the other variable region that also requires most fine analysis, can be done in a eukaryotic host. All antibodies that can pair with the latter variable gene without inflicting their overall specificity and affinity, can be produced by extracellular pairing with the same universal chain. The latter can be designed to be optimized for pharmaceutical applications: a broadly expressed, relatively common variable region, with a minimal number of MHC Class II epitopes, of human origin, and germ line in sequence. This procedure of mixing can be done with separate heavy chain mixtures or with a mix of the different heavy chains; when applied to the IgG format as depicted in FIG. 11B, the result is an antibody mixture without or with bispecifics, respectively. Manual mixing and pairing of variable region genes further provides much more control over the pairing, it can be done in a stepwise manner, per antibody, per group of antibodies etc. For some applications, for example, where there is an absolute necessity to avoid the formation of bispecific antibodies in a complex mixture with three or more antibodies, this method has an advantage over the cell line-based approach.

6. Controlling the Expression of Variable Regions in the Context of the Production of Multiple Pairing Variable Regions in the Same Host Cell Nucleic acids encoding variable region, e.g., from antibodies, can be co-expressed in the same cell to make mixtures of different functional binding sites. With appropriate pairing behavior, a high level of functional binding sites will be present. It will however also be important to control the expression of the individual variable regions and their expression ratios, because this will effect the composition of the final antibody mixture. The expression level and the stability of the expression is a function of the site of integration of the transgene: if the transgene is integrated close to or within inaccessible chromatin, it is likely that its expression will be silenced. In this invention, we describe the use for the production of mixtures of antibodies in the same cell, of elements that, when flanking the antibody genes, will increase the predictability of the expression level, the yield, and improve stability. Such elements can, for example, do this by counteracting chromatin-associated gene repression. Such anti-repressor elements provide a high level of predictability of expression, high levels of expression and stable expression overtime, of the antibody mixture (Kwaks et al., 2003, *Nat. Biotechnol.* 21:553). Such elements confer stable and high level expression of a given transgene as shown in this citation, and in this invention we describe its use to mediate stable and high level expression for each individual copy of a mixture of transgenes, encoding multiple variable regions. A variety of such elements and other systems to achieve a similar result have been identified in the art, including Locus control regions (LCRs), chromatin opening elements, artificial chromosomes (e.g., ACE technology from Chromos Molecular Systems Ltd.), and Ubiquitous Chromatin Opening Elements. For example, LCRs are transcriptional regulatory elements which possess a dominant chromatin remodeling and transcriptional activating capability conferring full physiological levels of expression on a gene linked in cis, when integrated into the host cell genome. In the following section, the invention is described for "anti-repressor elements" but other, different control elements such as the ones mentioned and inasmuch as they provide the opportunity to regulate the high-level expression of multiple genes, may be equally suitable to achieve a controlled expression of the different variable regions.

In one embodiment of the present invention, antibody mixtures are made from variable region pairs in which one dominates the binding, and the other is a shared variable region. In a preferred embodiment, the first variable region one is the heavy chain, and the second is the light chain. In the preferred embodiment, at least one of the antibody heavy chains is flanked by one anti-repressor element, or by two identical or two different anti-repressor elements located at either end of the heavy chain gene; in another embodiment, more than one or possibly all of the heavy chain genes that need to be expressed are flanked by anti-repressor elements. In one embodiment, the heavy chains are based on the same plasmid, in another they are on separate plasmids. In another embodiment, CHO cells are used as host; in another embodiment, PER.C6 cells are used.

The manufacture of mixtures of antibodies expressed in the same cell line will require appropriate variable region pairing and also a stable expression level of all of the antibody chains involved, as well as a stable ratio of the various chains, in such manner that the resulting antibody mixture after manufacture even at GMP conditions, has a stable composition. Such stable compositions can then translate into stable biological activity and stable toxicity profile. If the expression of only one antibody chain would change, it could affect the composition and, therefore, also alter its biological activity. The provision of elements that yield a more predictable and copy-number associated expression level is also important to build cell lines that express similar or even equimolar levels of different antibodies. If, for example, five antibody heavy chains have to be expressed, it will be very difficult to build a cell line that expresses all of these chains at similar quantities when using a random integration and selection approach without the anti-repressor elements. By using such elements, a higher copy number of antibody chains can be introduced without compromising the stability of the resulting cell line. Thus, multiple antibody heavy chains can be introduced, where the number of integrated copies for each heavy chain will also to some level reflect its absolute expression level. With such elements it will be much easier and more rapid to alter the ratios of expression levels between the heavy chains, for example, by manipulating the ratios of the DNAs encoding the heavy chains at the time of the transfection.

This also explains the preferred incorporation of such anti-repressor elements in vectors to be used for creating antibody libraries and select antigen reactive antibodies from these pools (see section 4); anti-repressor elements preferably inserted in the expression vectors that incorporate the heavy chain, on FIGS. 7, 8 and 9.

7. Expression Systems for Multiple Variable Regions in the Context of the Production of Multiple Regions in the Same Host Cell When expressing multiple variable regions inside the same cell, maximal productivity will be achieved only if the partners that need to be paired are co-expressed at an equivalent level, such that there is little chance on what is essentially waste: the non-paired variable region. The composition of the mixture is influenced by manipulating any one of the parameters that affect the expression level achieved in the host cell. The expression level of a given component is a function of many factors including the regulatory sequences that drive the expression of the component, when the component is a heavy chain also the expression levels of the light chains, the choice of the host cell, the method of expression (transient or stable), and, for stable expression, the copy number and site of integration. The expression levels can further be affected by many parameters including choice of the transcriptional regulatory elements (including choice of promoter, enhancer, insulators, anti-repressors, etc.). The expression of the two light and heavy chains of the antibodies that are to be assembled from the mixture of the chains can be done independently for each of the chains, or made dependent from each other.

The expression vector or vectors comprising the antibody genes of interest contain regulatory sequences, including, for example, a promoter, operably linked to the nucleic acid(s) of interest. Large numbers of suitable vectors and promoters are known to those of skill in the art and are commercially available for generating the recombinant constructs of the present invention. Appropriate cloning and expression vectors for use with prokaryotic and eukaryotic hosts are described by Sambrook et al., in *Molecular Cloning: A Laboratory Manual, Second Edition*, Cold Spring Harbor, N.Y. (1989), the disclosure of which is hereby incorporated herein by reference. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, and pRIT5 (Pharmacia). Eukaryotic: pWLneo, pSV2cat, pOG44, PXTI, pSG (Stratagene) pSVK3, pBPV, pMSG, and pSVL (Pharmacia). Promoter regions can be selected from any desired gene using CAT (chloramphenicol transferase) vectors or other vectors with selectable markers. Two appropriate vectors are pKK232-8 and pCM7. Particular bacterial promoters include lad, lacZ, T3, T7, gpt, lambda P, and trc. Eukaryotic promoters include CMV immediate early, HSV thymidine kinase, Elongation-factor-1$\alpha$, early and late SV40, LTRs from retrovirus, mouse metallothionein-I, and various art-known tissue-specific promoters. Methods well known to those skilled in the art can be used to construct vectors containing a polynucleotide of the invention and appropriate transcriptional/translational control signals.

Mammalian expression vectors will comprise an origin of replication, a suitable promoter and also any necessary ribosome-binding sites, polyadenylation site, splice donor and acceptor sites, transcriptional termination sequences, and 5' flanking non-transcribed sequences. Expression regulatory sequences may comprise promoters, enhancers, scaffold-attachment regions, negative regulatory elements, transcriptional initiation sites, regulatory protein binding sites or combinations of the sequences. Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules. In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in $dhfr^-$ host cells with methotrexate selection/amplification) and the neo gene (for G418 selection).

In an exemplary system for recombinant expression of a modified antibody, or antigen-binding portion thereof, of the invention, a recombinant expression vectors encoding at least one antibody heavy or light chain is introduced into $dhfr^-$ CHO cells by calcium phosphate-mediated transfection. Within the recombinant expression vector, the antibody heavy or light chain gene is operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy or light chains. In many instances the expression vector may contain both heavy and light chain genes, and co-transfection will lead to the production of intact antibody, recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

The host of the present invention may also be a yeast or other fungi. In yeast, a number of vectors containing constitutive or inducible promoters may be used. For a review, see, *Current Protocols in Molecular Biology*, Vol. 2, Ed. Ausubel et al., Greene Publish. Assoc. & Wiley Interscience, Ch. 13 (1988); Grant et al., *Expression and Secretion Vectors for Yeast*, in *Methods in Enzymology*, Ed. Wu & Grossman, Acad. Press, N.Y. 153:516-544 (1987); Glover, *DNA Cloning*, Vol. II, IRL Press, Wash., D.C., Ch. 3 (1986); Bitter, *Heterologous Gene Expression in Yeast*, in *Methods in Enzymology*, Eds. Berger & Kimmel, Acad. Press, N.Y. 152:673-684 (1987); and *The Molecular Biology of the Yeast Saccharomyces*, Eds. Strathern et al., Cold Spring Harbor Press, Vols. I and II (1982). The host of the present invention may also be a prokaryotic organism, such as *E. coli*. As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

Introduction of the recombinant construct into the host cell can be effected, for example, by calcium phosphate transfection, DEAE, dextran mediated transfection, or electroporation (L. Davis, et al., *Basic Methods in Molecular Biology* (1986)).

DNA encoding the antibodies of the invention is readily isolated and sequenced using conventional procedures for cloning, DNA preparation and sequencing as described by Sambrook, et al., in *Molecular Cloning: A Laboratory Manual, Second Edition*, Cold Spring Harbor, N.Y. (1989), the disclosure of which is hereby incorporated by reference. For sequencing, oligonucleotide probes can be used that are capable of binding specifically to genes encoding the heavy and light chains of antibodies or to the vector sequences surrounding the gene fragments, and the DNA sequence determined by dideoxy-based sequencing (F. Sanger, et al. (1977) *PNAS* 74:5463-5467). Once isolated, the DNA encoding appropriate regions of the antibody may be placed into expression vectors, which are then transfected into host cells. The host cell can be a higher eukaryotic host cell, such as a mammalian cell, a lower eukaryotic host cell, such as a yeast cell, or the host cell can be a prokaryotic cell, such as a bacterial cell.

In one preferred embodiment, antibodies with pairing-compatible variable regions are produced in mammalian cells. Preferred mammalian host cells for expressing the clone antibodies or antigen-binding fragments thereof include Chinese Hamster Ovary (CHO cells) (including $dhfr^-$ CHO cells, described in G. Urlaub et al. (1980) *PNAS* 77:4216-4220), used with a DHFR selectable marker, e.g., as described in (R. J. Kaufman et al. (1982) *J. Mol. Biol.* 159: 601-621), lymphocytic cell lines, e.g., NS0 myeloma cells and SP2 cells, C127, 3T3, CHO, human epidermal A431 cells, Jurkat, U937, HL-60, mouse L-cells, Baby Hamster Kidney cells, COS or CV-1 cells, PER.C6 cells (M. G. Pau et al. (2001) *Vaccine* 19:2716-2721), other transformed primate cell lines, normal diploid cells, cell strains derived from in vitro culture of primary tissue, primary explants, and a cell from a transgenic animal, e.g., a transgenic mammal. For example, the cell is a mammary epithelial cell. Other cell types suitable for expression, in particular, for transient expression, are simian COS cells (Y. Gluzman (1981) *Cell* 23:175-182), and Human embryonic Kidney cells of lineages 293, 295T and 911 (Hek293, 295T, 911).

Alternatively, it may be possible to produce the antibody as fragment or as whole antibody in lower eukaryotes such as yeast or in prokaryotes such as bacteria (L. C. Simmons et al. (2002) *J. Immunol. Methods* 263:133-147). Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the full antibody is made in yeast or bacteria as IgG, it may be necessary to modify the protein produced therein, for example, by phosphorylation or glycosylation of the appropriate sites, in order to obtain the functional protein. Such covalent attachments may be accomplished using known chemical or enzymatic methods. Recombinant polypeptides and proteins produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine. The recombinant polypeptides encoded by a library of diversity strands can then be purified using affinity chromatography. Microbial cells employed in expression of proteins can be disrupted by any convenient method, including freeze-thaw cycling, sonication, mechanical disruption, or use of cell lysing agents.

Figure 12:
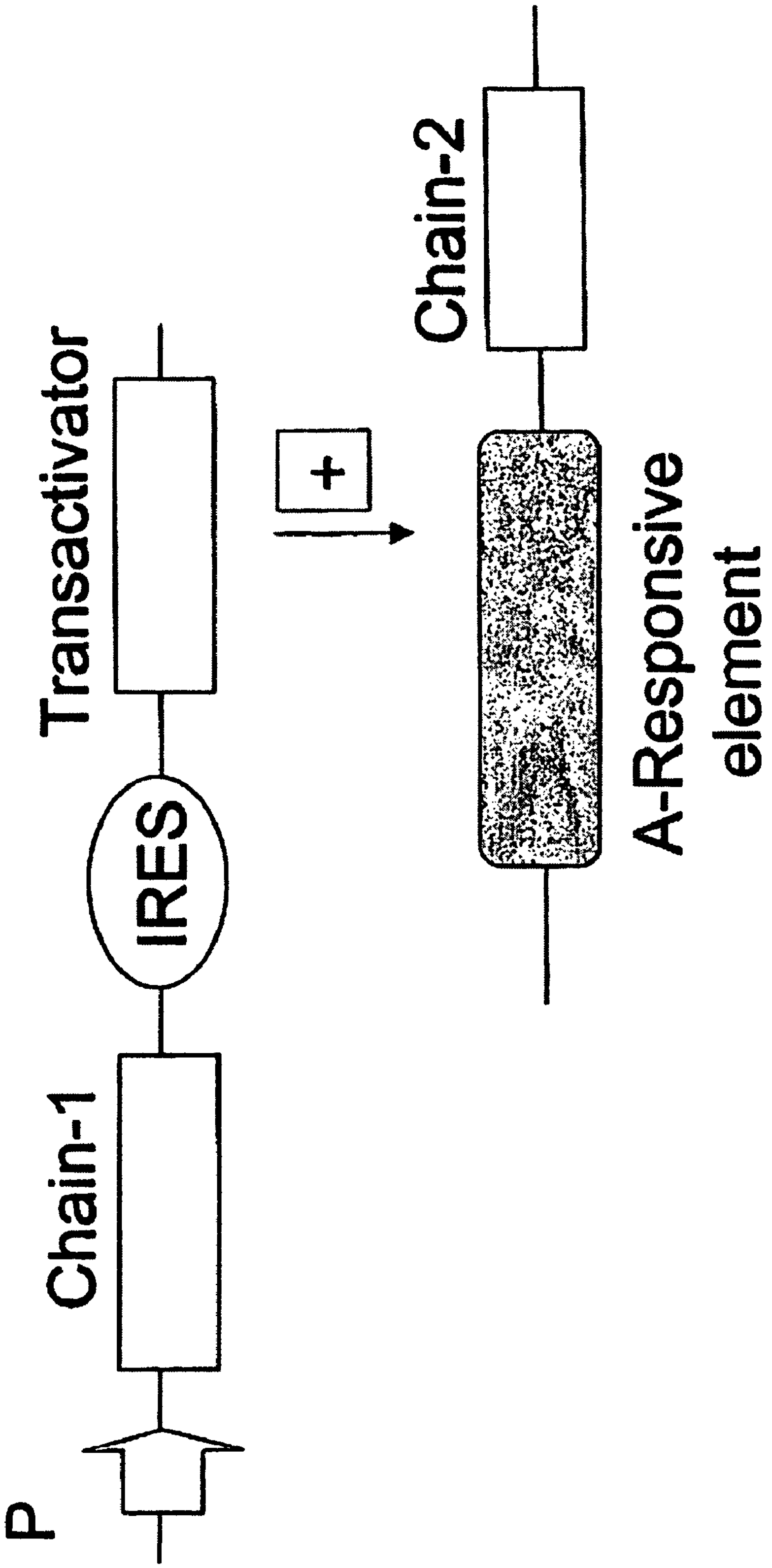
FIG. 12: Dependent expression of Ig chains. Chain-1 is typically the heavy chain, which is under control of a promoter (P). The IRES sequence links the expression of the heavy chain with that of a transactivator; this activates a responsive promoter to induce expression of Chain-2, typically the light chain (see text for details).

We describe here a method to directly relate the expression of the two partner variable regions that are required to pair in such manner that there is minimal waste (FIG. 12). The nucleic acid encoding the first variable region is cloned into an expression cassette, such that it will be under the control of a given promoter (typically the strong CMV promoter or other), and such that its coding sequence is followed by an Internal Ribosome Entry Site (IRES) and the coding sequence of the transactivator of the tet responsive element (TRE) fused to the activation domain of the herpes simplex VP16 protein (tTa). The nucleic acid encoding the second variable region is cloned into an expression cassette such that its expression is regulated via an inducible promoter, for example, the tet responsive element (TRE), existing of seven copies of the prokaryotic tetracycline operator site fused to a minimal CMV promoter. When introducing both expression cassettes into the same cell (on different vectors or on same vectors, at the same time or one before the other), the following relation between the expression of the two variable regions will exist: expression of the first variable region, which is under control of, for example, a constitutive promoter, will lead to the expression of the tTa protein. This protein activates the TRE-based promoter which will drive the expression of the second variable region. Thus, the production of the second variable region is now dependent on the production of the first variable region. If these regions are required to pair, the production of the individual components of the pairing can be made dependent.

When antibodies of the IgG-type are produced via a heavy and light chain, the production of the light chain can be made dependent on the production of the heavy chain. Consider the preferred embodiment, the production in the same host cell of a mixture of antibodies which all share a pairing-compatible light chain. The light chain gene is cloned under control of the TRE element, while the heavy chains are all provided with the IRES and tTa gene, as described above. In the host cell, every individual heavy chain that is expressed will then trigger the production of more partner light chain. This is important, because with multiple heavy chains being expressed, it is likely that the level of light chain may become limiting, and that the excess of unpaired heavy chain will induce possible toxicity in the host cell (as has been described for B-cells). This concept is also applicable to the embodiment described in section 4, for the selection of antigen-reactive antibodies from pools made in eukaryotic cells. Other promoter-transactivator systems have been described and are applicable in this concept also. In the same application field, in those cases where the ratios of two particular heavy chains need to be controlled or fixed, this method of dependent-expression may be used to link the expression of two heavy chains.

Figure 20:
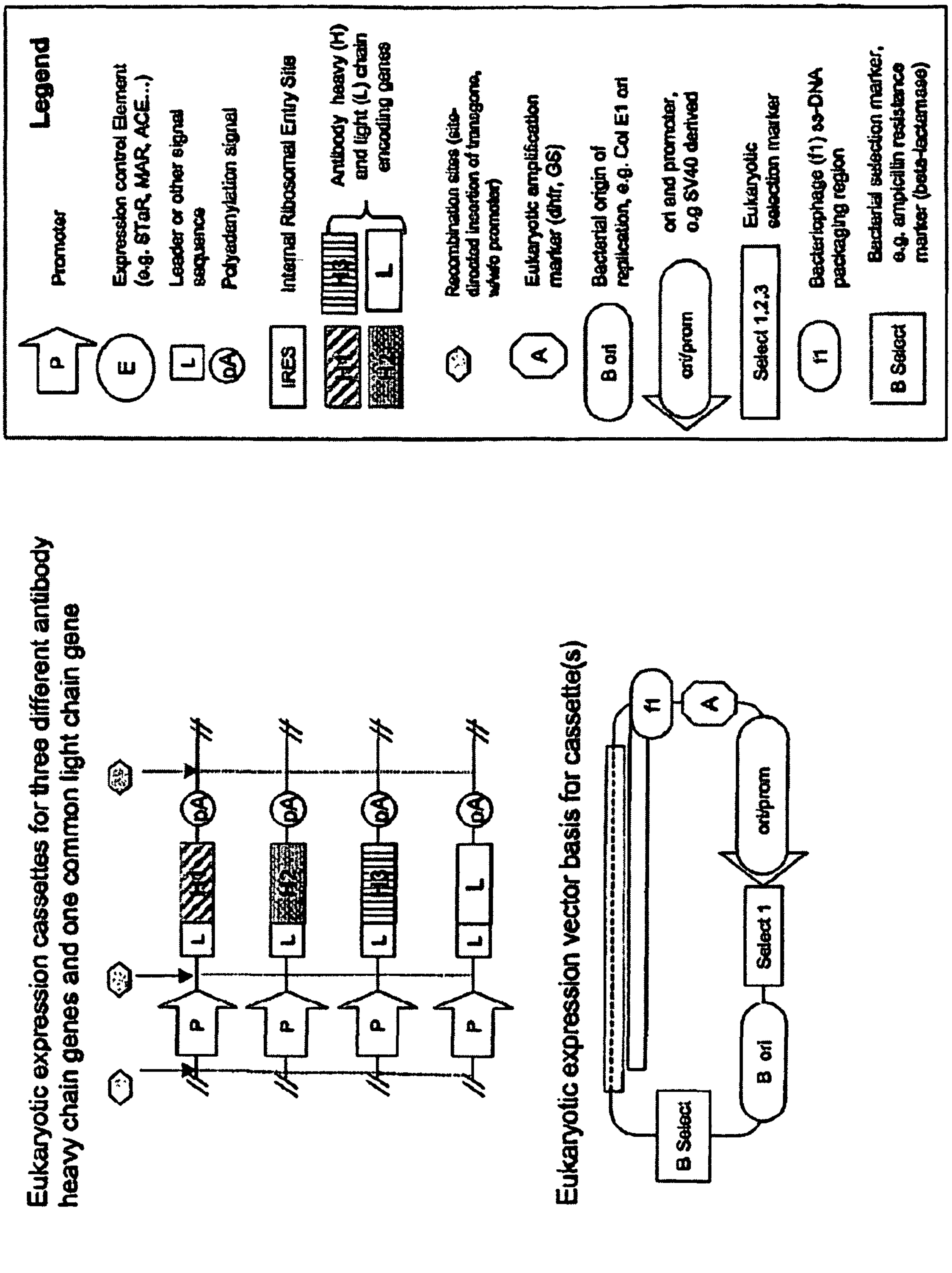
FIG. 20: Outline of the expression cassette and expression vectors for use with eukaryotic cells. The legend of the vector elements is depicted on the right. On the left hand side top panel are depicted, as examples, four eukaryotic expression cassettes for three antibody heavy chains and one light chain. The elements found in an expression cassette for a single antibody chain encoding gene or nucleic acid typically comprises a promoter, a Leader sequence, an open reading frame encoding the antibody chain of interest, a polyadenylation region and terminator, all in operable configuration. Further sites/regions used for site-directed and in some cases homologous, recombination, are shown (are also optional; indicated on top of the first expression cassette). On the bottom panel is depicted an exemplary vector backbone used for insertion of the top panel cassette(s). This scheme displays the typical elements of a eukaryotic expression vector, comprising a bacterial origin of replication (such as Col E1), a bacterial selection marker (B-Select, such as the ampicillin resistance gene), a eukaryotic selection marker (Select, such as gpt, neo, zeo, etc., see text; useful when stable integration into the host cell's genome is envisaged), and additional optional elements such as a bacteriophage packaging region (for ss-DNA production, such as f1), and an optional amplification marker (such as DHFR). Optional are other expression controlling elements (such as BEs, STAR, LCRs, MARs and the like, see below) and IRES; these are included in later figures.
Figure 21:
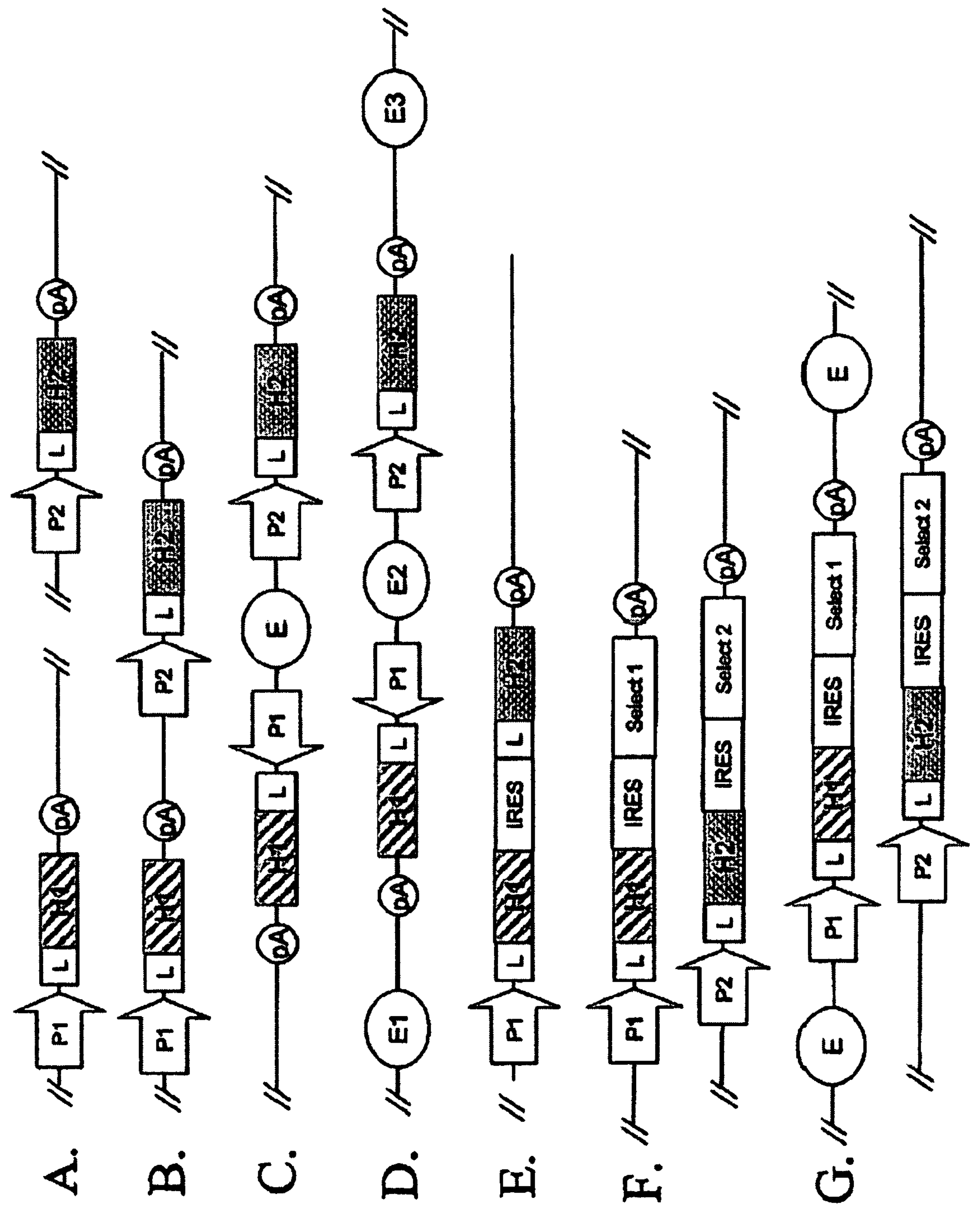
FIG. 21: Schemes depicting different formats for the co-expression of antibody chain encoding genes, exemplified here for the case in which two antibodies that share a common light chain (not shown) have to be co-expressed. (A) The basic individual cassettes, as separate cassettes and cloned into separate expression vectors. (B) This cassette contains the two Heavy chain (H) genes cloned in tandem, but their expression is individually regulated, via two different promoters, P1 and P2. (C) The two H genes are cloned into transcriptionally opposite directions and in this example separated by an element that influences the expression/stability/integration frequency (further examples are given in the text). (D) Same as B, but now additional E-elements are included at the 3' end of each of the two transcriptional units. (E) For cases in which two binding proteins should be present in the mixture at roughly similar quantities, an IRES is inserted between two H genes. (F and G) Expression cassettes for mediating the expression of two H chains, in which each of the H genes are linked via an IRES element to a selection marker (which is then selected for instead of using the vector-backbone-based marker), without (G) or with (H) additional elements in one cassette to influence expression.

Generally, a large number of suitable vectors and promoters are known to those of skill in the art and are commercially available for generating the recombinant constructs of the present invention. The following vectors are provided, by way of example, for the expression in eukaryotic cells of two or three antibodies that share a light chain sequence. The antibody chain encoding genes are cloned into expression cassettes that provide all regulatory and secretion signals which are typically used for antibody expression, as depicted in FIG. 20. In a first embodiment, the expression of multiple antibody heavy chains is made dependent on one another in the following way. In the first embodiment, the nucleic acid encoding the first heavy chain (H1) is cloned into an expression cassette, such that it will be under the control of a given promoter (typically the strong CMV promoter or other), and such that its coding sequence is followed by an Internal Ribosome Entry Site (IRES). This is immediately followed by a second antibody heavy chain coding region (H2, as depicted in FIG. 21). The P1 promoter will now drive the expression of H1 and H2, leading to an approximate 1:1 expression ratio between these two proteins; often though the second coding region is slightly less well expressed. Thus, if the expression ratio has to be steered towards a predefined range, the use of IRES sequences is particularly useful. This predefined range is influenced among other factors by the nature of the IRES sequence, and different IRES sequences will mediate different final ratios. Similarly, the expression ratio between three antibody heavy chains can be linked to one another by using a tricistronic expression cassette, in which the previous described cassette is followed by another IRES and Heavy chain coding region. Examples of tricistronic expression systems and of IRES sequences and configurations are described for other systems in the literature (Li et al., *J. Virol. Methods* 115:137.44; When et al., *Cancer Gene Therapy* 8:361-70; Burger et al. 1999, *Appl. Microbiol. Biotechnol.* 52:345-53). In these embodiments, the shared antibody light chain can be provided on a separate expression plasmid, on one or more of the vectors that carry on or multiple the antibody heavy chains, or can be already expressed by the host cell used for the transfection with the heavy chain expression vector or vectors.

In another embodiment, antibody heavy genes are sequentially transfected into the host cell. First we consider the embodiment for libraries of cells that produce mixes of two antibodies. Cells are transfected with the two antibody genes cloned into different vectors but the transfection is done sequentially in time. For example, the antibody heavy and light chain encoding regions of the first antibody are introduced into the host cell, and stable transfectants expressing this antibody identified and isolated. The antibody genes encoding a second antibody, in which the variable regions are pairing-compatible, are transfected into the host cell that already expresses the first antibody genes at high level. This procedure of carrying out sequential transfections (and if appropriate selections of integration in between) is also suitable for making collections of mixture with up to four to five different antibodies. To increase the number of cell clones expressing multiple antibodies, the vectors carrying the genes encoding the antibody genes, also carries a unique selection marker, such that transfected cells that have integrated the vector sequence can be readily selected and antibody expressing clones identified. As an alternative embodiment for making cells that express multiple antibodies with compatible pairing, the following procedure is used. First, as before, cell clone is produced that expresses one set of antibody chains (this can be one H and one L or multiple H and one L, for example) and is selected on the basis of a first selection marker. In parallel, a cell clone is produced that expresses another subset of antibody chains (for example, one or more other H and one L) and that is selected on the basis of a different selection marker (for example, neo, gpt, zeo, bdl, etc.). These cell clones are then fused and selected for the presence of both of the selective markers. Methods for cell fusion are extensively described in the literature and known to those working in the field; they are similar to those described in Norderhaug et al., 2002, *Eur. J. Biochem.* 269:3205-10.

The hybrid cells have the potential to express all of the antibody chains. Similarly, this procedure can be repeated if collections of larger numbers of antibody chains have to be made. Further, the use of cell populations rather than cell clones, in this sequential transfection or cell-fusion approach, provides a method for achieving large collections of cells that express the antibody chains at different ratios.

In one embodiment, the proteinaceous molecule's coding region or regions are flanked by sequences that mediate site-directed integration into the host cell genome (as depicted in FIG. 20). Without these, integration of transgenes occurs at random and, usually, several copies of the transgene are integrated at the same time, sometimes in the form of a head-to-tail tandem, with the site of integration and the number of copies integrated varying from one transfected cell to another. The use of recombination sites as depicted in FIG. 20 allows the precise site of integration to be targeted by homologous recombination between vector and host cell genome. This provides a means to insert the coding region into a site of high transcriptional activity, with the option to provide a promoter in the transgene or use the one that is present at the site of integration. With random or homologous recombination-mediated insertion of the antibody chain encoding nucleic acids is meant any insertion into the genome of the host cell, or into the nucleic acids in a subcellular organel, or into an artificial chromosome.

Preferred embodiments are to employ per expression vector used in the library construction not more than three antibody heavy chains coding regions and preferably two per vector. Preferably plasmids do not contain more than three promoters and three IRES sequences and not more than six STAR or MAR elements. It is preferred to limit the expression vector's size to 20 kb and if more binding sites than five are required in the mix, and these cannot be functionally encoded in a plasmid that is less than 20 kb in size, to use two or more different plasmids.

MARs and STARs can be positioned on either side of the DNA sequence to be transcribed. For example, the elements can be positioned about 200 by to about 1 kb, 5' from the promoter, and at least about 1 kb to 5 kb from the promoter, at the 3' end of the gene of interest. In addition, more than one element can be positioned 5' from the promoter or at the 3' end of the transgene. For example, two or more elements can be positioned 5' from the promoter. The element or elements at the 3' end of the transgene can be positioned at the 3' end of the gene of interest, or at the 5' end of a 3' regulatory sequence, e.g., a 3' untranslated region (UTR) or a 3' flanking sequence. Chromatin opening elements can be flanking on both ends of the expression cassette (FIG. 21D), or placed 5' of the expression cassette (FIG. 21C). In particular, when multiple regulatory elements such as STAR and UCOs have to be introduced into one and the same plasmids, preferably elements are used that have activity towards both ends of the element such that they can be provided in the middle of an expression cassette (FIG. 21C). Since MARs have also been reported to function when co-transfected in trans with the transgene (Zahn-Zabel et al. (2001) *J. Biotechnology* 87:29-42), they have the advantage that no DNA-cloning step is required to physically link them to SPCBP expression cassette(s). In that case size of the MAR element or of the expression vector carrying the SPCBP cassettes is no longer a limitation. Nevertheless, MAR elements as small as 1.3 kb have been described, thus multiple in cis inclusions are feasible. MARs have also been reported to be added both in cis and in trans, and in this configuration increase expression levels of antibodies in CHO cells 14-fold. One other function of these elements besides their effect on stability is that they will also increase the number of independently transformed cells that express the protein and promotes higher amounts of the recombinant protein. Clone isolation and production levels are overall higher, thus in a preferred embodiment, this invention is practiced by using these elements for making large collections of cell lines producing compositions comprising multiple functional binding sites.

8. Proteinaceous Mixtures with Multiple Effector Regions and Multiple Types of Binding Sites The invention can be used to create compositions of proteinaceous molecules that have multiple effector regions. In the case of antibodies, compositions are included that display one or more antigen binding regions in combination with two or more natural effector regions. Examples are the effector regions encoded by IgG1 and IgG4, which have, for example, different binding regions for C1q and the various Fc-receptors based within their encoding constant regions. Such mixtures may be clinically more effective than their mono-effector compounds: the mixture combines multiple and maximal natural effectors, which for various reasons are never present in the one natural antibody isotype, and the mixture thus mimics much more closely the natural pleiotropy of immune effectors that a single antigen/pathogen will evoke when our immune system encounters it. Some formats are IgG1 and IgG4, or IgG and IgM, or IgG1 and Fab, or IgG and IgA, or IgA and IgM, or IgG1-cytokine fusion and alike. Instead of making such proteins in different hosts, the co-expression of such different antibody formats, all associated with the same binding site (or possibly multiple binding sites but related to one target and preferable to one disease or indication), allows the direct production of cocktails of antibodies with different effectors. Such mixtures are more efficacious in their biological activity.

Besides antibodies, recent protein engineering techniques have allowed the production of binding sites with predetermined specificity using similar but also sometimes using very different structures. For example, antigen-specific ligands have been created using phage, bacterial, ribosomal or yeast display methods, from libraries of protein variants, in which the protein at some positions was variegated using random or oligonucleotide-based mutagenesis, but the main scaffold of the native protein maintained in the variants. Proteins for which has been already applied include the protein Z domain of Protein A, a variety of Kunitz domains, lipocalins, Green Fluorescent protein, one of the fibronectin domains, other domains of the immunoglobulin superfamily, and ankryns. Such antibody mimics are thus proteinaceous molecules with a non-natural binding activity, obtained, for example, by engineering into the molecule one or more residues or regions with variegated sequences, at either defined or random positions, and identifying the molecule with appropriate antigen binding properties by screening or selection processes. Examples of the processes are high-throughput screening for antigen binding by ELISA, or selection methods described in the literature such as in vitro display methods such as ribosome and puromycin display, cellular or viral display methods such as filamentous phage, lambda phage, bacterial, yeast, or eukaryotic cell display. The resulting proteinaceous molecules with the new binding site is an antibody mimic in the sense that it will contain a binding region for antigen at the position where it was initially a variable region, similar to an antibody molecule with two variable regions.

9. Making Compositions of Multiple Proteinaceous Compounds with Different Binding Specificities.

Recombinant DNA technology provides methods well known in the art to clone the variable region genes, and produce cell lines expressing the recombinant form of the antibody. In particular, the properties of antibodies are being exploited in order to design agents that bind to human target molecules, so-called “self-antigens,” and to antigens of viral or bacterial diseases. For example, a number of monospecific antibodies have been approved as human therapeutics. These include Orthoclone OKT3, which targets CD3 antigen; ReoPro, which targets glycoprotein IIb/IIIa; Rituxan, which targets CD20; Zenapax and Simulect, which target interleukin-2 receptors; Herceptin, which targets the HER2-receptor; Remicade and Humira, which target tumor necrosis factor; Synagis, which targets the F protein of respiratory syncytial virus; Mylotarg, which targets CD33; and Campath, which targets CD52.

For many clinical applications the efficacy of the treatment would increase if combinations of monoclonal antibodies are used. An oligoclonal preparation can be made by mixing individual recombinant antibodies which each have been made by conventional procedures, which includes the expression and purification of the individual recombinant or hybridoma-derived monoclonal antibodies, and the subsequent mixing of these molecules. The pharmaceutical development of separately produced and then mixed monoclonal antibodies is inhibitively expensive. Recombinant monoclonal antibodies of the IgG isotype are commonly made by co-expression of the nucleic acid sequences encoding the heavy and light chain of the antibody in the same host cell, yielding a monoclonal antibody, bearing two identical binding sites. The production of several antibodies from individual cell lines each making one antibody (and in which each cell line is controlled for stability of expression and consistency), is not economical with present biotechnological production methods.

One approach to combine monoclonals is to combine the binding sites in one molecule, hence creating a multispecific antibody. This allows the targeting of multiple epitopes on the same antigen, or of multiple antigens on the same target entity (e.g., a cell, a virus, a bacteria, an antigen), or of epitopes on different entities, providing a bridge between these entities. Of the multispecific antibodies, bispecific antibodies have been investigated the most, for targeting therapeutic or diagnostic entities to tumor cells, e.g., a cytotoxic T-cell, an NK cell, a chelator that carries a radionuclide. But in the bispecific antibody the two binding sites are always covalently coupled to one another, which limits the flexibility and use of such compounds. Further, many of the recombinant bispecific antibodies (e.g., Fab-scFv fusions, diabodies, double-single-chain Fvs) lack the provision of the antibody’s Fc region. Since Fc-dependent effector mechanisms such as ADCC are important for the efficacy of many antibodies (e.g., Rituxan and Herceptin), it will be important to maintain this region in the multispecific molecule.

The alternative approach is to use polyclonal antibodies comprising the entire immune response of a host to an immunogen. Polyclonals derived from the pooled serum from immunized animals or from selected humans have been used therapeutically e.g., for passive or active immunization, e.g., anti-rhesus D, anti-digoxin, anti-rabies, anti-snake venom polyclonals, and in some instances, work more effectively than a comparable monoclonal, e.g., Sangstat’s rabbit polyclonal against thymocytes versus Simulect™. Drawbacks for the use of polyclonal antibodies are the risk of infectious agents (viruses, prions, bacteria) in these often pooled preparations, but also the variability in efficacy, the limited availability, the immune response directed to the preparation if the polyclonal is non-human, and the abundance of non-relevant antibodies in these preparations. Polyclonals have also been made using recombinant methods, but again, the production of large arrays of antibodies from individual cell lines each making one antibody, is not economical with present biotechnological production methods. The production of the polyclonal antibody mixture by cultivating the many different cell lines in batch would be even more affected by differences in stability, growth and production rate, differences in purification yield, etc.

The present invention provides methods to produce mixtures of antibodies, preferably by expression from a single host cell, using antibodies with variable regions that appropriately pair with one another to yield essentially solely functional binding site combinations. The methods to obtain such antibodies were described earlier. The resulting variable regions can thus be co-expressed in biotechnologically viable and simple procedure, and a mixture of antibodies isolated using methods known in the art.

After selection of antibodies with the appropriate pairing behavior (such as antibodies with pairing-compatible variable regions, co-expression-compatible elements, etc., as described above), the antibody variable region genes are cloned into expression vectors that will direct the expression of an antigen binding fragment in, for example, the following format: Fab, Fab', Fab'2, IgG, IgM. In many instances the use of antibodies with, for example, pairing-compatible variable regions simplifies the DNA constructs that mediate the expression of the particular antibody format. For example, for the expression of two different antibodies as Fab'2 fragments in which one of the two antibody chains is the pairing-compatible variable region, only three antibody chains instead of the normal four have to be expressed to form two different binding sites. Such simplified expression constructs can lead to a more stable and more readily controlled expression system, and increase functional yields by minimizing problems associated with mispairing of heavy and light chain domains.

The mixture may contain a given selection of antibodies, recognizing epitopes on the same or different targets; examples are given below. A new application is the use of mixture containing antibodies specific for complexes formed by another antibody bound to a given target. Both of the antibodies can be provided in the mixture, providing a first antibody to bind the antigen, and a second one to “seal” the first interaction, providing the antibody mixture with an increase in overall affinity and specificity. Another embodiment of the invention is to use asymmetrically paired antibody molecules in the mixture such that the effector functions of the resulting mix are altered. The purpose of such mixing is to alter the properties of the effector mechanism of the individual antibodies in the mixture, in an antigen-specific/binding site directed manner, for example, the monospecific antibodies may each have a different effector from the bispecific components present in the mixture. Consider the next example, a mixture of two antibody binding sites formatted as Oligoclonics™ in the IgG-format, composed of the heavy chain gamma-1 heavy chain for one antibody variable region and the gamma-4 heavy chain for the other antibody variable region. The Oligoclonics™ mixture will contain the two monospecific antibodies, which will be either an IgG1 or an IgG4 isotype and display their respective effector functions, and also a hybrid dimer of gamma-1 and gamma-4, with altered or lost effector functions. Since many Fc receptors bind in an asymmetric manner to the symmetrically arranged Fc region, asymmetric Fc regions often will loose interactions with Fc receptors and thus ADCC or other activity. Mutants of Fc regions with, for example, mutations in the Fcgamma-Receptor motif (residues 233-238 in the CH2-lower hinge region), or mutants with reduced C1q binding, or mutants with exchanged or shortened hinge, or with domains exchanged by other domains of the immunoglobulin heavy chain family, or Fc regions optimized for their interaction with particular Fc regions (e.g., improved binding to the activating receptor FcgammaRIII and/or decreased binding to the inhibitory receptor FcgammaRIIb), can also be used for the assembly of such asymmetric Fc regions. Applications of such asymmetric pairs are provided in a mixture of one compound but not others with a particular effector function, or to remove an effector, for example, in the bispecific or monospecific compounds.

10. Examples of Uses of Compositions of Multiple Proteinaceous Compounds with Different Binding Specificities There are applications for mixtures of different binding sites on the same antigen, for mixtures of different binding sites on different antigens, for mixtures of different binding sites on different antigens on the same or different target. As an example of use of a mixture in the treatment of a viral disease, the example of Hepatitis B virus (HBV) infection is discussed. Recombinant HBV vaccines provide a safe and effective means for prevention of HBV conferring long-term immunity through active immunization. In contrast to the slow onset of protection following this vaccination, passive immunotherapy with antibodies to HBV provides immediate but short-term protection against viral transmission and infection. Antibodies are believed to inhibit infection by blocking HBV from entering into cells. Such passive immunotherapy is advisable for individuals who were exposed to HBV-positive material (needle or cut injuries) and for newborns to mothers who are HBV carriers, for patients undergoing liver transplantation. At present, such treatment is carried out with Hepatitis B immunoglobulin, a plasma derived, polyclonal antibody preparation obtained from donors who were anti-hepatitis B surface antigen antibody-positive. The availability of this serum is limited and further pricing and safety concerns regarding the use of blood products, make the development of an alternative treatment necessary. A human monoclonal antibody would be advantageous by presenting a stable and reproducible source for prolonged immunotherapy. However, studies show that a monoclonal antibody directed to the S antigen and neutralizing capacity against HBV in chimpanzees delayed but not prevented the infection with HBV. In part this may be caused by the emergence of escape variants, mutants in the S-antigen that can no longer be bound by the monoclonal antibody. Similarly, escape mutants arise in patients after liver transplantation in clinical trials with monoclonal antibodies. Therefore, treatment with a single monoclonal antibody may be inefficacious and insufficient. Follow-up studies have involved mixtures of human monoclonal antibodies. Studies carried out by XTL Biopharmaceuticals and colleagues show that a mixture of two antibodies is more effective in reducing viral load and inhibiting HBV infection in animal model systems than a polyclonal mixture. This indicates that the potency of a polyclonal humoral immune response can be deconvoluted to a few antibodies, and that a defined mixture of a few antibodies should work as well or better than some polyclonal preparations. A mixture of two antibodies recognizing different epitopes on the viral surface was thus shown to be more effective in the prevention of HBV reinfection.

In another example of use of a mixture of monoclonal antibodies in the treatment of a viral disease, the example of the Human Immunodeficiency Virus type-1 (HIV-1) is discussed. Infection with HIV-1 will lead to the development of the Acquired Immunodeficiency Syndrome (AIDS) if left untreated. During infection with HIV-1, neutralizing antibodies that are directed against diverse epitopes on the HIV-1 envelope glycoprotein molecules gp41 and gp120 develop. In a clinical trial published in 1992, the administration of HW-1 seropositive plasma containing high titers of HIV-neutralizing antibodies, was associated with a reduction in HIV-1 viremia and a number of opportunistic infections. Several groups have subsequently published that administration of HIV-1 seropositive plasma results in delay of the first AIDS-defining event and improvement of clinical symptoms. However, enthusiasm for passive immunotherapy declined when it was found that antibodies failed to eliminate the virus and resulted in the emergence of neutralization escape variants in patients. It was demonstrated that the antibodies that are induced during natural HIV-1 infection poorly neutralize the virus, resulting in a low potency of hyperimmune sera used for passive immunotherapy of HIV-1 infection. In addition, it was demonstrated that some antibodies that arise during natural infection can even enhance the infection. It was realized that for antibody therapy of HIV-1, potent and well-characterized neutralizing monoclonal antibodies were needed.

These early findings spurred the development of human monoclonal antibodies against HIV-1 envelope glycoproteins. In recent years, a number of human monoclonal antibodies against the HIV-1 gp41 and gp120 viral coat glycoproteins have been isolated and characterized for their virus-neutralizing activity in vitro. Subsequent experiments in non-human primate models of HIV infection and transmission have shown that human monoclonal antibodies targeting different HIV-1 envelope glycoprotein epitopes exhibit strong synergy when used in combination. It has been suggested that combinations of human anti-HIV monoclonal antibodies can be exploited clinically for passive immunoprophylaxis against HIV-1.

The third example relates to the Rabies field. Rabies is an acute, neurological disease caused by the infection of the central nervous system with rabies virus, a member of the *Lyssavirus* genus of the family of Rhabdoviridae. Almost invariably fatal once clinical symptoms appear, rabies virus continues to be an important threat to human and veterinary infection because of the extensive reservoirs in diverse species of wildlife. Throughout the world, distinct variants of rabies virus are endemic, in particular, terrestrial animal species, with relatively little in common between them. Rabies virus is characteristically bullet-shaped, enveloped virion of single-stranded-negative sense RNA genome and five structural proteins. Of these, a suitable target for neutralization is the viral glycoprotein (G). Antigenic determinants on G vary substantially among the rabies virus strains. Prompt treatment after infection consists of passive and active immunotherapy. For passive immunotherapy mostly pooled serum of rabies immune individuals or immunized horses is used, but with a risk of contamination with known or unknown human pathogens, or the risk of anaphylactic reactions, respectively. In addition, anti-rabies immunoglobulin is expensive and may be either in short supply or non-existent in most developing countries where canine rabies is endemic. There is, therefore, a need for compositions and methods for producing mixes of antibodies, preferably human antibodies, to use in passive immunotherapy of Rabies infections. A number of human monoclonal antibodies made by fusion of Epstein-Barr Virus transformed, rabies-virus-specific human heterohybridomas have been made (Champion et al., *J. Immunol. Methods* (2000) 235:81-90). A number of virus-neutralizing antibodies derived from these antibodies have also been cloned (PCT/IS02/26584 and PCR/US01/14468 and Morimoto et al. (2001), *J. Immunol. Methods* 252:199-206). Several other rabies-neutralizing monoclonal antibodies have been described in the art, which could also be used in the experiments below. As indicated in these publications, a mix of different rabies-neutralizing human antibodies would be an ideal reagent for passive immunotherapy of Rabies.

In general for viral diseases, the functional assembly of mixes of anti-viral antibodies may increase the clinical efficacy of the treatment when compared to monoclonal therapy, by decreasing the probability of viral escape mutants resistant to treatment, and by reducing the likelihood of viral resistance with prolonged therapy. In the mixture, antibodies may be included that bind to many different epitopes of the virus. It may also be feasible to include antibodies to different subtypes of the virus, to broaden the utility of the drug for a wider patient population. Further anti-viral antibodies directed to linear epitopes may be added, which may be less prone to the effect of escape mutants than conformation-dependent antibodies. The effect of multiple binding specificities present in the antibody mix can provide a stronger signal for viral clearance than when a monoclonal antibody is used. There are also applications for mixtures of essentially one binding site with different fine-specificities for binding its antigen. For example, when the antigen is prone to mutation as is the case with many viral antigens, in the course of a treatment the epitope on the antigen may be altered such that the binding of the original antibody is lost. When using a mixture, e.g., based on the same heavy chain paired with a small set of light chains that provide a range of fine-specificities, there is a possibility that the mutations will affect the binding of some species in the mixture, but not of others with a different binding chemistry mediated by the pairing-compatible variable region. In such a case it will be preferable to use distinct binding chemistries for the interaction with the antigen, thus the pairing-compatible variable regions should be as unrelated as possible in sequence. Alternatively, antibodies can be used that use very different binding site chemistries by having unrelated heavy and light chain variable regions, but display exclusively pairing behavior such that their production in the same cell yields mainly functional binding sites. Such mixtures are preferably more active than the individual components, and in some case will act synergistically.

In the Oligoclonics™ format, antibodies of the IgG isotype are made by co-expression of the light and heavy chain genes with appropriate pairing behavior in the same host cell. The result of this process is a mixture of different proteins, the monospecific bivalent antibodies which carry two identical binding sites, and bispecific antibodies, carrying two different binding sites. There will be occasions where the presence of this bispecific antibody class will further enhance the efficacy of the antibody mixture. Only when there are multiple epitopes present on the antigen or microorganism, and these epitopes are presented in the correct positioning, will a monoclonal antibody of the IgG isotype, for example, be able to bind both of its binding Fab-arms to the antigen. In many instances where the antigen is a monomer or a small multimer, like cytokines, interleukins and interferons, mostly only one arm of a monoclonal IgG antibody will be binding the antigen. The bispecific component of the Oligoclonics™, provides a new opportunity to bridge neighboring epitopes, and form a highly avid binding antibody. Pairs that have this behavior may be selected using the methodologies of screening mixtures of antibodies as disclosed herein. Besides this avidity advantage, bispecific molecules may also cross-link receptors that mono-specific yet bivalent antibodies in the same mixture cannot cross-link. Oligoclonics™ may thus provide an antibody mixture that per unit of mass will more effectively neutralize viruses, cytokines, toxins etc when compared to monoclonal antibodies, and in specific cases, for example, with an avidly binding bispecific component or receptor-cross-linking or other unique mechanism mediated by the bispecific antibody, also compared to mixtures of monoclonal antibodies. The bispecific compounds are also useful to explore routes traditionally developed with bispecific antibodies, such as the retargeting of immune effector molecules or cells such as T-cells, complement proteins and Fc-receptor expressing cells to tumor cells or pathogens.

Thus, mixtures of antibodies may be suitable to fight pathogens including viruses like HIV and Rabies, bacteria, fungi and parasites. Other examples where a polyclonal serum or gammaglobulin is currently used that could be replaced with a defined antibody mixture, include such diseases as rabies, hepatitis, varicella-zoster virus, herpes or rubella. Bacterial diseases that could be treated with antibody mixtures include Meningitis, diseases caused by *Staphylococcus, Streptococcus, Hemophilus, Nesseria, Pseudomonas* and the *actinomycetes*. Targets may also include those involved in bacterial sepsis such as lipopolysaccharide (LPS), lipid A, tumor necrosis factor alpha or LPS-binding proteins. Some of these pathogens occur in multiple serotypes and not one but multiple antibodies are required to neutralize the various serotypes. A mixture of antibodies will provide, by the choice of the binding specificities, a wider coverage of serotypes that may be treated and, therefore, more patients can be treated with the same antibody mixture. The mixtures for this and other reason can form also suitable diagnostics and part of diagnostic kits for the detection of a disease or disorder in patient.

Mixtures of antibodies may be more effective than monoclonal antibodies also in the treatment of oncological diseases such as non-Hodgkin's lymphoma (NHL) and epithelial cell tumors like breast and colon carcinoma. Targeting both CD20 and CD22 on NHL with antibodies has already been proven to be more effective than targeting the tumor cells with the individual antibodies. Suitable target antigens for antibody mixtures in oncological diseases are many, including CD19, CD20, CD22, CD25 (IL-2 receptor), CD33, the IL-4 receptor, EGF-receptor, mutant EGF receptor, Carcino-Embryonic Antigen, Prostate-specificAntigen, ErbB2IHER2, Lewis$^{y}$ carbohydrate, Mesothelin, Mucin-1, the transferrin receptor, Prostate-specificMembrane Antigen, VEGF and receptors, EpCAM and CTLA-4. Synergistic effects may be seen when using antibodies that bind different targets and pathways in the disease, such as antibodies with anti-angiogenesis and anti-proliferative effects. There are also applications in this field for a mixture of essentially one binding site with different affinities for binding its antigen. For example, the efficiency of in vivo solid tumor penetration is limited for high affinity antibodies due to the binding site barrier, yet a minimal affinity is required to achieve a substantial accumulation in the tumor. With the methods described in this document, a mixture of antibodies can be established, e.g., based on the same heavy chain paired with a small set of light chains yet appropriate pairing behavior that provide a range of affinities when paired with the heavy chain. Such mixtures can be used to increase the accumulation in the tumor, and the best balanced cocktail found by choosing the components and their expression levels. Such mixtures are preferably more active than the individual components, and may act synergistically.

Mixtures of antibodies may also be suitable to neutralize multiple different targets, for example, in the field of inflammatory diseases, where multiple factors are involved one way or another in mediating the disease or aggravating its symptoms. Examples of these diseases are rheumatoid arthritis, Crohn's disease, multiple sclerosis, insulin-dependent diabetes, mellitus and psoriasis. Optimal treatment of many of these diseases involves the neutralization or inhibition of circulating pathological agents and/or those on the surface on cells targeted in the specific inflammatory response in the patient. In autoimmunity and inflammatory diseases suitable targets are generally interferons, cytokines, interleukins, chemokines and specific markers on cells of the immune system, and, in particular, alpha interferon, alpha interferon receptor, gamma interferon, gamma interferon receptor, tumor necrosis factor alpha, tumor necrosis factor receptor, HLA-class II antigen receptor, interleukin-1beta, interleukin-1beta receptor, interleukin-6, interleukin-6 receptor, interleukin-15, interleukin-15 receptor, IgE or its receptor, CD4, CD2, and ICAM-1.

Mixtures are also suitable for the neutralization of effects mediated by agents of biological warfare, including toxins such as *Clostridium botulinum* derived botulinum neurotoxin, Anthrax, smallpox, hemorrhagic fever viruses and the plague. The neutralization of the botulinum toxins is discussed here as an example. The botulinum toxins, the most poisonous substances known, cause the paralytic human disease botulism and are one of the high-risk threat agents of bioterrorism. Toxin-neutralizing antibody can be used for pre- or post-exposure prophylaxis or for treatment. Small quantities of both equine antitoxin and human botulinum immune globulin exist and are currently used to treat adult and infant botulism. Recombinant monoclonal antibody could provide an unlimited supply of antitoxin free of infectious disease risk and not requiring human donors for plasmapheresis. A panel of human and murine monoclonal antibodies was generated from the B lymphocytes of hyperimmune donors and immunized mice using phage antibody display technology. Single monoclonal antibodies and combinations were tested for their capacity to protect mice from lethal doses of neurotoxin (A. Nowakowski et al. (2002) *PNAS* 99:11346-11350.). Whereas single monoclonal antibodies showed no significant protection of the mice against lethal doses of toxin, combinations of only three monoclonal antibodies against different epitopes on the toxin gave very potent protection. The combination of three monoclonal antibodies neutralized 450,000 lethal doses of botulinum toxin, a potency 90 times greater then human hyperimmune globulin. Importantly, the potency of the monoclonal antibody mixture was primarily due to a large increase in functional antibody-binding affinity. Thus, methods that allow the cost-effective, controlled and efficient production of mixtures of monoclonal antibodies against botulinum neurotoxin provide a route to the treatment and prevention of botulism and other pathogens and biologic threat agents. As shown in this study, a mix of three antibodies that bound non-overlapping epitopes on botulinum neurotoxin, had a synergistic effect on toxin neutralization due to a increased overall avidity.

Mixtures of antibodies may be further applied to delay the onset of anti-idiotype responses in patients, by providing multiple idiotypes of an antibody family, all binding to the same target, in the simplest form amino acid mutants of the same antibody with a resulting similar binding specificity and affinity, to a more complex mixture of multiple antibodies directed to the same epitope.

Mixtures of antibodies can also be applied to develop derivatives of the protein mixtures, including immunotoxins, immunoliposomes, radio-isotope labeled versions, immunoconjugates, antibody-enzyme conjugates for prodrug-therapy (ADEPT), and immunopolymers (Allen, (2002) *Nat. Rev. Cancer* 2:750-783). The mixes of the antibodies can either be modified in batch with the appropriate substances, or may be genetically fused to a toxin or enzyme encoding gene as described in the art for monoclonal antibodies.

Having generally described the invention, the same will be more readily understood by reference to the following examples, which are provided by way of illustration and are not intended as limiting.

EXAMPLES

Example 1

Description of the Hybridoma-Derived Anti-Rabies Antibodies Used in the Studies This example describes a number of rabies-neutralizing antibodies that are used in the further examples. The following antibodies are virus-neutralizing human antibodies: (1) JB1 (abbreviated to JB in the next section), described in Champion et al., *J. Immunol. Methods* (2000) 235:81-90, and the cloning and sequence in PCT/IS02/26584; (2) JA-3.3A5 (abbreviated to JA in the next section), described in Champion et al., *J. Immunol. Methods* (2000) 235:81-90, the cloning in Morimoto et al. (2001), *J. Immunol. Methods* 252:199-206 and also in PCT/US01/14468; (3) M57, antibody and its cloning were described in Cheung et al. (1992), *J. Virol.* 66:6714-6720, and further in PCT/IS02/26584. The nucleotide sequences of the full heavy and light chain nucleotide sequences and also amino acid sequences of their variable regions are disclosed in the sequence listings (SEQ ID NOS: 1-12). On the basis of the data in the literature these antibodies all neutralize a variety or rabies isolates, but not all the same, providing a broader spectrum of neutralized isolates than when using a monoclonal.

Example 2

Production of Mixtures of scFv Antibody Fragments Based on Recloned Hybridoma-Derived Anti-Rabies Antibodies and Co-Expression This example describes the production of a mixture of three binding sites as three proteins. Using as template the variable region genes of the three antibodies described in Example 1, cloning is used to construct three single-chain Fv expression cassettes, one for each of the antibodies, and to clone these in an appropriate expression vector.

First the variable region genes are amplified with oligonucleotides that hybridize to the 5' and 3' ends of the nucleotide sequences and provide appropriate restriction enzyme sites for cloning. Standard cloning techniques are described in Sambrook et al., *Molecular cloning*, second edition, Cold Spring Harbor Laboratory Press (1987). Cloned variable regions genes are amplified by the polymerase chain reaction using methods well known in the art. For antibody JA, the following procedure is used: primers are designed in the FR1 region and in the FR4 region of the variable heavy chain nucleotide sequence, such that the variable region is cloned downstream of a bacterial leader sequence and upstream of a continuation of the reading frame with a Gly-Ser encoding sequence. The polylinker into which the variable region heavy and light chains are cloned is indicated in FIG. 13. The primers are designed to maintain the amino-terminal sequence of the FR1 and FR4 regions, and to include a unique restriction enzyme site for cloning of the variable region into the polylinker region of pSCFV (FIG. 13). pSCFV is a pUC119 derivate which is essentially pHEN 1 (Hoogenboom et al. (1991) *Nucl. Acids Res.* 19:4133-4137) into which the SfiI-NotI fragment is replaced with the SfiI-NotI sequence depicted in FIG. 13, and in which the NotI site is followed by a c-myc tag, for detection and purification of the antibody fragment. Also the geneIII of filamentous phage is deleted in this plasmid. Several options for directional cloning are feasible, indicated by the restriction sites locations on the polylinker map on FIG. 13. For the VH of JA, the following oligonucleotides are used to amplify the VH regions: 5'-GTC CTC GCA ACT GCG GCC CAG CCG GCC ATG GCA GAG GTG CAG CTG TTG GAG TCT GGG GG-3' (SEQ ID NO:18) and the reverse complement of 5'-ACC CGG GTC ACC GTC TCC TCC-3' (SEQ ID NO:19). The PCR reaction is carried out with the template antibody gene which was already cloned, plasmid SPBN-H (Morimoto et al. (2001), *J. Immunol. Methods* 252:199-206), for 25 cycles, denaturation at 94° C. for 30 seconds, annealing at 50° C. for 60 seconds, and elongation at 72° C. for 90 seconds, using Taq DNA polymerase (Promega, Madison, Wis.). The resulting product of approximately 400 by is purified, digested with the restriction enzymes SfiI and BstEII, and cloned into pSCFV, resulting in pJA-VH. Similarly, the light chain of JA is amplified from pSPBN-L with appropriately designed oligonucleotides and is cloned into pJA-VH, to yield pSCFV-JA. The integrity of the sequences is confirmed by using the AmpliTaqs cycle sequencing kit (Perkin-Elmer, Foster City, US) with specific primers based in the vector backbone just adjacent to the variable region inserts. Similarly, the antibody variable regions from hybridomas JB and M57 are cloned into the single-chain Fv format.

The expression of the individual antibody fragments is done as follows. Soluble scFv fragments are expressed upon induction with isopropyl-β-D-thiogalactopyranoside (IPTG) from the lacZ promoter that drives the expression of the scFv in pSCFV-based plasmids, and harvested from the periplasmic space of *E. coli* TG1 cells. To confirm binding of the individual scFvs, an ELISA is performed using Polysorb plates (Nunc) coated with 5 micrograms/ml of rabies virus glycoprotein. Virus purification and glycoprotein purification have been described elsewhere (Dietzschold et al. (1996) *Laboratory Techniques in Rabies*, Eds Meslin, Kaplan and Korpowski), World Health Organization, Geneva, p. 175). Alternatively, a source of recombinant Rabies Glycoprotein (G) of the appropriate type is used for the coating. The sequence of rabies G is available to the person skilled in the art and so are cloning, expression and purification techniques.

Figure 14A:
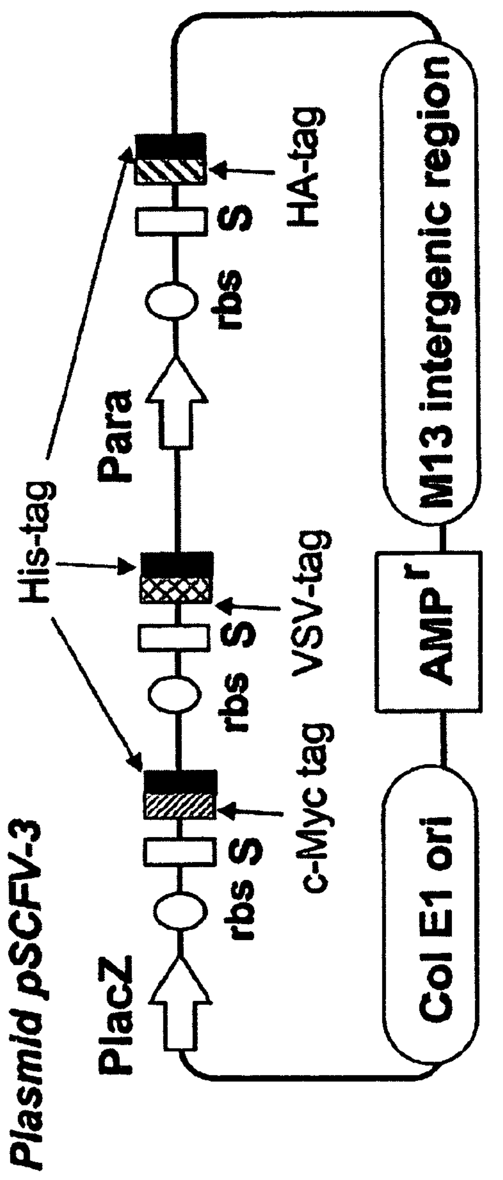
FIG. 14: Schematic depiction of plasmid pSCFV-3 (A) and pSCFV-3 with three cloned scFv fragments, in this case derived from the antibodies JA, JB and M57. The black box is a schematic depiction of the histidine stretch; other C-terminal-based tags are also indicated. S, signal sequence; rbs, ribosome binding site; AMPr, ampicillin resistance gene (beta-lactamase).

In the next step, the scFv expression cassettes are cloned one after another in plasmid pSCFV-3 (depicted in FIG. 14A), which is a derivative of pSCFV carrying unique restriction sites for cloning scFv genes, two behind the same lacZ promoter and separated via a new ribosome-binding site (rbs) and signal sequence (S), and one behind an arabinose-inducible promoter, rbs and S (FIG. 14A). It also carries different tags, one for each of the scFv cassettes, c-myc (as in pSCFV; sequence EQKLISEEDL (SEQ ID NO:20)), the VSV-tag (the sequence YTDIEMNRLGK (SEQ ID NO:21)) and the influenza Hemagglutinin (HA)-tag (the sequence YPYDVPDYA (SEQ ID NO:22)), and all followed by a stretch of three alanines and five histidines. This set-up provides a method for detection of the individual antibodies in the mix, and a generic method for purification, based on immobilized metal affinity chromatography (IMAC) using methods well known in the art. The plasmid is also used in Example 17 (with restriction inserts and cloning sites described in SEQ ID NOS:16 and 17). The scFv genes are amplified with oligonucleotides that introduce the appropriate sites, and cloned into this plasmid.

Figure 14B:
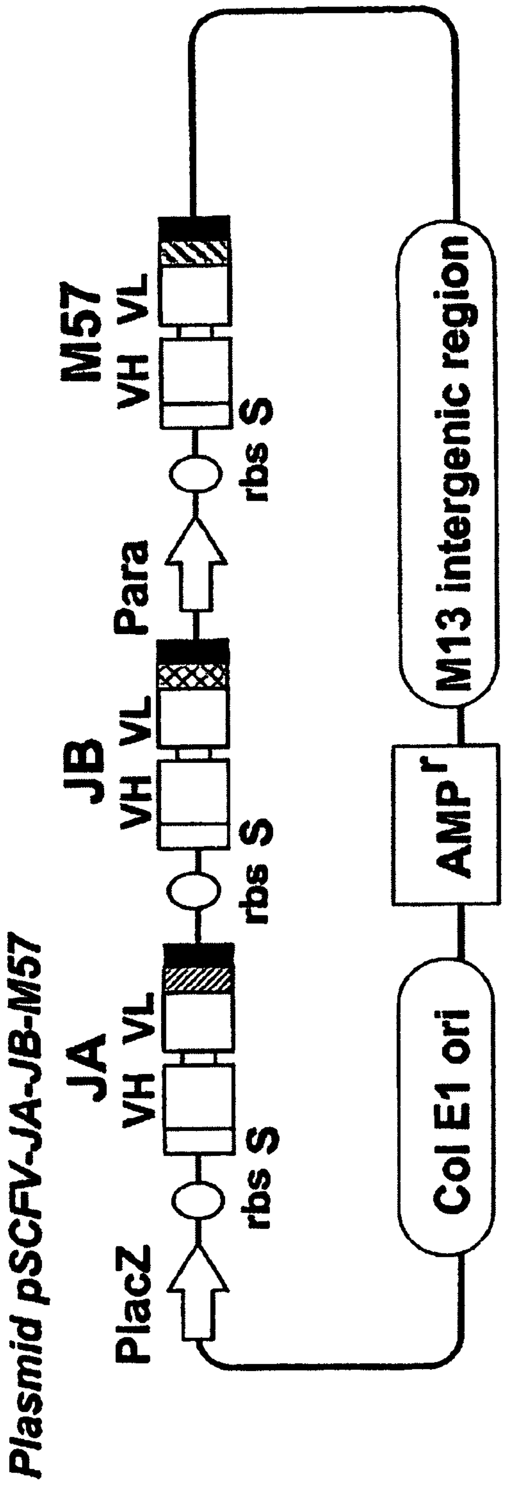

The finally resulting plasmid, pSCFV-JA-JB-M57 (FIG. 14B) is introduced into *E. coli* host TG1 cell, and expression of the scFvs induced with IPTG (for JA and JB) and/or arabinose (M57). By induction with IPTG, the expression of a mixture of two functional scFv fragments is achieved, in which the direct linkage favors the pairing between the intramolecularly linked variable regions. By further induction with arabinose, an additional scFv fragment is co-expressed. Alternatively, the three scFv expression cassettes are cloned in separate plasmids into compatible plasmids such as pBR322 and pACYC and maintained in the same host cell before induction. The binding of the mixture to rabies glycoprotein (G) is tested as before using ELISA. The contribution to the binding in the mix of each of the scFv fragments is confirmed using one of three anti-tag antibodies (the mouse monoclonal antibody 9E10 binding to human c-Myc epitope tag (product code from abcam, www.abcam.com: ab32), and polyclonal antibodies to the HA-tag (ab3413) or VSV-tag (ab3556). To verify whether the production is carried out by one bacterium and its progeny and not by three clones that each produce one of the antibody fragments, the culture is colony-purified after four hours in the induction phase and the production tested of three independent clones, confirming that the expression is clonal. To determine the percentage of correctly paired variable regions, the scFv mixture is first purified from the *E. coli* periplasmic extract using IMAC. Briefly, an IPTG and arabinose-induced 500 ml culture (kept for four hours at 30° C.), is spun at 4600×g for 20 minutes at 4° C., and the bacterial pellet resuspended in phosphate buffered saline (PBS) containing protease inhibitors (phenyl-methyl-sulfonyl fluoride and benzamidin). The solution is sonicated at 24° C. using an ultrasonic desintegrator (MSE Scientific Instruments), and the suspension centrifuged at 50,000×g for 30 minutes at 4° C. The supernatant fraction is incubated with TALON™ resin according to the instructions of the manufacturer (Clontech). After extensive washing, proteins are eluted using 100 mM imidazole. Following this procedure, scFv fragments are further purified by gel filtration using a Superdex 75 column (Amersham Pharmacia Biotech) connected to a Biologic instrument (Biorad). ScFv concentrations are quantitated using the bicinchoninic acid kit (Pierce). A fraction of the antibody mix is bound to a molar excess of biotinylated G protein in a 0.5 ml volume. The protein with bound scFvs is captured onto the surface of an excess of paramagnetic Streptavidin-coated beads (200 microliters of DYNAbeads, Dynal, Norway), in a way similar to what is described in Example 4 for phage selections. The supernatants of the mixture are then tested for the presence of scFv fragments in an SDS PAGE followed by Western blot analysis with the anti-tag antibodies to characterize the non-functional antibodies. The experiment provides evidence for the simultaneous production of three scFv fragments by the same host cell, and the efficient recovery of functional binding sites, thus correctly paired variable regions from this preparation.

Example 3

Figure 15:
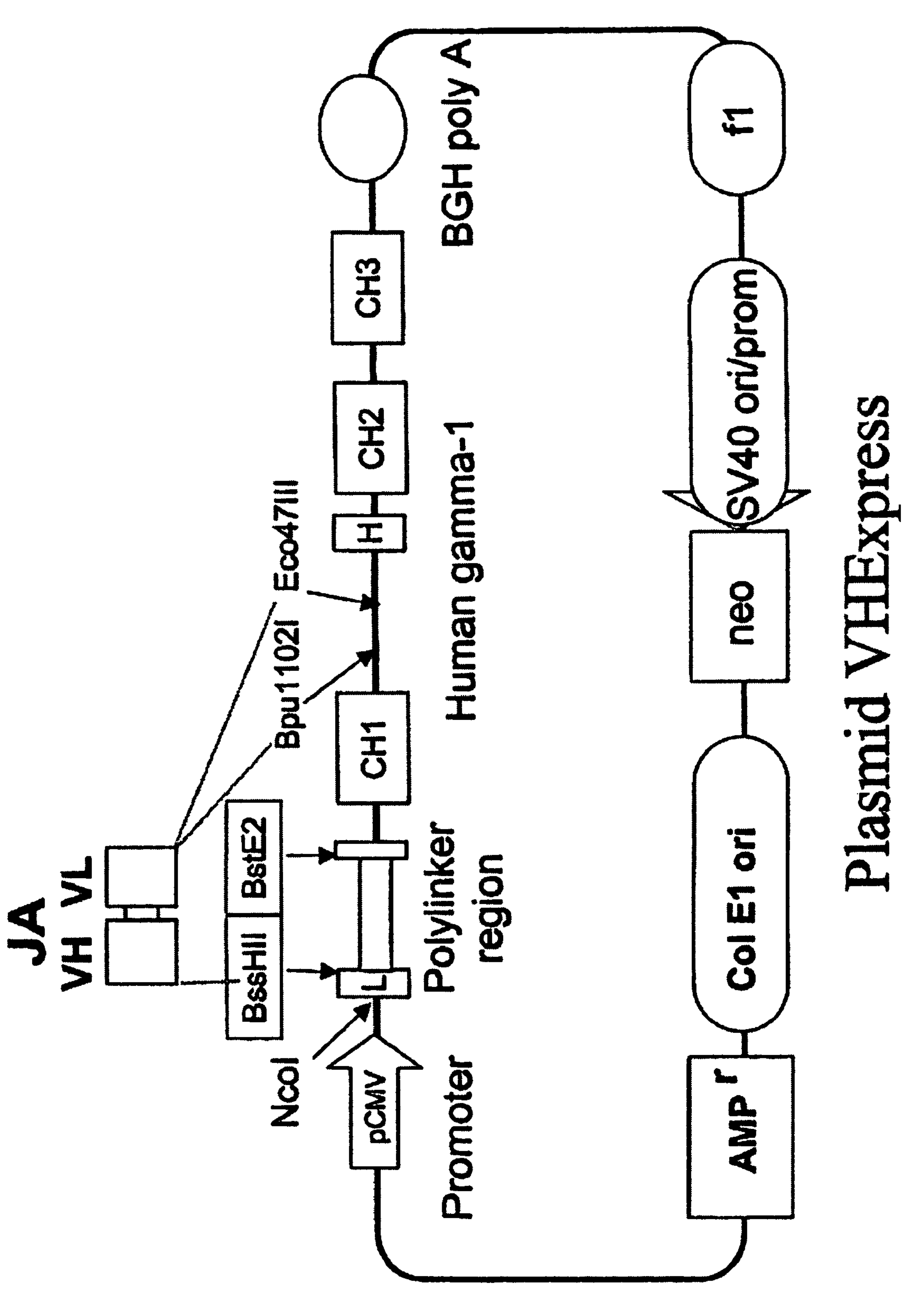
FIG. 15: Schematic depiction of the eukaryotic expression vector VHExpress as also described in (Persic et al. (1997) 187:9-18) except that this variant has a CMV promoter; its use for cloning scFv fragments (top, indicated for antibody JA) such that the expression of scFv-Fc fusions is achieved.

Production of Mixtures of scFv-Fc Antibodies Based on Recloned Hybridoma-Derived Anti-Rabies Antibodies and Co-Expression in a Eukaryotic System This example describes the production of a mixture of three or six different proteins composed of variable regions paired to form two or three binding specificities. In a further example, the scFv genes are subcloned into a eukaryotic expression vector based on pcDNA3 which carries the human gamma-1 region. This plasmid, VHExpress, was extensively engineered to remove internal restriction enzyme sites (Persic et al. (1997) 187:9-18), and contains a promoter (CMV instead of EF-1alpha as in publication), a eukaryotic leader sequence, a polylinker with cloning sites for an antibody variable region, the human gamma-1 gene and the bovine growth hormone poly A site (FIG. 15). Further it contains the genes encoding amp and neo resistance, and the SV40 origin of replication. The full sequence is given in SEQ ID NO:13. This vector is suitable for the expression of antibody variable region genes formatted as scFv fragments. The cloning of the scFv gene of antibody JA is carried out as follows. The scFv is used as a template in a PCR reaction with oligonucleotides 5'-TATC CGC GCG CAC TCC GAG GTG CAG CTG TTG GAG TCT GGG GG-3' (SEQ ID NO:23) and the reverse complement of 5'-ACC CGG GTC ACC GTC TCC TCC GGT GAG TCC TAG CGC TTT TCG T-3' (SEQ ID NO:24). The PCR fragment of approximately 750-800 by is isolated, digested with BssHII and Eco47III and cloned into similarly cut plasmid VHExpress. Similarly, the scFv genes of antibodies JB and M57 are cloned into this plasmid; to avoid digestion at internal sites the other suitable site is used (Bpu1102I) or a three-way ligation which also yields the same plasmid. The resulting plasmids with correctly cloned scFv, called respectively pscFv-Fc-JA, pscFv-Fc-JB and pscFv-Fc-M57, are introduced into host cells, in this example PER.C6™ cells.

For an initial analysis, these plasmids are transiently expressed either alone or in combinations of two or three scFv-Fc constructs. Cells grown to $5\times10^6$ cells/ml in culture medium with 10% Fetal calf serum (FCS) in 80 $cm^2$ flasks are transfected for four hours using lipofectamine (Invitrogen Life Technologies) according to the manufacturer's instructions (140 microliters Lipofectamine per 10 micrograms of DNA per flask) in serum-free medium at 37° C. After this incubation, cells are washed, resuspended in rich culture medium, and the cells grown for five days. The supernatant is harvested for analysis of the secreted scFv-Fc fusion protein. A sandwich ELISA is used to quantify the amount of IgG produced, using two antibodies directed to the Fc region. The scFv-Fc fusion proteins are purified using protein A affinity chromatography using a HighTrap column (Amersham Pharmacia) according to the manufacturer's instructions for IgG1), and the eluate concentrated via Microcon-YM30 concentrator (Amicon) and its buffer exchanged for PBS pH 7.0. The occurrence of different scFv-Fc mixtures, six in total for the cells transfected with the three scFv-Fc genes, are further characterized as described above in ELISA, and using viral isolates that are specifically recognized by the antibodies, including European bat virus 2 for antibody JB and Lagos bat virus and Mokoa virus for antibody JA, and strains CVS-11, CVS-24, PM, SHBRV and COSRV (Champion et al., *J. Immunol. Methods* (2000) 235:81-90). The presence of the M57 and JB binding sites is confirmed using an anti-Id antibody (see also Examples 14 and 22). Following this, the viral neutralization activity of the mixture of three monospecific and three bispecific molecules (without purification) is assayed for the presence of rabies virus-neutralizing antibodies using the rapid fluorescent focus inhibition test (RFFIT) as described by Hooper et al., ASM Pres, WA, p. 1997. Essentially, serial dilutions are made of the supernatant containing the antibody mixture in 96-well plates (Nunc), and a rabies virus dilution known to cause 70-80% infection of indicator cells added to each well. Controls are positive rabies-immune serum control samples and negative medium are also included. After one hour, to each well, 50,000 baby hamster kidney (BHK) cells are added and the culture incubated overnight at 37° C. Plates are then washed once with ice-cold PBS and the cells fixed with ice-cold 90% acetone for 20 minutes at −20° C. Acetone is removed and to the air-dried plates 50 microliters of FITC-labeled anti-rabies nucleoprotein monoclonal antibody (ab 1002 from abcam site or antibody from Centocor, Malvern) is added. After one hour incubation at 37° C., the plates are washed three times with water and analyzed under a fluorescence microscope. The activity of each of the scFv-components is studied by testing in this assay the neutralization of a variety of different rabies isolates, including the ones mentioned in Example 1.

The same plasmids, pscFv-Fc-JA, pscFv-Fc-JB and pscFv-Fc-M57, are also suitable for making stable transfectants. By selection using the neo-resistance gene and culturing and screening methods known to those in the art, stable PER.C6™ derived cell lines expressing antibodies are obtained. Essentially $5\times10^6$ PER.C6™ cells are transfected using Lipofectamine according to the manufacturer's instructions, and 3 micrograms of DNA per plasmid. Cells are transfected with the 3 micrograms of each plasmid separately, or with 1.5 micrograms each of pscFv-Fc-JA and pscFv-Fc-JB, or with 1.5 micrograms each of pscFv-Fc-JB and pscFv-Fc-M57, or with 1 microgram of each of pscFv-Fc-JA, pscFv-Fc-JB and pscFv-Fc-M57, or with a control LacZ vector. After five hours, the cells are washed and the medium is exchanged with non-selective medium. The next day the medium is replaced with fresh medium containing 500 micrograms/ml G418 (Sigma-Aldrich) and also every next two to three days, the culture medium is refreshed until clones appear (15 to 20 days after seeding). Clones are picked and cloned out to limiting dilution conditions, such that two to three weeks later, clonal cell lines start appearing. These are expanded to larger wells and flasks, and eventually the selective medium is omitted. The supernatant of these cell lines is harvested for analysis of the secreted scFv-Fc fusion protein. As before, a sandwich ELISA (as described in WO 00/63403) is used to quantify the amount of IgG produced, using two antibodies directed to the Fc region. The scFv-Fc fusion proteins are purified using protein A affinity chromatography using a HighTrap column (Amersham Pharmacia) according to the manufacturer's instructions for IgG1. Purified scFv-Ig from various clones is isolated, purified and tested in a series of assays. The first is to analyze the presence of the two or three different scFv genes of the cell lines created, by amplifying the genomic DNA of these cell lines with antibody JA/JB or M57 scFv or V-gene-specificoligonucleotides, and confirming the presence by sequencing the amplified material. The copy number of each of the integrated antibody constructs is determined with methods such as Southern blot or Fluorescent In Situ Hybridization (FISH). Secondly, the mixture is biochemically characterized using SDS-PAGE and iso-electric focusing. Alternatively, anti-idiotype antibodies or peptide mimitopes are used to delineate the compositions (see Example 12). The stability of the expression level, of the ratios between the different scFv components, and of the composition of the antibody mixture produced by cell lines which produce the mix of three or six proteins is followed over time by these assays. Finally, binding and neutralization assays are carried out, including antigen binding in ELISA and in fluorescence microscopy with infected cells and tissues, and in the RFFIT virus neutralization assay as described above. The biological activity of the mixture is tested against a range of rabies isolates and the activity determined according to the international Units of Rabies Antibodies and referenced to WHO reference Rabies Immunoglobulin (WHO Technical Series Report (1994) vol 848, p. 8; and vol. 840). By testing the biological activity (virus neutralization) of a series of cell lines producing variable quantities of the three scFv-Fc fusions, the most optimal mixture is identified. The mixtures are compared to the activity of ImmoGam® Rabies, the human immunoglobulin preparation used for passive immunotherapy (see also http://www.aventispasteur.com/usa/product/pdffiles/!LE3439I.PDF). The effect of the bispecific component is tested by comparing the neutralization efficacy of the scFv-Fc protein mixture with the activity of comparable quantities of the (1) individual whole recombinant antibodies JA (IgG1), JB (IgG1) and M57 (IgG1), (2) mixtures of two or three of these antibodies. Due to the discrepancy observed sometimes between in vitro and in vivo neutralization data, besides in vitro neutralization tests, it may sometimes be necessary to carry out in vivo neutralization tests using mouse protection experiments as described in Dietzschold et al. (1992) *PNAS* 89:7252.

Example 4

Figure 17:
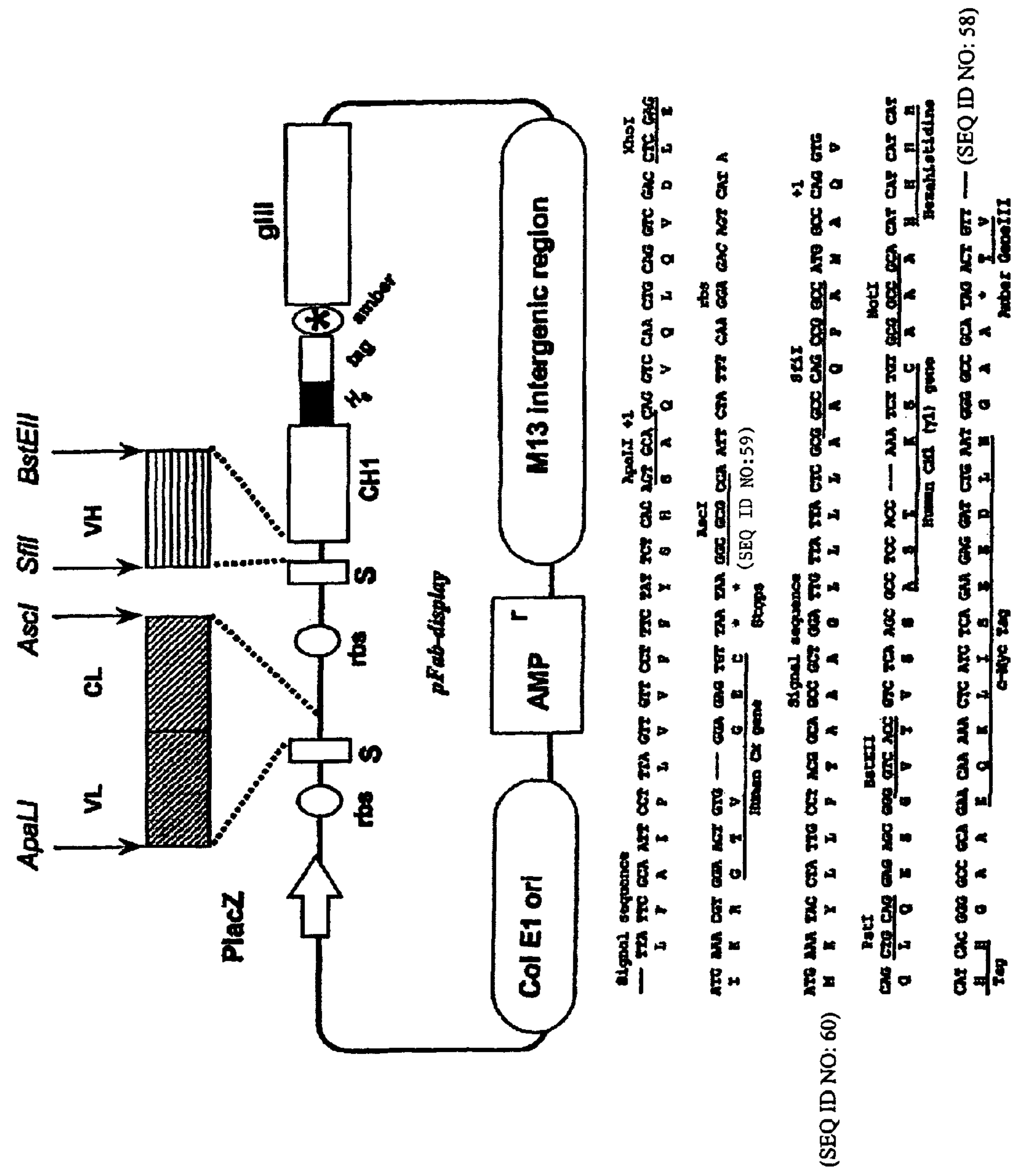
FIG. 17: pFAB-display: Schematic depiction of pFAb-display (top), and indication of cloning of VLCL and VH regions; the polylinker region (below). Legend as in FIG. 14.

Selection of Optimally Paired Variable Regions for Two Antibody Variable Region Pairs by Optimizing the Light Chain Variable Region Antibodies M57 and JB are used in this experiment. Both have a lambda light chain, of class I for JB and class II for M57, with homology between the two chains (FIG. 16). The antibody heavy chain variable region genes of these two antibodies are cloned into vector pFab-display, which resembles functionally pCES1 (H. J. de Haard et al. (1999) *J. Biol. Chem.* 274:18218-18230), and is a Fab fragment display and expression vector. In this vector system, the variable heavy chain region genes are cloned as VH-gene fragments; the vector supplies all Fabs with a human gamma-1 CH1 gene. The Fd fragment is fused to two tags for purification and detection: a histidine tail for Immobilized Metal Affinity Chromatography (IMAC) and a c-myc-derived tag, followed by an amber stop codon and the minor coat protein III of filamentous phage fd. The antibody light chain is cloned as full VLCL fragment, for directed secretion and assembly with the VHCH1 on the phage particle. Restriction enzyme sites and the sequence of the polylinker region is indicated in FIG. 17. The cloning of the variable regions is carried out similarly as described in Example 2, with oligonucleotides to amplify the VH region and that append appropriate restriction enzyme sites. The resulting plasmids are designated pVH-M57 and pVH-JB, respectively.

These plasmids are used as recipients for a collection of human lambda chains derived from human donors. B lymphocytes are isolated from 2-L of blood on a Ficoll-Pacque gradient. For RNA isolation, the cell pellet is immediately dissolved in 50 ml 8 M guanidinium thiocyanate/0.1 M 2-mercaptoethanol. Chromosomal DNA is sheared to completion by passing through a narrow syringe (1.2/0.5 mm gauge), and insoluble debris is removed by low speed centrifugation (15 minutes 2,934×g at room temperature). RNA is pelleted by centrifugation through a CsCl-block gradient (12 ml supernatant on a layer of 3.5 ml 5.7 M CsC1/0.1 M EDTA; in total four tubes) during 20 hours at 125,000×g at 20° C. in an SW41-rotor (Beckman). RNA is stored at −20° C. in ethanol. Random primed cDNA is prepared with 250 μg PBL RNA. RNA is heat denatured for five minutes at 65° C. in the presence of 20 μg random primer (Promega), subsequently buffer and DTT are added according to the suppliers instructions (Gibco-BRL), as well as 250 μM dNTP (Pharmacia), 800 U RNAsin (40 U/μl; Promega) and 2,000 U MMLV-RT (200 U/μl; Gibco-BRL) in a total volume of 500 μl. After two hours at 42° C., the incubation is stopped by a phenol/chloroform extraction; cDNA is precipitated and dissolved in 85 μl water. From this material, the variable region gene pools from the light chain lambda family are amplified using 4 Vλ-specific oligonucleotides that preferentially pair to the lambda I and II families (HuVl1A/B/C-BACK and HuVl2-BACK as in Table below) and with two primers based in the constant regions (HuCl2-FOR and HuCl7-FOR as in Table 1 below, combined in each reaction), and with PCR in a volume of 50 μl, using AmpliTaq polymerase (Cetus) and 500 pM of each primer for 28 cycles (one minute at 94° C., one minute at 55° C. and two minutes at 72° C.). All products are purified from agarose gel with the QIAex-II extraction kit (Qiagen). As input for reamplification to introduce restriction sites, 100 to 200 ng purified DNA-fragment is used as template in a 100 μl reaction volume, using the oligonucleotides appropriately extended to provide the sites for cloning, ApaLI and AscI (last six primers of following Table). This amplified material is purified, digested with AscI and ApaLI and two samples cloned into the two different plasmids pVH-M57 and pVH-JB.

| | |
|---|---|
| HuV11A-BACK | 5'-CAG TCT GTG CTG ACT CAG CCA CC-3' (SEQ ID NO: 25) |
| HuV11B-BACK | 5'-CAG TCT GTG YTG ACG CAG CCG CC-3' (SEQ ID NO: 26) |
| HuV11C-BACK | 5'-CAG TCT GTC GTG ACG CAG CCG CC-3' (SEQ ID NO: 27) |
| HuV12-BACK | 5'-CAR TCT GCC CTG ACT CAG CCT-3' (SEQ ID NO: 28) |
| HuC12-FOR | 5'-TGA ACA TTC TGT AGG GGC CAC TG-3' (SEQ ID NO: 29) |
| HuC17-FOR | 5'-AGA GCA TTC TGC AGG GGC CAC TG-3' (SEQ ID NO: 30) |
| HuV11A-BACK-APA | 5'-ACC GCC TC ACC AGT GCA CAG TCT GTG CTG ACT CAG CCA CC-3' (SEQ ID NO: 31) |
| HUV11B-BACK-APA | 5'-ACC GCC TCC ACC AGT GCA CAG TCT GTG YTG ACG CAG CCG CC-3' (SEQ ID NO: 32) |
| HuV11C-BACK-A.PA | 5'-ACC GCC TCC ACC AGT GCA CAG TCT GTC GTG ACG GAG CCG CC-3' (SEQ ID NO: 33) |
| HUV12-BACK-APA | 5'-ACC GCC TCC ACC AGT GCA CAR TCT GCG CTG ACT CAG CCT-3' (SEQ ID NO: 34) |
| HuC12-FOR.ASC | 5'-ACC GCC TCC ACC GGG CGC GCC TTA TTA TGA ACA TTC TGT AGG GGC CAC TG (SEQ ID NO: 35) |
| HuC17-FOR-ASC | 5-ACC GCC TCC ACC GGG CGC GCC TTA TTA AGA GCA TTC TGC AGG GGC CAC TG (SEQ ID NO: 36) |

This cloning results in two libraries designated as Fab-VH-M57-VLn and Fab-VH-JB-VLn.

Phage particles are made from cultures of these two libraries. The rescue of phagemid particles with helper phage M13-KO7 is performed according to (Marks et al. (1991), *J. Mol. Biol.* 222:581-597) on a 1-L scale, using representative numbers of bacteria from the library for inoculation, to ensure the presence of at least ten bacteria from each clone in the start inoculum. For selections, $10^{13}$ cfus (colony forming units) are used with 10 micrograms/ml Rabies glycoprotein coated in immunotubes (Maxisorp tubes, Nunc) or with 250 nM soluble biotinylated G protein. Antigen is biotinylated at a ratio of one to five molecules NHS-Biotin (Pierce) per molecule antigen according to the supplier's recommendations.

Three rounds of selection are carried out with these libraries. Detailed protocols for culturing and selecting phage display libraries have been described elsewhere (as in Marks et al. (1991), *J. Mol. Biol.* 222:581-597) and are well known to those working in the art. Briefly, the selection with the biotinylated antigen is carried out as follows. Phage particles are incubated on a rotator wheel for one hour in 2% M-PBST (PBS supplied with 2% skimmed milk powder and 0.1% Tween-20). Meanwhile, 100 μl Streptavidin-conjugated paramagnetic beads (Dynal, Oslo, Norway) are incubated on a rotator wheel for two hours in 2% M-PBST. Biotinylated antigen is added to the pre-incubated phage and incubated on a rotator wheel for 30 minutes. Next, beads are added and the mixture is left on the rotator wheel for 15 minutes. After 14 washes with 2% M-PBST and one wash with PBS, phage particles are eluted with 950 μl 0.1 M triethylamine for five minutes. The eluate is immediately neutralized by the addition of 0.5 ml Tris-HCl (pH 7.5) and is used for infection of long-phase *E. coli* TG1 cells. The TG1 cells are infected for 30 minutes at 37° C. and are plated on 2×TY (16 g Bacto-trypton, 10 g Yeast-extract and 5 g NaCl per liter) agar plates, containing 2% glucose and 100 μg/ml ampicillin. After overnight incubation at 30° C., the colonies are scraped from the plates and used for phage rescue as described (Marks et al. (1991), *J. Mol. Biol.* 222:581-597). Culture supernatants of individual selected clones harboring either rescued phage or soluble Fab fragments are tested in ELISA with directly coated antigen or indirectly captured biotinylated antigen via immobilized biotinylated BSA-streptavidin. Here described is the procedure with biotinylated antigen for the detection of soluble Fab fragments. For capture of biotinylated Rabies glycoprotein, first biotinylated BSA is coated at 2 μg/ml in PBS during one hour at 37° C. After three washes with PBS-0.1% (v/v) Tween 20 (PBST), plates are incubated during one hour with streptavidin (10 μg/ml in PBS/0.5% gelatin) (24). Following washing as above, biotinylated antigen is added for an overnight incubation at 4° C. at a concentration of 3 μg/ml. The plates are blocked during 30 minutes at room temperature with 2% (w/v) semi-skimmed milk powder (Marvel) in PBS. The culture supernatant is transferred to these wells and diluted 1 or 5-fold in 2% (w/v) Marvel/PBS and incubated for two hours; bound Fab is detected with anti-myc antibody 9E10 (5 μg/ml) recognizing the myc-peptide tag at the carboxyterminus of the heavy Fd chain, and rabbit anti-mouse-HRP conjugate (DAKO). Following the last incubation, staining ms performed with tetramethylbenzidine (TMB) and $H_2O_2$ as substrate and stopped by adding half a volume of 2 N $H_2SO_4$ the optical density is measured at 450 nm. Clones giving a positive signal in ELISA (over 2× the background), are further analyzed by BstNI-fingerprinting of the PCR products obtained by amplification with the oligonucleotides M13-reverse and geneIII-forward (as in Marks et al. (1991), *J Mol. Biol.* 222:581-597).

Large-scale induction of soluble Fab fragments from individual clones is performed on a 50 ml scale in 2×TY containing 100 μg/ml ampicillin and 2% glucose. After growth at 37° C. to an $OD_{600}$ of 0.9, the cells are pelleted (ten minutes at 2,934×g) and resuspended in 2×TY with ampicillin and 1 mM IPTG. Bacteria are harvested after 3.5 hours growing at 30° C. by centrifugation (as before); periplasmic fractions are prepared by resuspending the cell pellet in 1 ml ice cold PBS. After 2 to 16 hours rotating head-over-head at 4° C., the spheroplasts are removed by two centrifugation steps: after spinning during ten minutes at 3,400×g, the supernatant is clarified by an additional centrifigation step during ten minutes at 13,000×g in an Eppendorf centrifuge. The periplasmic fraction obtained is directly used for determination of the affinity by surface plasmon resonance and of fine-specificity in western blot or virus neutralization studies.

Using the cited ELISA test, panels of antigen reactive Fabs are identified for both M57 and JB. The Fabs are purified and their relative affinity for the antigen compared to the native antibody as Fab determined. All clones that are in a ten-fold reach of the affinity are sequenced. For sequencing, plasmid DNA is prepared from 50 ml cultures grown at 30° C. in medium, containing 100 μg/ml ampicillin and 2% glucose, using the QIAGEN midi-kit (Qiagen). Sequencing is performed with the thermocycling kit (Amersham) with CY5-labeled primers CH1FOR (5'-GTC CTT GAC CAG GCA GCC CAG GGC-3' (SEQ ID NO:37)) and M13REV (5'-CAG GAA ACA GCT ATG AC-3' (SEQ ID NO:38)). The analysis is done as described above: the amino acid sequences of the two antibody VL sets, for M57 and JB, are compared to one another. Many of the selected variants are derived from the lambda 1 and lambda 2 family but carry somatic mutations throughout the sequence. In each collection, a set of 10 VLs are selected that are putative "common" candidates for pairing to both VHs, and these are cloned via the common restriction sites ApaLI and AscI into the plasmid carrying the other VH. Thus, the VLCL of a candidate clone of library Fab-VH-M57-VLn is isolated using gel-electrophoresis of the ApaLI-AscI digest and cloned into pVH-JB. This is carried out for all candidate VLs; the new combinations are all tested as before in ELISA for their pairing compatibility with the non-cognate VH. The clone with highest affinity in both antibodies is designated VL-M57=JB. This procedure leads to the identification of a lambda variable region light chain that in the Fab format can optimally pair with both the VH of JB and of M57.

Example 5

Figure 18:
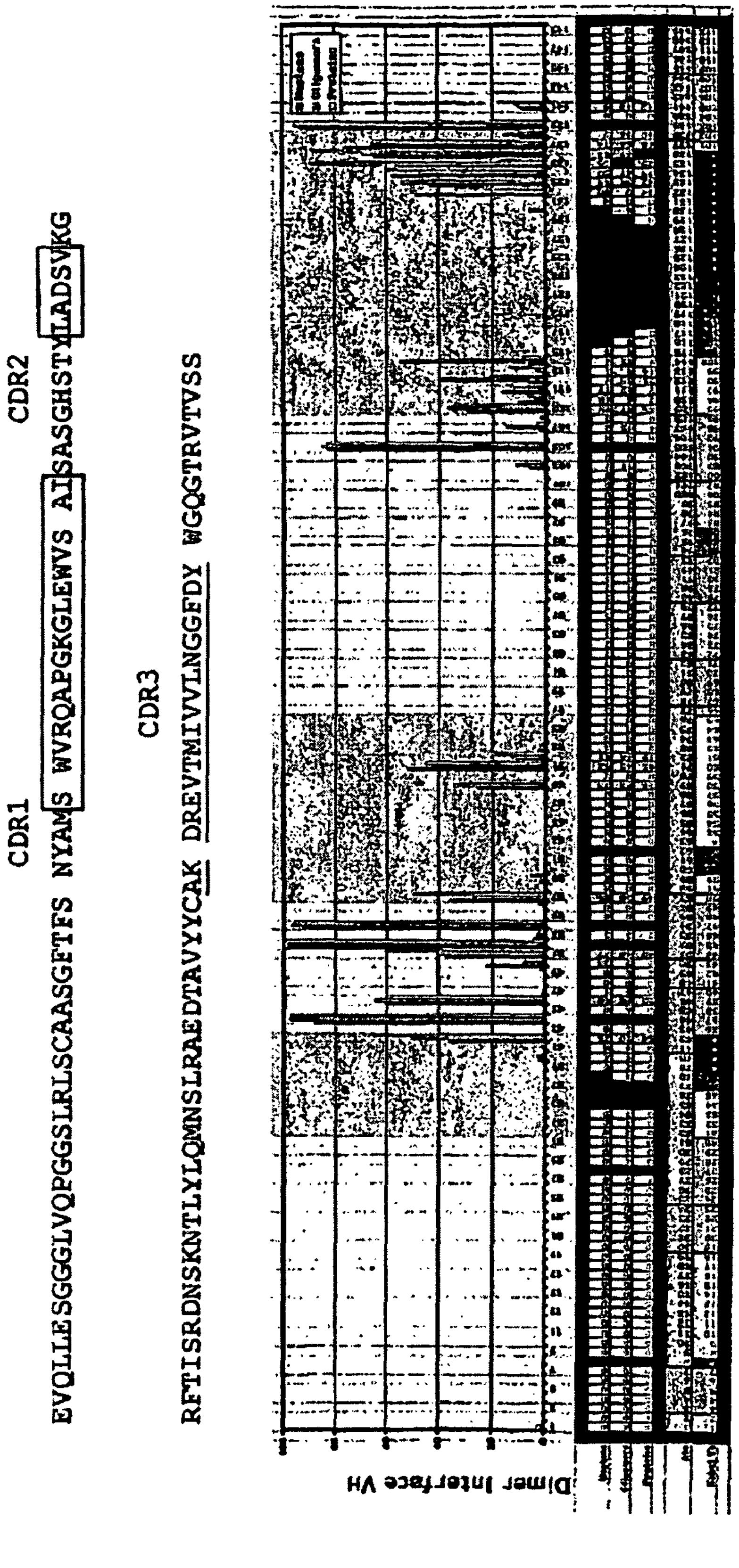
FIG. 18: Mutagenesis of heavy chain variable region of the JA antibody (SEQ ID NO:7); underlined region was mutagenized. Other regions known to be important for the interaction with the VL: the residues at the positions marked in color (bottom) or with the boxes around the JA-VH sequence are, alternatively, suitable for mutagenesis (based on data from worldwideweb.biochem.unizh.ch/antibody/Structures/DimContacts/VHDimHistFrame.html).

Selection of Optimally Paired Variable Regions for Two Antibody Variable Region Pairs by Optimizing the Heavy Chain Variable Region For occasions where the two light chains of two given antibodies are very different from one another, as is the case between antibodies of kappa and lambda families, it is also possible to follow an alternative strategy than the one described in Example 4. Herein we describe the selection of an optimally paired VL that will be pairing in a compatible fashion with two VH variable regions. In the experiment, the major loop in the VH, the CDR3 that is both responsible for antigen binding and contributes to the interaction with the light chain, is diversified. Other schemes can be followed, in which other VH residues known to be structurally positioned at the VH-VL interface are mutated (exemplified in FIG. 18). This procedure may also be applied to multiple variable region genes, using a chosen, preferably germ line encoded variable region gene and multiple partner variable regions which are then mutagenized and selected as in the following description.

The aim of the experiment is to find a JA-variant that will have optimally pairing behavior to VL-M57=JB. The JA antibody carries a kappa chain instead of a lambda (FIG. 16), and replacement of its cognate light chain with VL-M57-JB leads to a substantial loss of affinity. Therefore, it is the VH of this antibody that will be mutated, to compensate for loss of affinity with the antigen, and to provide also a also new potential interactions with the new VL. First, the VL-M57=JB is cloned as VLCL ApaLI-AscI fragment into pFab-display as described in Example 4; this yields plasmid pVL-M57=JB. The heavy chain of antibody JA is amplified from pVH-JA (Example 2) using two primers: 5'-GTC CTC GCA ACT GCG GCC CAG CCG GCC ATG GCA GAG GTG CAG CTG TTG GAG TCT GGG GG-3' (SEQ ID NO:39), and the reverse complement of the following sequence, which is a mutagenic oligonucleotide that is spiked with mutations in the two residues preceding the CDR3 and throughout the CDR3 region (in the underlined region; see also FIG. 18): 5'-C ACG GCC GTA TAT TAC TGT GCGAAAGATCGAGAGGTTACTATGATAGTTGTACT TAATGGAGGCTTTGACTACTGG GGC CAG GGA ACC CGGG TCA CCG TCT CCT-3' (SEQ ID NO:40). The spiking is carried out by the inclusion during the oligonucleotide synthesis at the underlined residues, of mixes of 90% of the natural residue, and 10% of a mix with equimolar ratios of the four residues. The PCR is carried out as in Example 1 to yield a 350-400 by fragment, which is gel-purified, digested with SfiI and BstEII and cloned into pVL-M57=JB, to form a library of variants of JA, designated Fab-JA-YHmut.

This library is now rescued using helper phage and selections and screenings are carried out on Rabies glycoprotein according to the methods described in Example 4. The resulting Fab clones that maintain antigen binding contain a VH-JA variant that is pairing-compatible with VL-M57=JB. Candidate Fabs are produced and purified, and their affinity determined as described in Example 4. The variable heavy chain mutant of the highest affinity is designated VH-JA*.

Example 6

Isolation of Antibodies Against Rabies Glycoprotein from a Random Combinatorial Phage Library and Screening for Compatible VL Between Binding Clones Phage display libraries are a suitable source of antibodies for the present invention. Libraries that are suitable for the assembly of the panels of antibodies include non-immune libraries (H. J. de Haard et al. (1999) *J. Biol. Chem.* 274: 18218-18230), semi-synthetic libraries (de Kruif et al. (1995) *J. Mol. Biol.* 248:97, and Griffiths et al. (1994) *EMBO J.* 13:3245-3260) and also immune libraries, which often display a lower level of variable chain diversity. The first application presented is to select antibodies to one antigen only, providing a mixture of antibodies directed to the same antigen that can then be screened for pairing-compatible variable regions, and used to produce an antibody mixture. The second application concerns the selection of antibodies to two different antigens. Methods to carry out selections and screenings are well known in the art and are also described in Examples 4 and 5. Using selection on antigens, panels of antibody fragments specific for a given set of antigens are obtained. For each of the panels the sequence of VH and VL is determined. Thus, each antigen will have a set of reactive antibodies. It is then possible to identify by visual inspection in each of the panels those antibodies that share a given VL or have highly related VLs between the different sets. The cases described in Example 4 are also applicable here. In the best case each set has at least one antibody with an identical VL as at least one other antibody in the other sets. When this is not the case, a suitable VL that matches a given VH is found by the methods described in Example 4: the VH is paired with a repertoire of VLs, of which the composition is driven by the homology with a given VL or VLs. Alternatively, one VL is chosen and the non-matching VH is mutagenized as described in Example 5, to yield compatible pairs for all sets. The sequences are further inspected to find pairing-compatible variable regions that do not have sequence identity or homology. Variable heavy chains that pair with multiple variable light chains and vice versa are identified. Such "promiscuous" pairings imply that the variable region involved binds to the same antigen with any of several partner chains. To rapidly identify such variable regions, it is particularly useful to use semi-synthetic antibody libraries which have a limited number of positions which were diversified, as has been described for the human synthetic phage antibody library in Griffiths et al. (1994) *EMBO J.* 13:3245-3260.

In the first application, antibodies are selected against one antigen, the Rabies glycoprotein. The library described in Griffiths et al. (1994) *EMBO J.* 13:3245-3260, is selected on the Rabies glycoprotein antigen as described earlier. There are different sources of the antigen, including the material purified as in Dietzschold et al. (1996) *Laboratory Techniques in Rabies*, Eds Meslin, Kaplan and Korpowski, World Health Organization, Geneva, p. 175. Alternatively, a source of recombinant Rabies Glycoprotein (G) of the appropriate type is used for the coating. The sequence of rabies G is available to persons in the art and so are cloning, expression and purification techniques. A suitable format is to use an immuno-adhesion-type of molecules, in which the soluble part of the glycoprotein is genetically fused to an immunoglobulin Fc region, and the fusion protein expressed in eukaryotic cells (see also Chamow and Ashkenazi, *Antibody Fusion Proteins,* 1999, Wiley-Liss, NY). For phage selection, the immuno-adhesion is biotinylated to be used in a selection as described in Example 4, or immobilized by coating. Alternatively, selections are carried out on immobilized (or biotinylated) Rabies virions, and selections are carried out each round on virions derived from different Rabies strains, to obtain a panel of antibodies that recognize the most common epitopes present in the different strains. These procedures yield a panel of antibodies directed to the Rabies antigen, but the compatibility of the pairing of variable regions of the individual candidates has to be tested.

We disclose here the use of the antibodies from the phage antibody library described by Griffiths et al. (1994) *EMBO J.* 13:3245-3260, but for the clones from other libraries the same principles apply. A panel of Fabs reactive with the Rabies glycoprotein is identified and the procedure to find optimally pairing VH and VL combinations as described above carried out. As an alternative, independent of sequencing, to identify optimally paired VH and VL pairs (that, for example, are missed in the sequencing analysis), the following empirical approach is followed. The variable light chains of a panel of 30 human antibodies are shuffled, and the new combinations tested in a binding assay. The shuffling is carried out by recloning the light chains present in the antigen reactive Fab clones which are based in the recombined fd-DOG-2lox-plasmid, as ApaLI-AscI fragment into the same Fab-containing phage genomes cut with the same (unique) enzymes. This is an experiment that is done in batch, with all 30 VL inserts and 30 VH-containing vectors mixed; sequencing is used to delineate the pairing of each VH-VL pair. ELISA is used to define which antibodies retain antigen binding activity and those clones are sequenced. The resulting combinations provide VH-VL which are pairing-compatible, the first class of which is formed by clones that share a VL or related VL; in that case one can be chosen plus the different VH genes for making Oligoclonics™ (see Example 10). The second class contains clones with "promiscuous" pairing, and the VH genes of these are combined with the VH and VL pairs of those Fabs which are compatible with this tolerant VH.

The second application concerns the selection of phage antibodies on two different antigens, as indicated in FIG. 2. The same procedures as were just described for one antigen are followed, now to assemble two sets of antibodies, one for each antigen. The same procedures are followed also to identify clones with an identical or similar variable region sequence, or empirically, to demonstrate the existence of pairing-compatible antibodies between the two sets of antibodies.

Example 7

Figure 3:
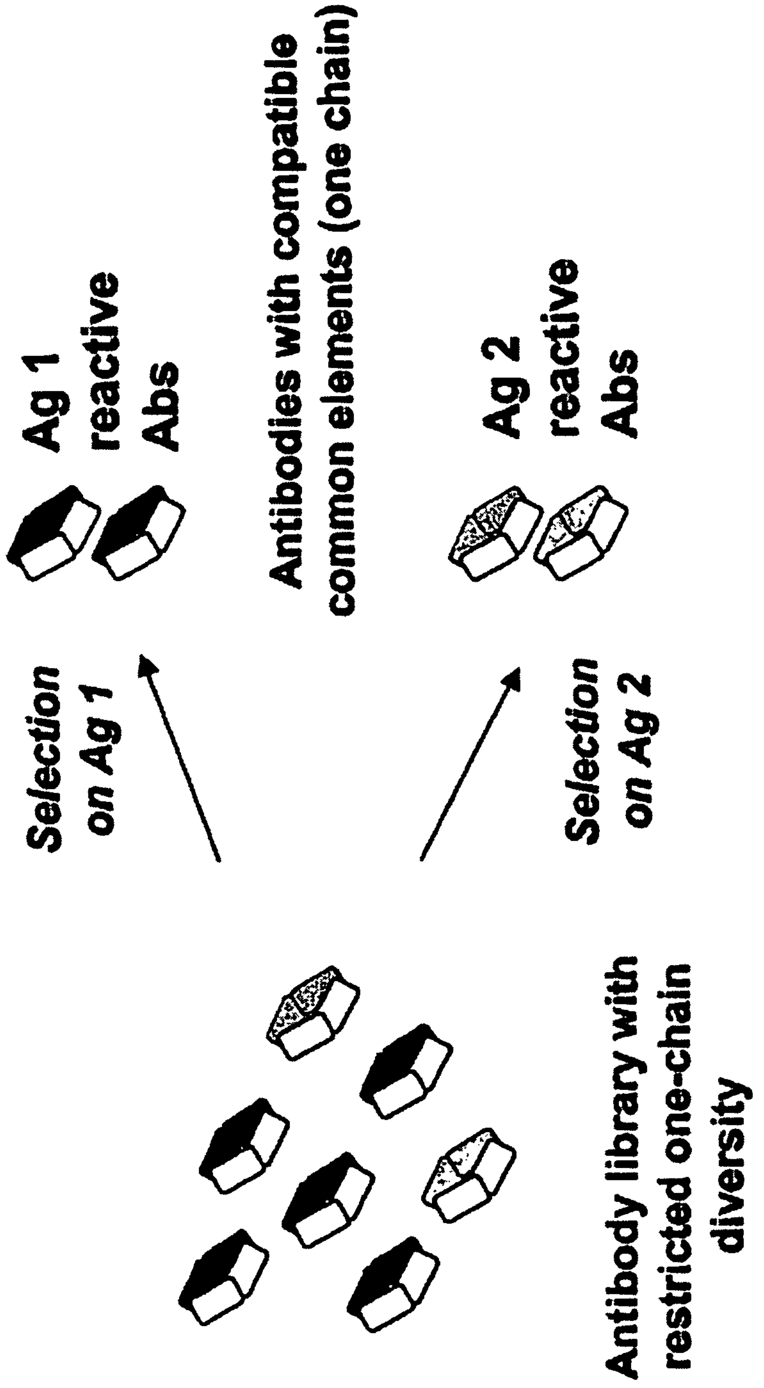
FIG. 3: Antibodies with similar light or heavy chain by selection from libraries with restricted diversity. In this example of a Fab library, one of the antibody chains is identical in all library members (the white chain), while the others contain amino acid diversity.

Isolation of Antibodies Against Rabies Glycoprotein from a Phage Library with Limited Diversity and Screening Antibodies Which are Non-Competitive Phage antibody scFv or Fab libraries that are formed by focusing the diversity in one variable region and keeping the other variable region invariable, preferably a germ line sequence, are particularly relevant to the invention. From such libraries it is feasible to isolate antibodies with a different heavy chain yet identical light chain, or vice versa (FIG. 3). Such antibodies are readily reformatted into an Oligoclonics™ format according to the invention. In the art, it has been described that antibodies that share the same VL gene but have different VH genes and widely varying specificities can be obtained from phage antibody display libraries (Nissim et al. (1994), *EMBO J.* 13:692-698).

A sub-library of the semi-synthetic scFv library (de Kruif et al. (1995) *J. Mol. Biol.* 248:97) is used in the following example. This sub-library contains antibodies with diversity in the VH region only. Selections on antigen are carried out as described in the previous examples. Using Rabies glycoprotein as the antigen as described in Example 6, ten human antibodies with different VH yet identical VL are identified. These are immediately suitable for inclusion into Oligoclonics™ (Example 10). In some instances it will be favorable to identify those antibodies that recognize different epitopes from the other antibodies in the mixture, and/or to obtain antibodies that recognize the same epitope recognized by a given monoclonal and polyclonal antibody. The competitive nature of the selected ten scFv antibodies with the Rabies monoclonal antibody M57 is determined in ELISA, using the set-up described in Example 2 (essentially, with bound antigen, adding sample, and detecting using an HRP-labeled anti-c-myc antibody) in the presence or absence of the M57 antibody. Competition experiments between the clones are readily performed using similar competition ELISAs with the phage-scFv particles and the soluble scFv fragments. Besides this procedure to screen clones for a particular competition-behavior, it is also possible to influence the selection outcome, either by using an antibody to block a site on the antigen during the selection (preventing antibodies to or competing with this epitope from being selected), or by using an antibody to competitively elute the fraction of phage antibodies that is bound to the same epitope. Examples of both are known in the art and methods are applicable here also to define suitable antibody combinations for inclusion in the Oligoclonics™ composition.

Example 8

Isolation of Single-Domain Antibodies Against Rabies Glycoprotein from a VL Phage Library, and Pairing with a Suitable Variable Region Antibodies made in two steps are also suitable for the inclusion in the Oligoclonics™ format and to make antibody mixtures. Rabies-specific single domain VL antibody fragments are selected from a phage displayed repertoire isolated from human PBLs and diversified by DNA-shuffling, as described in van den Beucken et al. (2001), *J. Mol. Biol.* 591-601 (libraries B and C). Selection and screening experiments are done as described in the previous examples. After the third round of selection, the pool of VLs is taken for combination with one VH segment (as depicted in FIG. 4(*e*)). For this, the VL pool is recloned by PCR as an ApaLI-XhoII fragment into pFab-display (FIG. 17) into which is cloned a single human VH. The latter is a DP-47 germ line encoded variable region with short CDR3 sequence designated VH-N (SEQ ID NO:14), which is obtained by providing via PCR antibody clone FITC-B11 from Table IV in Griffiths et al. (1994) *EMBO J.* 13:3245.3260, with a short, five-residue CDR3 of amino acid sequence GGAVY (SEQ ID NO:41), and cloning this as SfiI-BstEII fragment into pFab-display. This CDR3 is found in many different antibodies, and a short sequence with minimal length side chains (except for the tyrosine) is chosen to minimize effects on antigen binding and pairing. The resulting mini-library is screened for those antibody Fab fragments that maintain antigen binding. The three best Rabies glycoprotein-specific VL genes are designated VL-G1, G2 and G3. Similarly, the principles of this approach are applicable to building antigen-specific heavy chain fragments based on the VH domain, and providing these with a "neutral" VL, or even "neutral" partner VH.

Example 9

Selection of Antibodies with Pairing-Compatible Variable Regions by Intracellular Competition, and Expression of a Composition of Two or Three Fab Fragments with Pairing-Compatible Variable Regions Selections with phage libraries are carried out using monoclonal antibodies as competitors during the formation of new phage particles. The selection biases the library selection towards variable region pairs with compatible pairing in the context of multiple variable regions being expressed in the same host cell. The system relies on the simultaneous expression of two or more Fab fragments, the variable region of one of which is anchored onto a phage coat protein (FIG. 5).

First, the variable region genes of antibody M57 are cloned into pFab-Sol-pbr, a derivative of pFab-display (FIG. 17) with the same polylinker, but no gIII, no M13 intergenic region and instead of pUC119 the pBR322 backbone carrying the ampicillin resistance gene. The variable region genes of antibody JB are cloned in pFab-Sol-ACY-cat, similar in set-up as the previous one but carrying the Chloramphenicol resistance gene and based on the pACYC backbone. Both plasmids mediate the expression of the soluble non-tagged Fab fragment under control of the lacZ promoter, and they are compatible with one another and can be maintained in the same cell with antibiotic selection. Methods for the cloning have been described earlier; the sequences of these antibodies are also included in the sequence listings below, thus it will be possible for someone working in the art to clone these Fabs into these polylinkers such that upon induction with IPTG, both antibodies are expressed in the periplasm of the culture. These two antibody Fab fragments form the competitors in this method. *E. coli* TG1 cells harboring both plasmids are infected with phage harboring a library of human Fab fragments, in which the heavy chain is anchored to the phage coat and the light chain is provided as a soluble, non-anchored chain. The fd-based library from Griffiths et al. (1994) *EMBO J.* 13:3245-3260, which contains both VH and VL diversity is used for infection, the resulting bacteria start producing new phage particles and incorporate the L and Fd chains expressed from this genome. Cells are grown to an OD of 1.0, the cells washed to remove produced phage, and the cells incubated for four hours in 1 mM IPTG. During this time, competition will occur for pairing between the three variable heavy and light chains, and there are many opportunities for mispairing. The phage produced during this induction time will only recognize the native antigen, if the VH is tolerant to pair with any VL yet bind antigen, or when it exclusively pairs with the VL that is also encoded in the genome. The phage is harvested, PEG precipitated, dissolved in PBS, and is now selected for binding to Rabies glycoprotein. Methods for selection have been described earlier. In both case the phage will be able to bind antigen, and be enriched in a selection round with antigen. The phage resulting from the selection is used to infect cells harboring the two Fab-containing plasmids, and the cycle of induction, phage preparation and selection is repeated. After five rounds of this selection, the resulting Fab proteins are tested for antigen binding in a solid phage ELISA and recloned into the soluble expression vectors pFab-Sol-ACY-cata and pFab-Sol-pbr. *E. colis* are transfected with one of these plasmids and either the M57-containing vector or the JB-containing vector described above, or no additional vector. These cultures are induced with IPTG (inducing expression of one or two Fab fragments), and the resulting Fab fragments and Fab mixes analyzed for antigen binding in ELISA. To confirm exclusive or tolerant pairing, the Fab fragments are purified using IMAC and tested in a capture assay with antigen as described in Example 2. The selected variable region pair can be further used to build an Oligoclonics™ mixture with either M57 or JB variable region genes (but not together), as in Example 10.

For making a mix of these three antibodies, the experiment is repeated using the VL-M57=JB from Example 4 instead of the two original light chains VL-M57 and VL-JB. The result of the selection is a small number of Rabies antigen-specific VH-VL pairs derived from the phage library. The best candidate according to affinity, with designated variable regions VH-PO1 and VL-PO 1, is further tested as above to confirm that it is pairing-compatible with the VH-57, the VH-JB and the VL-M57=JB. Next, the following expression cassettes are introduced in the same *E. coli* host cell using the two plasmids described earlier for producing the competing Fab, using cloning methods familiar to those working in the art: in cassette (1), on one plasmid, the VL-M57=JB-CL and VH-CH1 of M57; in cassette (2), the VL-M57=JB and VH-CH1 of JB (a second copy is provided to obtain an excess of light chain for pairing with the two heavy chains); and in cassette (3), on the other plasmid, the VL-PO1-CL and VH-PO1-CH1. Induction with IPTG leads to the production of a mixture of Fab fragments with paired variable regions, which is then recovered using IMAC purification. Alternatively, protein G purification is used. Using the binding and other assays described in the earlier examples for Rabies glycoprotein antibodies, the mixture is characterized. The contents of the mixture is dependent on the growth and induction conditions of the bacteria and the primary amino acid sequences of the Fab genes.

Example 10

Methods for Production of Oligoclonics™ in Eukaryotic Cells

Figure 19:
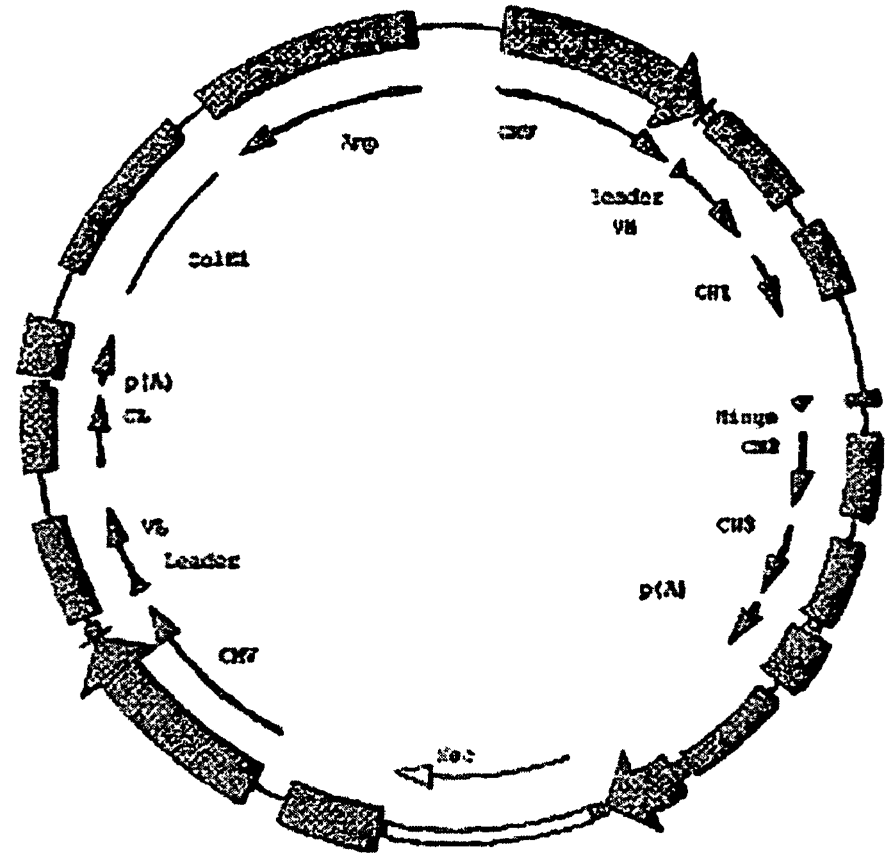
FIG. 19: Outline of an expression vector for human monoclonal antibodies in eukaryotic cells. CMV: CMV promoter; p(A): polyadenylation signal; Neo: neomycin resistance gene; Amp: ampicillin resistance gene.

A method for producing a mixture of antibodies in eukaryotic cells according to the invention, using expression in a recombinant host cell of multiple VH and VL genes resulting in the production of VH and VL proteins capable of pairing to form functional bivalent and bispecific antibodies, named Oligoclonics™, is exemplified herein. The general format of a eukaryotic expression vector for human monoclonal antibodies is shown in FIG. 19.

The VH and VL regions of human monoclonal antibodies specific for rabies virus obtained by any of the methods described in the previous examples, can be inserted into an eukaryotic expression vector containing the HATV20 leader sequence and all the coding sequences of the constant regions of human immunoglobulin heavy (for example, IgG1) and light chains (for example, a kappa light chain) essentially as described (E. Boel et al. (2000), *J. Immunol. Methods,* 239: 153-166). In this example, the following variable region genes optimized for pairing are used: VH-M57, VH-JB (non-modified variable region genes, from Example 2), VH-JA* (the optimized sequence of the VH of antibody JA, from Example 5), and only one light chain, VL=M57=JB (from Example 4). The resulting plasmids encoding heavy and light chains are transfected into eukaryotic cells such as the human cell line PER.C6™ and in Chinese Hamster Ovary (CHO) to generate stable cell lines secreting antibodies. For this, published methods and methods known to persons skilled in the art are used (E. Boel et al. (2000), *J. Immunol. Methods,* 239:153-166 and WO 00/63403). For the generation of stable PER.C6™ cells secreting antibodies, PER.C6™ cells are seeded in DMEM plus 10% FCS and in tissue culture dishes (10 cm in diameter) or T80 flasks with approximately $2.5\times10^6$ cell per dish or flask and kept overnight in an incubator at 37° C. and 10% $CO_2$. The next day, transfections are preformed in separate dishes at 37° C. using Lipofectamine (Invitrogen Life Technologies) according to standard protocols provided by the manufacturer. The plasmids encoding the monoclonal antibodies can be mixed in various ratios and used at a concentration of 1-10 µg/ml. As controls, cells are subjected to the transfection procedure in the absence of plasmids.

After four to five hours, cells are washed twice with DMEM and fed with fresh culture medium. The next day, the culture medium is removed and cells are fed with fresh medium containing 500 µg/ml of the antibiotic G418. Cells are fed every two or three days with culture medium containing 500 µg/ml of G418. After about 20 to 22 days after initiation of the experiment, a large number of colonies is visible and from each transfection, 300 clones are picked and grown individually in 96-well plates and further expanded in 24-well, 6-well and T25 flasks. At this stage, cells are frozen in liquid nitrogen and production levels of recombinant immunoglobulin are determined in an ELISA according to standard procedures (e.g., E. Boel et al. (2000), *J. Immunol. Methods,* 239:153-166 and WO 00/63403). At this stage of the culture procedure, G418 is no longer added to the culture medium.

To establish the presence of anti-rabies antibodies in a mixture, a solid phase anti-rabies ELISA is performed. For the rabies virus ELISA, rabies virus glycoprotein is purified according to standard procedures (Dietzschold et al., in F.-X. Meslin et al. eds., *Laboratory techniques in Rabies*, World Health Organization, Geneva, page 175). Plates (polySorb™, Nunc) are coated with 5 µg/ml of glycoprotein diluted in PBS and 150 µl/well. The plates are then blocked with 5% powdered milk in PBS and washed in PBS containing 0.05% Tween20 (PBS-Tween) prior to the addition of supernatant samples. Following incubation at room temperature for two hours, the plates are washed with PBS-Tween to remove unbound antibody present in the supernatant samples. Enzyme-conjugated or biotinylated secondary antibodies specific for various human heavy chain isotypes are added for one hour at room temperature and the plates are subsequently washed with PBS-Tween. Detection of secondary antibody is performed according to standard procedures (e.g., J. M. Champion et al. (2000), *J. Immunol. Methods* 235:81-90); see also previous examples. Other analysis methods are described in Examples 3, 4 and 12.

Next, it is demonstrated that a clonal cell line accounts for the production of each of the binding specificities encoded by the plasmids, i.e., proving that a single cell is able to produce a mixture of multiple anti-rabies antibodies. For a limited number of colonies that secrete a mixture of all monoclonal antibodies, 30 clones selected from the initial panel of approximately 300, clonality is further established by subcloning under limiting dilution known to persons skilled in the art. Picked and expanded colonies are seeded in a 96-well plate at a concentration of 0.3 cells/well in DMEM with 10% FCS and expanded. Colonies of cells are processed as described above and are referred to as subclones. Subclones are screened by PCR on genomic DNA for the presence or absence of each of the three constructs. Further confirmation of the presence of the constructs is obtained by nucleotide sequence analysis of the PCR products.

For a representative number of subclones, larger volumes are cultured to purify the recombinant human IgG1 fraction from the conditioned supernatant using Protein A affinity chromatography according to standard procedures. Purified human Ig from the various subclones is subsequently analyzed by SDS-PAGE, Iso-electric focusing (IEF) according to standard protocols (see, also, Examples 3 and 12).

Subclones that are shown to harbor the relevant plasmids are brought into culture for an extensive period of time to determine whether the presence of the plasmids is stable and whether expression of the antibody mixture remains the same, not only in terms of expression levels, but, in particular, the ratio between the various antibodies that are secreted from the cell. Therefore, the subclone culture is maintained for at least 25 population doubling times. At every four to six population doublings, a specific production test is performed using the human Ig-specificELISA and larger volumes are cultured to obtain the cell pellet and the supernatant. The cell pellet is used to assess the presence of the three constructs in the genomic DNA, either via PCR, Southern blot and/or FISH. The supernatant is used to purify the recombinant human Ig fraction as described. Purified human Ig obtained at the various population doublings is subsequently analyzed as described, i.e., by SDS-PAGE, Iso-electric focusing (IEF) and binding in the inhibition ELISA.

Example 11

Method for Selecting Antigen-Specific Proteinaceous Compounds Using Mixtures of Encoding DNA The basis for the mixtures of antibodies present in Oligoclonics™ are immunoglobulin variable regions that encode human monoclonal antibodies that have been selected for their specificity, contain variable region genes with compatible pairing behavior and are thus compatible with the Oligoclonics™ format. For example, antibodies that are encoded by different VH genes and bind to different epitopes but share the same VL gene are suitable for the Oligoclonics™ format. Example 7 describes how such antibodies are obtained.

In this example, methods using eukaryotic expression systems to obtain human monoclonal antibodies with desired specificities and that share the same VL gene are described. Such "repertoires" of human VH genes are PCR-amplified from the B lymphocytes of human individuals and typically harbor $10^8$ to $10^{10}$ members. The method is known to persons skilled in the art and has been described many times in the literature; the amplification of antibody genes is also exemplified for human V-lambda libraries in Example 4. The source of B lymphocytes may be any lymphoid organ including blood, bone marrow, tonsil, spleen, lymph node, etc. The individual may be pre-selected because it is expected that B lymphocytes producing the antibodies of interest are enriched in those individuals because of, e.g., a prior infection with a micro-organism or because of a prior immunization, or may be randomly picked. The VH genes may be used unaltered in their coding region or may be altered, particularly in the CDR3 region to introduce novel specificities. Such VH genes are known in the art as synthetic or semi-synthetic VH regions. Preferably, primers are used that selectively amplify members of a few VH gene families such as the large VH3 and VH4 gene families. Primers that amplify members of more VH gene families may also be used in procedures known by persons skilled in the art. Amplified VH regions are cloned into the eukaryotic expression vector for human monoclonal antibodies as described in Example 10 and subsequently introduced into eukaryotic cells such as CHO cells or PER.C6 cells. The expression plasmid shown in Example 10 that harbors a VL gene is used (FIG. 7). There are two alternatives: (1) the VL gene is co-transfected with the VH genes on a separate plasmid or (2) an approach particularly suitable when only one VL needs to be expressed the eukaryotic cells are already transfected with a human VL gene that is stably expressed. The eukaryotic cells are transfected with the repertoire of human VH genes cloned into the eukaryotic expression vector for human antibodies. High plasmid DNA concentrations are used to transfect the eukaryotic cells in order to introduce multiple copies of VH genes into a single cell. As a result a single cell will produce multiple antibodies, e.g., between 10 to 1000 different human antibodies. In the first approach, transfections are transient. In brief for PER.C6 cells, an 80 $cm^2$ tissue culture flask with cells is transfected by incubation for four hours with 140 μl lipofectamine+10 to 1000 μg plasmid DNA in serum-free DMEM medium. After four hours, the medium is replaced with DMEM+10% FCS, and the cells are grown overnight at 37° C. Cells are then washed with PBS and the medium is replaced with Excell 525 medium (JRH Bioscience). The cells are seeded at a concentration that results in the outgrowth of approximately 100 transfected cells/well of a 96-well culture plate. After five to six days, the cell culture supernatant is harvested and assayed for the presence of specific antibody by solid phase ELISA. The cells that correspond to the supernatants that score positive in ELISA are harvested and the VH genes are amplified by PCR. Subsequently, the amplified VH genes are cloned into the eukaryotic expression vector for human monoclonal antibodies, described in Example 10. Thus, a restricted repertoire of human VH genes is obtained. In this example, 100 cells that each harbors 100 VH genes yield a maximum of $10^4$ VH genes. This repertoire is transiently transfected into PER.C6 cells that harbor the same VL gene using low plasmid DNA concentrations (0.1 to 1 μg/ml) such that on average a single cell harbors a single VH gene and transfected cells are plated out under conditions such that only approximately ten cells/well will grow out. After five to six days, supernatants are screened in ELISA for specific antibodies and the cells corresponding to positive supernatants are harvested and used for PCR amplification of the VH genes. In this example, the maximum number of VH genes obtained is approximately ten. Each VH gene is separately transfected into PER.C6 cells and the VH gene encoding the desired antibody specificity is identified by screening the supernatants of clones in ELISA.

In a second approach, the initial library of $10^8$ to $10^{10}$ VH genes cloned together with a single VL gene into the plasmid described in Example 10, is transfected into PER.C6 cells and plated out in T80 cell culture flasks. After four to six days, the cells are harvested and mixed with red blood cells coated with the antigen of interest and individual cells are monitored for the secretion of specific antibodies against the coated antigen by the reverse hemolytic plaque assay, well-known in the art (e.g., F. Dammacco et al. (1984) *Clin. Exp. Immunol.* 57:743-51). B lymphocytes inducing plaques are visualized under a light microscope and picked with a micromanipulator. The single transfected PER.C6 cell is transferred to an Eppendorf tube, lysed and subjected to single cell PCR to amplify the VH genes. The advantage of this approach is that only a few rounds of selection are needed to identify the VH gene of interest.

In a third approach, stable transfectants are used. After the transfection as described above, large collections of clones are grown essentially as described in Example 10, with the exception that clones are not plated out under limiting dilution conditions. Instead, the cells after transfection are plated in microtiter plates such that after growth in the selective medium multiple clones per well arise (e.g., 100 cell clones per well as indicated in FIG. 7). Each clone expresses multiple species of heavy chains, and each well contains multiple clones. The supernatant of these cultures are tested for antigen binding and the VH-genes are further enriched in cycles of PCR, cloning, transfection and screening, as described above.

Figure 22:
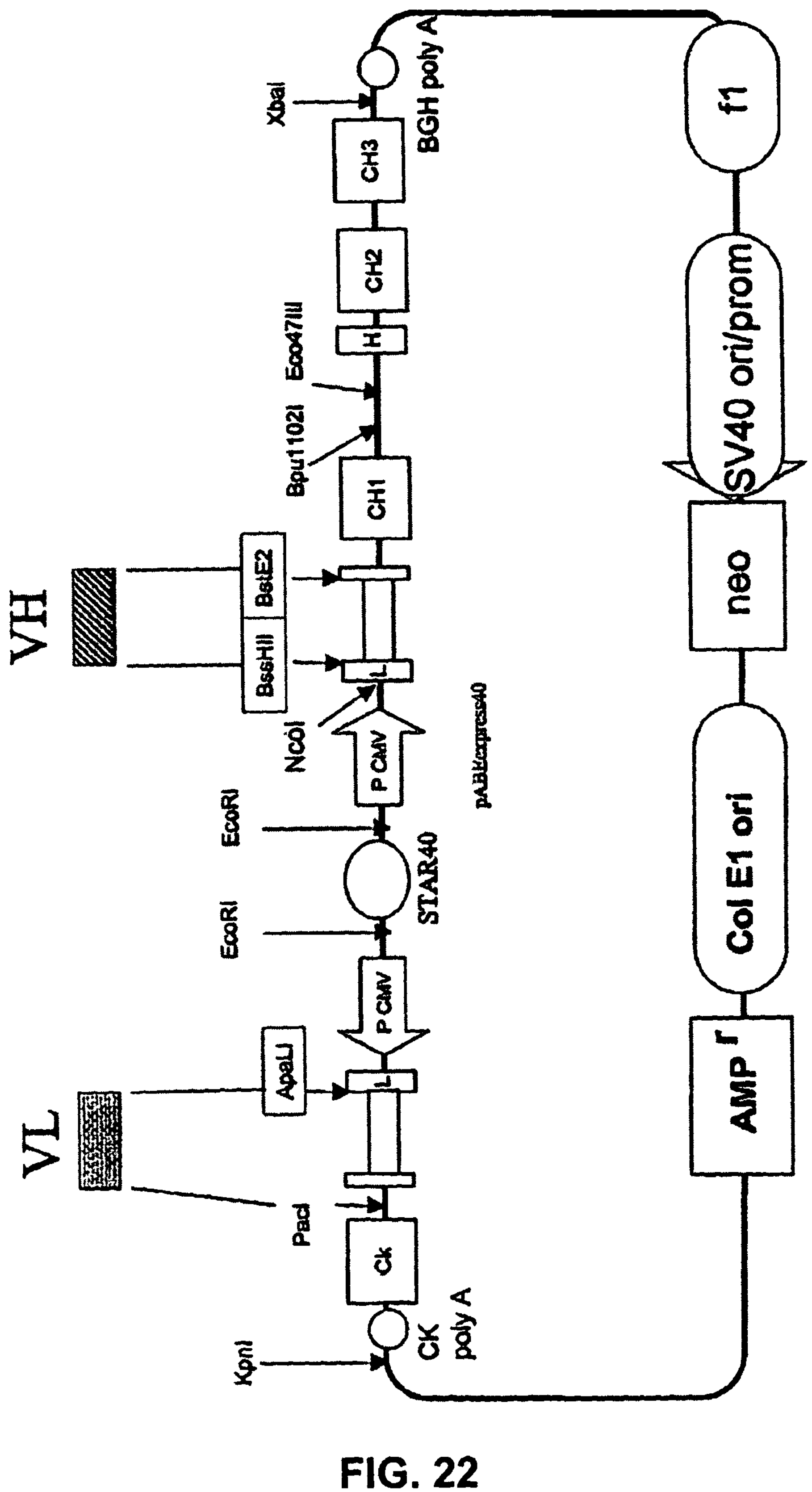
FIG. 22: Plasmid pABExpress40 for expression of libraries of pairing-compatible antibodies in mammalian cells. Cloning sites for directional insertion of antibody variable region genes are indicated. See Example 11 for details. Without the STAR40 insertion into the EcoRI site, this plasmid is called pABExpress.

The expression of multiple antibodies by a single transfected eukaryotic cell is improved in all of these approaches by introducing anti-repressor DNA elements in the plasmid constructs for the expression of human monoclonal antibodies. Anti-repressor elements confer high level and stable expression of proteins in mammalian cells in a copy number-dependent fashion (Kwaks et al. (2003), *Nat. Biotechnol.* 21:553-558). The DNA fragments responsible for this effect are amplified from the clones described in this citation and introduced upstream of the heavy chain expression cassette. The human anti-repressor element nr. 40 (SEQ ID NO:15) is amplified from the pSDH vector containing the element (described in Kwaks et al.), using flanking oligonucleotides that also incorporate restriction sites suitable for cloning (5'-GTCCCTAGGAATTCGATCAAGAAA GCACTCCGGG-3' (SEQ ID NO:42) and the reverse complement of 5'-CCTCATGATGTACATTAGAT CGAATTCGTAATACG-3' (SEQ ID NO:43)). In this example, EcoRI (GAATTC (SEQ ID NO:44)) which is not present in this segment, is appended at both ends of the segment in a PCR reaction, and the fragment digested with EcoRI and cloned into an EcoRI-digested acceptor plasmid. In this example, the latter is a chimeric plasmid of VHExpress and VLExpress, which is a composition made by cloning the full VHExpress plasmid (FIG. 15), cut with KpnI and EcoRI, and inserting the VK expression cassette that was digested with the same enzymes (described in Persic et al. (1997) 187:9-18). The resulting plasmid, pABExpress40 contains both heavy and light chain cassettes with their respective transcriptional orientation in opposite directions, and the anti-repressor element positioned in the middle of the two transcription units. A schematic map of the plasmid is shown in FIG. 22. This plasmid, pABExpress40 is used first in the cloning of the one chosen VL gene (using ApaLI and Pad cloning sites), resulting in pABExpress40-VL. This plasmid is used to receive the VH repertoire described above (as BssHII-BstEII fragment) (all of these four sites are unique in pABExpress40 and pABExpress40-VL). The cloning of the repertoire is carried out as described for the lambda repertoire in Example 4, using in the PCR of IgM-primed cDNA a set of nine oligonucleotides labeled "VH-back" and the mix of four "VH-forward" oligonucleotides described in Table 1 of H. J. de Haard et al. (1999), *J. Biol. Chem.* 274:18218-18230. The material is re-amplified using variants of the nine oligonucleotides appended with 5'-TATC CGC GCG CAC TCC-3' (SEC) ID NO:45) and with the same VH forward mix, the product digested with BssHII and BstEII and cloned into pABExpress40-VL. The library is subsequently used as described in the previous examples to isolate panels of antigen-binding clones. Similarly the vector is used to construct the expression plasmid for given sets of antibodies, such as the ones described in Example 10, further confirming that the flanking variable region genes by anti-repressor elements facilitates the efficient and stable production of multiple antibodies by a single cell.

Example 12

Recovery and Analysis of Antibody Mixtures Using ELISA Including the Use of Anti-Idiotype and Peptide Mimotopes Antibody mixtures containing Fc regions are recovered as indicated in Example 3 using Protein A affinity chromatography. Antibody fragments with Histidine tags are isolated using IMAC as described in Example 2.

The resulting protein mixtures are analyzed as follows. First instance we consider the case of an antibody mixture composed of different binding sites directed to the same target antigen, with all antibodies being the same isotype, carrying the same light chain, and the mixture containing both monovalent bispecific and bivalent monospecific IgG-type antibodies. The following methods are available for analyzing the mixture. The heavy chain variable region genes will yield different amino acid compositions and allow the following non-antigen-dependent analysis: (1) Isoelectric focusing gel analysis: this analysis relies on a different pI value for the various forms of the antibodies. In a mixture of two IgGs and one bispecific, these three molecules will each display a unique isoelectric point. Proteins with a different pI are separated via electrophoresis in a pH gradient. The method is semi-quantitative. If two proteins of the complex have only a minimal difference in their pI value, it will be difficult to separate them using this test, and the other tests cited are used. (2) Mass-Spectrometry analysis: this analysis relies on the differential composition of the VH region, which, after digestion with proteolytic enzymes, yields a unique spectrum of peptides in MassSpec analysis. This method is predominantly qualitative. (3) Binding analysis based on anti-idiotype antibodies or peptide mimics: this analysis requires the availability of reagents that specifically recognize one antibody binding site in the presence of the other binding sites in the mixture. Suitable for this analysis are anti-idiotype antibodies which uniquely recognize the idiotype of the antibody. In this example where the antibodies share a common light chain, the unique features of the idiotype are formed mainly by the heavy chain determinants. Anti-idiotype antibodies are selected using the individual monoclonal antibodies as antigen in a selection of a large phage displayed antibody library using methods known to those in the art. Typically used are a non-immune antibody library (H. J. de Haard et al. (1999), *J. Biol. Chem.* 274:18218-18230), which yields Fab fragments, and a semi-synthetic phage antibody library (de Kruif et al. (1995) *J. Mol. Biol.* 248:97). Anti-idiotype antibodies are selected on immobilized M57 and JB antibodies from the cited non-immune antibody library. Using ELISA screening of the selected phage antibodies on these two monoclonal antibodies used for the selection, anti-idiotype antibodies that uniquely recognize one of the two binding sites are identified. The respective Fab and scFv reagents selected from these library, are expressed as antibody fragments and purified using standard methods, for example, described in these citations and in *Antibody Engineering* (2001), Eds. Konterman and Dubel, Springer Lab Manual, and described in Example 2 for the scFv antibodies. The fragments are used in ELISA to determine which idiotype is present in the mixture, which is carried out in a quantitative assay. The anti-idiotype antibodies specific for the binding sites of M57 and JB are also used in virus competition experiments with the Oligoclonics™ preparation made in Example 10, to delineate the contribution of an individual binding site to the biological activity of the antibody mixture. Alternatively, the monoclonal antibodies are used to derive idiotype-associated peptides, linear or conformational peptides derived from the sequence of the antigen and still reactive with the antibody, for example, via PepScan analysis, as was demonstrated for the rabies virus ~neutralizing antibody MAb 6-15C4 (van der Heijden et al. (1993), *J. Gen. Virol.* 74:1539-45). An alternative is to isolate peptide mimotopes, with sequences unrelated to the original antigen yet specifically binding to the variable regions of the antibody. Provided the reaction is specific for a given antibody in the context of the other antibodies in the mixture, such peptides are also suitable for a specific analysis of the antibody mixture. Peptides with such unique reactivity to a given antibody are selected from phage display peptide libraries using methods essentially similar to those for phage antibody libraries. The binding test with the anti-idiotype antibodies and peptide-mimotopes is qualitatively or quantitatively, and a large series of binding tests are feasible, including ELISA, RIA, Flow cytometric analysis, BIAcore, etc.

We also disclose the analysis of an Oligoclonics™ mixture comprising multiple antibodies, in which each of the original antibodies binds to a different antigen. This resembles the situation in which the antibodies recognize the same antigen or target, and anti-idiotype reagents or peptide mimics are available. The analysis of multiple specificities in a mixture is carried out as follows, keeping in mind that antigen is synonymous for anti-idiotype. The reactivity to individual antigens is tested in ELISA on all antigens separately, with standardized assays using the monoclonal antibodies and quantitative IgG ELISA test. Antigen is coated directly or indirectly, the plates incubated with the antibody mixture, and bound antibody detected with an anti-IgG reagent. This leads to a "specific" activity of the preparation, that is a reactivity in relative units of activity per antibody quantity. The amount of bispecific antibody in the mixture is determined using a sandwich assay with one antigen coated and a second antigen, preferably labeled with HRP, Alkaline Phosphatase or biotin, or detectable using another antibody specific for this antigen, provided to the plate after the antibody mixture was incubated with the first antigen.

If the antibodies present in the Oligoclonics™ mixture are binding different targets or different epitopes on the same target such that they are non-competitive, this feature can be used in an inhibition ELISA to determine the presence of the different antibodies in the mixtures produced by the transfected clonal cell lines. Consider an Oligoclonics™ made according to the methods of the previous examples using the antibodies specific for the Rabies glycoprotein isolated in Example 7 (which are non-competitive). For the inhibition ELISA, the same procedures as described for the standard anti-rabies ELISA as described above is used with some modifications. The Oligoclonics™ mixture produced by a clonal cell line is characterized as follows. Before addition to the wells coated with rabies glycoprotein, the supernatants of the transfected clonal cell line is diluted with an equal volume of a biotinylated rabies monoclonal antibody used to make the mixture. The biotinylated rabies monoclonal antibody is added in various concentrations, ranging from 0.1 to 10 μg/ml. Binding of the biotinylated monoclonal antibody to the coated rabies glycoprotein is inhibited when the same non-biotinylated antibody is present in the mixture produced by the clonal cell line. The binding of the biotinylated antibody is visualized with streptavidin, conjugated to an enzyme. As a control for binding and degree of inhibition, various concentrations of the biotinylated monoclonal antibodies diluted with an equal volume of culture medium without the mixture of antibodies or using the non-biotinylated antibody are used in the inhibition ELISA. This method is also suitable to screen the mixture of antibodies at a very early stage after transfection (as in Examples 10 and 11); thus, for each supernatant containing mixtures of antibodies, the presence of individual antibody specificities can be determined.

Example 13

Expression of Three Fab Fragments in the Same Eukaryotic Cell

For making a mix of these three antibodies, the expression experiment described in Example 10 is repeated using the following antibody genes, of the M57, JB and PO1 antibody (the latter is formed by the VH-PO1 and VL-PO1 genes of Example 9). Anti-idiotype reagents are separately selected on M57 and JB whole antibodies using a non-immune antibody library (see also Example 12). This yields anti-idiotype antibodies that react with either M57 or JB; these antibodies are also tested on the PO1 to confirm specificity for either M57 or JB idiotypes. Similarly, the PO1 antibody is used in similar selections to obtain an anti-Id reagent for the PO1 binding site. Next, the heavy chains of these three antibodies, M57, JB and PO1, are cloned as VHCH1 fragments into VHExpress while deleting the gamma-1 gene (thus encoding an Fd chain only), yielding pEU-VH-M57, pEU-VH-JB and pEU-VH-PO1. The light chains VL-M57=JB-CL and VL-PO1-CL are cloned into VKexpress (Persic et al. (1997) 187:9-18), while deleting the CK gene from the cassette. First the light chain plasmids are introduced into PER.C6 cells and a clone is selected that stably produces over 2 micrograms/ml of both light chains (using methods described in Example 10). This cell line, designated PL2-2, is subsequently transfected with the three heavy chain containing plasmids, and a large collection of cell lines is obtained that produce a variety of levels of antibody Land Fd chains. The best candidate mixtures are purified on protein G affinity chromatography and tested for binding and composition as described in the previous examples, and also using the anti-Id reagents as described in Example 12. The experiments provide confirmation that multiple Fab fragments, with appropriately paired variable region genes, are expressed as highly functional mixtures.

Example 14

Cloning and Expression of Three Antibodies Directed to Different Antigens as an Oligoclonics™ Mixture Using the methods of the previous examples, antibodies with the same light chain are isolated against three different antigen, TNF-alpha, Interleukin-1beta (IL-1beta) and Interleukin-6 (IL-6), using a semi-synthetic library scFv library from Example 7 and described in (de Kruif et al. (1995) *J. Mol. Biol.* 248:97). In the selection, biotinylated recombinant cytokines (purchased from R&D Systems), are used, at decreasing concentrations during selection (250 nM, 100 nM and 50 nM). From the panels of antibodies generated against each of the targets after three rounds of selection, those scFv antibodies that neutralize the activity of the cytokine are identified. For this, the antibody fragments are recloned into pSCFV and purified using IMAC as in Example 2. Biological assays used are well known to those skilled in the art and include a L929 neutralization assay for TNF-alpha. Neutralizing clones are identified against TNF-alpha, IL-1beta or IL-6. The potency of neutralization can be improved by further affinity maturation techniques. For example, the CDR1 and CDR2 of the VH can be mutagenized and variants selected using phage display and tested for improved neutralization activity. These three antibodies have an identical light chain and have heavy chain variable regions that are distinct from one another, with most changes located in the CDR3.

The antibody variable regions are cloned into the eukaryotic expression described in Example 10, and essentially following the same procedure, CHO-cell lines identified that express mixture of the one light chain and three heavy chains. The analysis of the mixtures is carried out using ELISA to demonstrate binding to three antigens in a subset of the cell lines identified. A clone stably producing all three antibodies in an approximate ratio of heavy chains of 2:1:1 is identified using the techniques described in Examples 10 and 12. The cell lines are expanded and the mixture purified on Protein A and extensively tested to determine its composition. Using ELISA tests in various formats, with indirectly coated biotinylated antigen, with directly coated antigen 1, adding sample, followed by biotinylated antigen 2 and detection with Strep-HRP, and using samples of the mixture that have been depleted on TNF, IL-1beta or IL-6-coated beads, is it shown that the mixture contains three monospecific antibodies and three bispecific antibodies. The exact ratio between these six components is established by using quantitative ELISA tests and by IEF analysis of the mixture, as shown in Example 12. The neutralization efficacy of the mixture for the individual cytokines was confirmed with the assays as tested before. The neutralization of these cytokines in more complex systems, for example, using mixed cell populations, may establish a synergistic effect of the neutralization of these components by the Oligoclonics™ mixture.

Example 15

In Vitro Pairing of Antibody Chains Produced in Different Cells to Form Defined Antibody Mixtures Alternatively, to the expression in one host cell, antibody mixture can also be assembled ex vivo. The chains can be expressed separately and combined with a set of potential partner variable regions for pairing and assembly of the molecule.

In this prophetic example, a mixture of Fab fragments with pairing-compatible variable regions will be made as follows. The heavy chain variable regions of M57, JB and PO1 (Example 9) will first be cloned separately into an appropriate pET expression plasmid, such that this will mediate the expression of the Fd chain tagged with six Histidines inside the *E. coli*, as inclusion bodies. A suitable vector can be found in Novagen's pET Table, such as pET21d+ (see also http://www.novagen.com/Includes/wrapper.asp?href=/SharedImages/Novagen/pETtable.htm§ion=TechResources&subsectjon=TechLit&strsubsection=techresources). The cloning will then be carried out by PCR of the VHCH1-containing templates (from Example 9) using oligonucleotides to provide appropriate cloning sites and also the C-terminal Histidine tag. These three plasmids will be introduced into separate *E. coli* host cells. The expression of the Fd fragments can then be induced and the protein demonstrated to be present in inclusion bodies. The two light chain variable regions, VL-M57=JB and YL-PO1 can also be suitably cloned into a suitable pET vector (although, alternatively, they could be obtained by secretion from a secretion vector like pFab-sol-pbr). After expression of the separate light chains, they should also be retrievable from the intracellular fraction. To assemble the mixture of three functional Fab fragments, the following procedure can then be followed. First the approximate and relative quantities of the individual L or Fd chains is estimated by gel-electrophoresis and Western blot. Then five 50-ml cultures of *E. coli* carrying one of five antibody variable regions are grown and induced as described in the pET manual from Novagen. After induction and growth, the pelleted cells of each of the chains can be resuspended in 8 ml 8 M urea (in PBS). After sonication, the five suspensions would be mixed in a ratio of approximately 1:1:1:4:2 for VH-M57, VH-JB, VH-PO1, VL-M57=JB, VL-PO1 (thus with a two-fold excess of light chain over heavy chain, and more of the twice needed VL). After this mixing of the denatured heavy and light chain variable regions, the mix will be rotated head over head for two hours. Insoluble material may then be removed by centrifugation for 30 minutes at 13,000×g. The supernatant is dialyzed against PBS with four buffer changes, and insoluble protein further removed by centrifugation. The flow through fraction, obtained by filtration through a 0.2 μm membrane, should contain the refolded antibody mixture with pairing-optimized chains. The mixture may be further concentrated and purified, first using IMAC, which should retrieve all heavy chains and their paired light chains, followed by semi-preparative gel-filtration on a Superdex 75HR column (Pharmacia). The yield may be determined by measuring the optical density at 280 nm (using a molar extinction coefficient of 13 for Fabs). The mixture may be further characterized by analyzing the binding to the Rabies antigen. Since all functional Fabs should bind this antigen, a straightforward capture assay with antigen may be performed to determine the level of functional binding sites. There are many alternative protocols to this procedure, including the use of other extraction methods, other denaturation reagents, renaturation conditions and buffers, etc. Alternatively, to this procedure, both chains may also be secreted, and re-assembled using the conditions described by Figini et al. (1994) *J. Mol Biol.* 239:68-78.

Example 16

Screening Antibody Mixtures Targeting Murine Vascular Endothelial Growth Factor The antibodies used in this example are described in WO 03102157A2 (inventors Fuh and Sidhu). The antibodies were derived by in vitro selection of a display library in which only the heavy chain was diversified. The repertoire with a fixed light chain and variable heavy chain was selected on murine vascular endothelial growth factor (mVEGF) and a large panel of antibodies binding mVEGF identified (Sidhu et al., *J. Mol. Biol.* 2004, 338:299-310). The source of the antibody heavy and light chain variable genes used in the repertoire was the humanized antibody 4D5. Antibody 4D5 is a humanized antibody specific for a cancer-associated antigen known as Her-2 (erbB2). The antibody includes variable domains having consensus framework regions; a few positions were reverted to mouse sequence during the process of increasing affinity of the humanized antibody. The sequence and crystal structure of humanized antibody 4D5 have been described in U.S. Pat. No. 6,054,297, Carter et al., *PNAS* 54:4285 (1992); the variable region sequences of the heavy and light chains are also given in FIG. 14 and SEQ ID NO:23 of WO 03102157A2; finally the crystal structure of 4D5 is shown in *J. Mol. Biol.* 229:969 (1993) and online at www.ncbi.nih.gov/structure, structure 1FVE.

An Oligoclonics™ mixture consisting of four different mVEGF-binding antibody binding sites is obtained as follows. Antibodies with clone numbers 4, 69, 73 and 74 as in Table 6, page 306 of Sidhu et al., *J. Mol. Biol.* 2004, 338:299-310, were selected on the basis of mVEGF binding as scFv on phage and as Fab protein (same Table 6). The antibodies share an identical light chain (of the Herceptin antibody, 4D5; as described in WO 03102157A2), but have differences in their heavy chain amino acid sequence as depicted in Table 6 of this paper.

The h4D5 antibody is a humanized antibody that specifically recognizes a cancer-associated antigen known as HER-2 (ErbB2) developed as described previously. The h4d5 VL gene is obtained by polymerase chain reaction using the humAb4D5 version 8 ("hurnAMD5-8"; Carter et al. (1992) *PNAS* 89:4285-4289) sequence and primers engineered to give rise to a 5' ApaLI site and a 3' PacI site in the PCR product. The PCR product was cleaved with ApaLI and PacI and ligated into the pABExpress vector (the vector described in Example 11 and in FIG. 23 but without the STAR40 sequence cloned into the EcoRI site). This yields plasmid pAb-4D5-VL, which encodes the expression of a functional 4D5 light chain (with human Ckappa constant region), and contains a polylinker region suitable for cloning VH regions. The VH regions from clones 4, 69, 73 and 74 are then cloned into this vector, using BssHII and BstEII restriction sites, and following the cloning route described in the previous examples (by providing the nucleotides encoding these restriction sites into the PCR primers in such manner that the cloning will yield an in-frame insertion encoding a fully functional antibody variable domain). This yields plasmids pAb-IgG-04, pAb-IgG-69, pAb-IgG-73 and pAb-IgG-74.

These plasmids encoding heavy and light chains are transfected into the human cell line PER.C6™ to generate stable cell lines secreting multiple of the mVEGF-binding antibodies. For this, published methods and methods known to persons skilled in the art are used (E. Boel et al. (2000). *J. Immunol. Methods,* 239:153-166 and WO 00/63403). For the generation of stable PER.C6™ cells secreting antibodies, PER.C6™ cells are seeded in DMEM plus 10% FCS and in tissue culture dishes (10 cm in diameter) or T80 flasks with approximately $2.5\times10^6$ cell per dish or flask and kept overnight in an incubator at 37° C. and 10% $CO_2$. The next day, transfections are preformed in separate dishes at 37° C. using Lipofectamine (Invitrogen Life Technologies) according to standard protocols provided by the manufacturer. The plasmids pAb-IgG-04, pAb-IgG-69, pAb-IgG-73 and pAb-IgG-74 are mixed in a 1:1:1:1 ratios and used at a concentration of 2.5 μg/ml each. As controls, cells are subjected to the transfection procedure in the absence of plasmids, or with just a single plasmid. After four to five hours, cells are washed twice with DMEM and fed with fresh culture medium. The next day, the culture medium is removed and cells are fed with fresh medium containing 500 μg/ml of the antibiotic G418. Cells are fed every two to three days with culture medium containing 500 μg/ml of G418. After about 20 to 22 days after initiation of the experiment, a large number of colonies is visible and from each transfection, 400 clones are picked and grown individually in 96-well plates and further expanded in 24-well, 6-well and T25 flasks. At this stage, cells are frozen in liquid nitrogen and production levels of recombinant immunoglobulin are determined in an ELISA according to standard procedures (e.g., E. Boel et al. (2000), *J. Immunol. Methods,* 239:153-166 and WO 00/63403). At this stage of the culture procedure, G418 is no longer added to the culture medium.

To establish the presence of at least one functional anti-mVEGF antibody in a clone's culture supernatant, a solid phase ELISA is performed. Plates (PolySorb™, Nunc) are coated with 2.5 μg/ml of mVEGF (R&D Systems, recombinant Mouse VEGF120 and VEG164, both carrier free) diluted in PBS and 100 μl/well overnight at 4° C. The plates are then blocked with 2% BSA in PBS for two hours and washed in PBS containing 0.05% Tween20 (PBS-Tween) prior to the addition of cell supernatant samples containing antibodies. Following incubation at room temperature for two hours, the plates are washed with PBS-Tween to remove unbound antibody present in the supernatant samples. Horseradish peroxidase-conjugated anti-human IgG is then added in PBS for one hour at room temperature and the plates are subsequently washed with PBS-Tween (2×) and PBS (2×). Detection of secondary antibody is performed according to standard procedures and the absorbance determined spectrophotometrically (see also previous examples). It is found that of the 400 clones screened, a substantial fraction produces a minimal IgG quantity.

Since only a limited number of colonies secrete a mixture of the four mVEGF antibodies, 50 clones selected from the initial panel of approximately 400, that are strongly reactive in the IgG-ELISA, clonality is further established by subcloning under limiting dilution. Picked and expanded colonies are seeded in a 96-well plate at a concentration of 0.3 cells/well in DMEM with 10% FCS and expanded. Colonies of cells are processed as described above and are referred to as subclones. While the initial transfection experiment used a ratio of DNA for the four plasmids pAb-IgG-04, pAb-IgG-69, pAb-IgG-73 and pAb-IgG-74 of 1:1:1:1, the cell subclones still display a variety in the expression levels for each of the antibodies. This is due to their independent expression regulation and their random integration into the genome. Further, since the same selection marker is used on all plasmids, the subclones express at the most four antibody binding sites, but not necessarily all four of them. The precise number depends on the transfection experiment; approximately 20-30% of the Ig-reactive clones express multiple antibody heavy chains, and of these, approximately 20% express more than two antibody heavy chains. The methods to increase these frequencies have been described earlier herein.

Screening to find the most optimal mixture of these four mVEGF-binding antibodies, as Oligoclonics™ mixture with bivalent and bispecific components, is done as follows. Optimal mixture here means with regards to which of the four antibody binding sites are optimally present in the mixture, and at which ratio they should be present. For the 50 subclones as well as for one IgG-reactive clone from the control transfectants made with just one antibody encoding plasmid, larger volumes are cultured to purify the recombinant human IgG1 fraction from the conditioned supernatant. This is done using Protein A affinity column chromatography according to standard procedures (Ed Harlow and David Lane, *Using Antibodies, A Laboratory Manual,* 1999, ISBN: 0879695447). These mixtures and the monoclonal antibody controls are tested for their neutralization activity on mVEGF in a $^3$H-thymidine incorporation assay using human umbilical vein endothelial cells (Conn et al., 1990, *Proc. Natl. Acad. Sci. U.S.A.* 87:1323-1327). The inhibitory activity of each of the mixtures is compared to the inhibitory capacity of the four individual monoclonal antibodies. Mixtures that display a higher inhibitory activity on a molar basis compared to the activity of the monoclonal antibody controls putatively contain multiple antibodies that in combination mediate a synergic effect on the activity of VEGF. Next, assays that indicate the binding to mVEGF, the affinity of the interaction of the mix, the competition in binding with receptor (Flt-1 and KDR-1), are used. A binding assay is described above (solid phase ELISA). Assays to determine the relative affinity of the mixes are described in Sidhu et al., *J. Mol. Biol.* 2004, 338: 299-310, page 308 (affinity measurements by competitive ELISA), with Fab and phage-displayed antibodies replaced with the mixtures of antibodies or the monoclonal antibodies as controls. An increase in relative affinity indicates a strong synergistic activity between the antibodies in the mixture, as described in Marks, *Movelent Disorders*, vol. 19, suppl. 8, 2004, p. S101-S108, for antibody mixtures binding to non-overlapping epitopes of neurotoxins. Other assays to demonstrate the activity of the mixture of the antibodies on VEGF either in vivo or in vitro, are well established in the field and are, for example, described in WO 03102157A2, EP 0666868B1 and WO0044777A1.

Since VEGF displays activities in many processes, including mitogenesis, angiogenesis, endothelial cell survival, induction of metalloproteinases and growth factors, regulation of permeability/flow, recruitment of endothelial progenitor cells etc, any other single assays or combinations of assays can be used to determine the effect of the antibody mixtures on the activity of VEGF. The antibody mixtures can be screened in any of these assays, or combinations of assays, to find those compositions that have an effect in a defined set of assays, or have an effect in one but not in another assay. Further or instead of the in vitro assays, in vivo assays can be used to measure the overall effect of the antibody mixture on the pharmacokinetics of the antigen, and demonstrate improved clearance as mechanism of the synergic activity of the multiple antibodies in the Oligoclonics™ mixture.

Mixtures are further characterized biochemically to find which antibodies are present and in which ratio, as described in Example 12.

Example 17

Pairing-Compatible Antibodies for Producing a Mixture of HER2/ErbB2-Targeting Molecules Trastuzumab (Herceptin, or h4D5, or hu4D5, see Example 16) and pertuzumab (Omnitarg, humanized 2C4) are both recombinant monoclonal antibodies that target different extracellular regions of the HER-2 tyrosine kinase receptor. Recently, it was shown that these antibodies synergistically inhibit the survival of breast cancer cells in vitro (Nahta et al., *Cancer Research* 64:2343-2346, 2004). Herceptin is active against HER-2 overexpressing metastatic breast cancers, leading to its approval in 1998 by the US FDA. In contrast to Herceptin, pertuzumab sterically blocks HER-2 dimerization with other HER receptors and blocks ligand-activated signaling from HER-2/EGFR and HER-2/HER-3 heterodimers. On the other hand, trastuzumab blocks ErbB2 shedding while pertuzumab does not. Mixtures of antibodies directed to the same target antigen but that display different or non-overlapping mechanisms of action will be very valuable in the therapeutic arsenal, and production of such multiple antibodies in a commercial manner will become very important. In this example, we describe how pairing-compatible versions of these two antibodies are isolated, and used to build an Oligoclonics™ with an expected increase in potency and efficacy in tumor cell killing compared to the original monoclonal antibodies.

Anti-HER2 antibodies 4D5 and 2C4 are described in WO 0100245A2 and in Fendly et al., *Cancer Research* 50:1550-1558 (1990). The molecular structure and sequence of the humanized version of antibody 2C4 is described in Vajdos et al., *J. Mol. Biol.* 2002, 320, 415-428, in PDB database reference 1L71, and in WO 0100245A2 (version 574 in Table 2 on page 54, or rhuMAb2C4 in continuation of this document). For simplicity here "2C4" is used to indicate the humanized version 574 of the murine 2C4 antibody. Its structure, in complex with the first three domains of ErbB2, was recently published (Franklin et al., *Cancer Cell*, 5, 2004, 317-328. The structure and sequence of h4D5 or Herceptin was described by Cho et al., *Nature* 2003, 421, 756-760, and is deposited as 1N8Z in the PDB database. Outside of the complementarity-determining regions (CDRs), pertuzumab is identical in sequence to trastuzumab (Carter et al., *Proc. Natl. Acad. Sci. U.S.A.* 89, 4285-4289, 1992); consequently, the local structure of the pertuzumab Fab in the ErbB2-pertuzumab complex is expected to be largely the same as that of the trastuzumab Fab. To build a pairing-compatible single light chain that will restore a functional binding site when paired with the h4D5 VH but also when paired with the 2C4 VH, the following route is followed.

Designing Pairing-Compatible Light Chains

The amino acid differences between the light chains of hu4D5v8 (the humanization variant described by Kelly et al., 1992, supra, indicated by hu4D5 or h4D5 in the next section) and 2C4 have been mapped to be 11 residues as highlighted in FIG. 23. In the CDR regions of the light chains, there are four differences in CDR1, three in CDR2 and four in CDR3. In most straight forward to follow in the absence of structural data on the antibodies and their interaction with antigen, is to build a library of light chain that have been diversified at these positions, and screen or select for variant light chain that maintain antigen-binding behavior when paired with the heavy chains of both antibodies, h4D5 and 2C4. The diversification can be chosen to contain all possible 20 amino acids or a subset thereof, for example, all residues but cysteine (which is not normally occurring at these 11 positions), or a selected set of amino acids that frequently occurs in antibodies at these positions. The design of a light chain repertoire based on all 11 amino acid differences between h4D5 and 2C4 is given in FIG. 23, in line HYB1.

A second approach to build a pairing-compatible variable hybrid light chain region for two antibodies, is to further employ structural information on the interaction of the antibodies with their respective antigen or antigens. In the example of h4D5 and 2C5, a wealth of structure-function information is available to guide the design of a hybrid light chain library. In this design, HYB2 in FIG. 23, all the light chains in the designed repertoire retain all of the common residues between the two original light chains of hu4D5 and 2C4, and a selection of residues at the positions where the original two light chains differ in composition, in which the selection is based on structural information on the antibody-antigen interaction. While some of the design may be based on this information, it is also noted that point mutations of h4D5 have been shown to dramatically effect the biological behavior of the antibody. The antiproliferative activities of the humanized variants of 4D5, which differ only in maximally seven amino acid residues, were found not to be strongly correlated with antigen affinity (Kelley et al., 1992, supra).

Thus, it will be required to sample multiple versions of pairing-compatible light chains, and test the biological activity of the combinations after the antigen-selection and binding characterization to ensure maintenance of the biological activity.

The following HYB2 library design was made, based on the following observations:

CDR1. The sequence plasticity of the antigen-binding site of Herceptin was analyzed in a study by Gerstner et al. (*J. Mol. Biol.* 2002, 321:851-862). From these studies it appears that for trastuzumab residues N30 may be readily replaced by Serine (Table 1, Class 1 mutation VL30, of Gerstner et al., supra). Serine is the residue used at this position by 2C4. Thus, the pairing-compatible hybrid light chain is designed to contain Ser at position 30. The rest of the CDR1 is taken from the Herceptin light chain, as this region appears to be irrelevant for antigen binding in 2C4 (Franklin et al., supra).

CDR2. By alanine-scanning and homolog-scanning of the Fab2C4 antibody it was revealed that most of the side-chains that contribute to antigen binding are located in the heavy chain (Vajdos et al., supra). This was recently confirmed by the crystal structure of the antibody in complex with antigen: the light chain of pertuzumab Fab makes only a few contacts with ErbB2, mostly via CDR L2 (possibly via residue 55) and some via L3 (Franklin et al., supra). Some of 2C4's residues in this region may be converted to h4D5's residues without loss of affinity, as suggested by experiments with humanized versions of 2C4 described in WO 0100245A2 (page 54), in particular, what may be possible is to choose h4D5's VL's residues at positions 54 and 56. The Phe at position 53 in Herceptin appears to be relatively conserved, with some presence of Trp, while the other positions in this CDR region were not tested. Since some of these CDR2-based residues may also be important for positioning neighboring heavy-chain-based residues for antigen binding, in the hybrid light chain design, the three residues which are different between h4D5 and 2C4 are diversified fully, such that the selection process can identify which of the 8000 combinations will yield a pairing-compatible light chain.

CDR3. Tyrosine 91 of 2C4 is said to be important for antigen binding (Franklin et al., supra) but its substitution with phenylalanine (F) is acceptable (Vajdos et al., supra). Herceptin at this position in the light chain besides its original residue histidine tolerates several other aromatic side chains including Phe, Tyr and Trp (Table 1, page 854 in Gerstner et al., supra). Thus, the hybrid light chain is designed to contain Phe at position 91 (FIG. 23). For 2C4 antigen binding of the other residues of the H3 loop is relatively resistant to mutagenesis as in Gerstner et al., with the exception of the Pro at position 95. But this residue is shared between the Herceptin and 2C4 antibody light chains. In the interaction of Herceptin with antigen there are more likely interactions of the CDR3 regions with antigen, thus in the hybrid light chain, all but residue 91 is taken from Herceptin-VL (FIG. 23).

In the final HYB2 design, amino acids are taken for 6 out of 11 positions from the h4D5 VL, 1 out of 11 from the 2C4 VL (pos. 30), one is a residue not found in either VL (pos. 91) and the three are to be randomized (in CDR2).

HYB1 Library Construction and Selection of Pairing-Compatible VLs

The two libraries of light chains are constructed as follows. In the HYB1-designed VL library, 11 residues are randomized, implying that the total theoretical amino acid diversity (20exp11) is much larger than can be readily screened. To sample the diversity in this library, a powerful selection method is, therefore, used. The heavy chains (VH) of h4D5 and 2C4 are cloned into the SfiI-BstEII cloning sites from pCES1 (de Haard et al., 1999, *J. Biol. Chem.* 274, 18218-30) using PCR and oligonucleotides binding to the 5' and 3' end of the nucleotide sequences of the VH genes and introducing SfiI and BstEII sites at appropriate sites for in-frame cloning (as described for antibody VH genes in de Haard et al., supra; the BstEII site is already present in the JH region of both h4D5-VH and 2C4-VH). The template for the PCR of the VH of h4D5 is plasmid pAK19 carrying the humanized 4D5 variant number 8, hu4D5-8, described in Kelly et al., 1992, *Biochemistry* 31:5435-5441, Table 1. The nucleotide sequence of this clone is essentially described in Carter et al. 1992, *P.N.A.S.,* 89:4285-4289, in FIG. 1, as huMAb4D5-5, with two alterations (V102Y in CDR3 of the VH, and E55Y in CDR2 of VL, as described in Kelly et al., 1992, supra). The VH sequence can also be extracted as SfiI-BstEII fragment from SEQ ID NO:17 as described below. The template for the PCR reaction of the VH of 2C4 is plasmid pC2C4, described on page 425 of Vajdos et al., supra. The VH sequence can also be extracted from the NcoI-BstEII insertion inside the larger BssHII-NotI-fragment from SEQ ID NO:17. The cloning of the PCR products into pCES1 is carried out as described for human antibody heavy chain VH pools and using standard cloning procedures. pCES1 is a phagemid vector that is suitable for the expression of Fab fragments in *E. coli* and for the display of Fab fragments on the surface of filamentous phage (de Haard et al., 1999, supra). Two plasmids with correct insert are identified by sequencing the insertion and junction region and the resulting plasmids named pCES-VH-h4D5 and pCES-VH-2C4. These are the acceptor plasmids for the light chain repertoire, HYB1. The VLCL coding region of hu4D5v8 is amplified using specific oligonucleotides priming in its 5' and 3' region and introducing ApaLI and AscI restriction sites as described in de Haard et al., supra, for human VLCL chains. As template pAK19 carrying the humanized 4D5 variant number 8 (hu4D5-8, described in Kelly et al., 1992, *Biochemistry* 31:5435-5441, Table 1) is used. The PCR product is cloned as ApaLI-AscI fragment in pCES-WI-h4D5, to yield pCES-Fab-h4D5. This encodes a functional h4D5 Fab fragment. HYB1 is produced using described methods with "stop" template versions of this plasmid. The stop template version is made by replacing one codon in each of the CDR1, CDR2 and CDR3 of the hu4D5-v8-VL with TAA stop codons. Methods to diversify the VL-template have been extensively described in the literature including in WO 03102157A2, in *Directed Mutagenesis, a Practical Approach*, Ed. M. J. McPerson, IRL Press 1991. The method used here is the Kunkel method; this yields the stop template of the VL in plasmid pCES-Fab-h4D5-3ST. The stop template version of h4D5-VL is used as a template for the Kunkel mutagenesis method (Kunkel et al. 1987, *Methods in Enzymol.* 154:367-382), using mutagenic oligonucleotides designed to simultaneously repair the stop codons and introduce mutations at the designed sites. Mutations in all three CDRs of the VL are introduced simultaneously in a single mutagenesis reaction. This is extensively described in Sidhu et al. 2000, *Methods Enzymol.* 328:333-363. The mutagenesis reaction is electroporated into *E. coli* SS320 (Sidhu et al., supra), and the transformed cells are grown overnight in the presence of M13-VCS helper phage to produce phage particles that encapsulated the phagemid DNA and displayed Fab fragments on their surfaces. Methods for phage-display library manipulation, selection and screening of clones have been described in the literature, for example, see de Haard et al., supra; Vajdos et al., supra and also the other examples). The resulting 4D5-HYB1 library contains greater than $1\times10^8$ unique members. This 4D5-

HVB1 library is selected twice on HER2 antigen as described in Vajdos et al., supra, to yield a population of more than 65% of antibodies with antigen-binding activity. These antibodies share their VH region, but most carry different light chains. The light chains of this population are obtained as ApaLI-AscI fragment (VLCL), and cloned as a pool into pCES-VH-2C4. This new library now contains a subset of the light chains of HYB1 that are likely to be compatible with antigen binding in the context of h4D5. The library is selected once on antigen, and clones identified that mediate antigen binding. Light chains with identical amino acid sequence and that mediate antigen-binding when paired with the h4D5-VH and with the 2C4-VH are identified by sequencing a panel of Ag-reactive clones from the selected h4D5-HYB1 library, and of Ag-reactive clones from the selected 2C4 sublibrary, and comparing the sequences. Besides using antigen-reactivity in phage ELISA as readout, the reactivity of the Fab fragments is tested in ELISA (as described in de Haard et al., supra). This leads to the identification of a panel of VLs that display are functionally pair with both VH-h4D5 as well as VH-2C4. Within the panel the best VL is identified by determining the affinity of the interaction and the biological activity of the two respective Fab fragments. Methods for affinity determination and biological activity of anti-HER2 Fabs are described in Kelley et al., 1992, supra, and Gerstner et al., 2002, supra, and are described further below.

HYB2 Library Construction and Screening of Pairing-Compatible VLs

Figure 24:
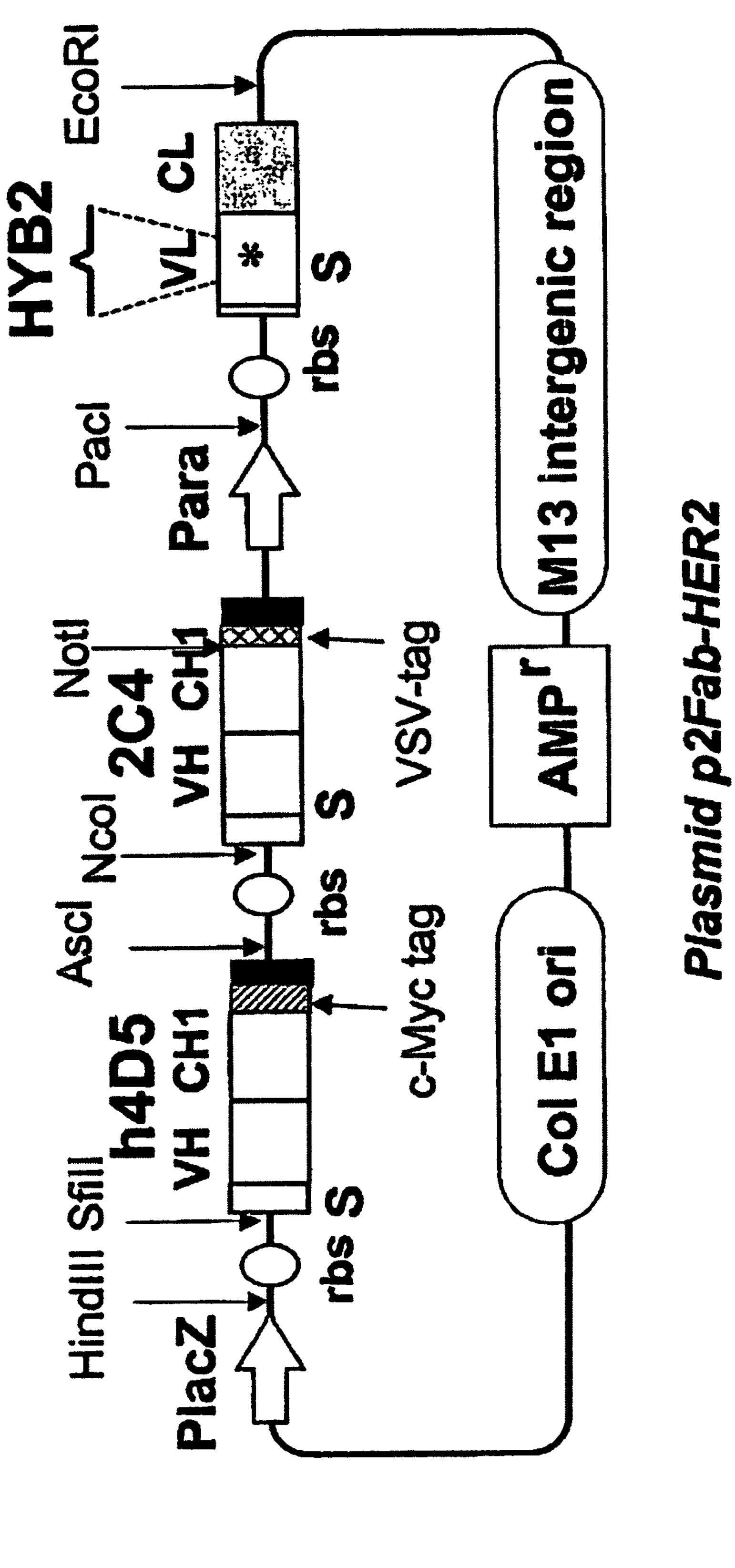
FIG. 24: Plasmid p2Fab-HER2 used for the identification of a light chain variable region that is pairing-compatible with two HER2-binding antibodies, h4D5v8, and 2C4. The black box is a schematic depiction of the histidine tag (six Histidines); other C-terminal-based tags are also indicated. S, signal sequence; rbs, ribosome binding site; $AMP^r$, ampicillin resistance gene (beta-lactamase). The version of the VL of h4D5 that is present in this vector carries two designed mutations in two CDR residues, and a stop codon (indicated with *) in the CDR2 region. By site-directed mutagenesis, the CDR2 is diversified using an oligonucleotide (designed according to approach HYB2) that simultaneously removes the stop codon as well as introduces diversity at three positions of the CDR2. This plasmid directs the expression of two antibody heavy chains (as Fd chains) and one antibody light chain, and thus allows simultaneous production, and individual detection, of two Fab fragments.

The HYB2-designed VL library contains 8000 variants only. Here a different route is followed to allow simultaneous expression, and detection of antigen-binding variants, of h4D5 and 2C4 WI containing antibodies. First, the VL in pCES-Fab-h4D5 is mutated by Kunkel site-directed mutagenesis (Kunkel et al., supra) with Asparagine 30 changed to Serine (N30S), and Histidine 91 changed to Phenylalanine (H91F), according to the design depicted in FIG. 23. Of the resulting clone, p4D5-VLmut, phage and Fab are produced and tested for binding in a dilutions series for binding to Her-2 (extra-cellular domain) coated plate phage ELISA, to confirm that h4D5 maintains a minimal antigen-reactivity. Next a stop-template version is made from this plasmid, by replacing one codon in the CDR2 of the VL with a TAA stop codon (residue 55, tyrosine is mutated from "tat" to "taa"; this residue is said to be required in order to attain the antigen affinity of the humanized h4D5 antibody, Kelley et al., 1992, supra, thus will need to be fixed to "Y" to restore the reading frame and antigen-binding), This stop template version of the light chain of h4D5v8 is cloned into pSCFV-3 (Example 2 and FIG. 14B), by amplification of the VLCL region from the CDR2 stop-template. The design of the oligonucleotides used in this amplification is such that the whole VLCL segment is amplified and that after digestion the segment can be directionally cloned for in frame expression of the light chain under control of the arabinose promoter of pSCFV-3, and without any C-terminal tags. Briefly the VLCL is amplified with primers binding to the 5' and 3' end of the cassette and at the 5' providing a long overhang in two PCR reactions to encode a region of approximately 90 nucleotides encoding ribosome binding sites, start codon and bacterial leader sequence, to produce an EcoRV-EcoRI fragment that is cloned into the PacI-EcoRI sites bordering the third expression cassette in pSCFV-3. This plasmid, pVLmutST, is used as acceptor for the two heavy chains, after an internal BstEII site at position 143 of the insert was removed. The sequence of the final PacI-EcoRI insert is given in SEQ ID NO:16. The heavy chains 2C4 and h4D5v8 are cloned in two steps as VH-CH1 fragments into pSCFV-3 (FIG. 14B) to yield plasmid p2Fab-HER2 as indicated in FIG. 24. First the h4D5 VHCH1 region is amplified from pCES-WI-h4D5 and cloned as SfiI-BssHII fragment into pVLmutST. The design of the primers is such that they, after cloning, arrange appropriate reading frames with leaders and tags in pSCFV3, to yield the final junctional sequences as depicted in SEQ ID NO:17. Secondly, the 2C4 heavy chain VHCH1 is amplified from pCES-VH-2C4 and cloned as BssHII-NotI fragment into this plasmid. Similarly, the design of the primers is such that they, after cloning, arrange appropriate reading frames with leaders and tags in pSCFV3, to yield the final junctional sequences as depicted in SEQ ID NO:17. This final plasmid, p2Fab-Her2, provides the expression of both heavy chain variable domains as Fd chains (linked to human gamma-1), and the expression of a yet stop codon containing light chain. The sequence of the HindIII-NotI and PacI-EcoRI inserts of p2Fab-HER2 is given in SEQ ID NOS:17 and 16, respectively. The heavy chains of the two humanized antibodies, h4D5-version 8 and 2C4-version 574 are provided as fusions to the human CH1 domain, the Myc and VSV tag, respectively, and a HIS-tag for IMAC purification. The light chain in format VLCL is essentially derived from h4D5 but carries two designed VL mutations at positions 30 and 91, a stop codon in the CDR2, and has an internal BstEII site removed without amino acid change.

Plasmid p2Fab-HER2 is used as a template for the Kunkel mutagenesis method (Kunkel et al. 1987, *Methods in Enzymol.* 154:367-382), using mutagenic oligonucleotides designed to simultaneously repair the stop codon in the VL-CDR2 and introduce mutations at the three designed sites in CDR2, as indicated in FIG. 23. After electroporation and plating (as before), a small library of 50,000 clones is screened for pairing-compatible VL versions as follows. In the plasmid p2Fab-HER2, all three variable region genes are linked to a unique epitope tag that provides a way for their specific detection. Individual clones are picked into 96-well plates (Nunc) and induced to express both heavy chains and the one light chain, using conditions as described in Example 4, with the exception that arabinose is also added as inducer at the same time as the IPTG. The next day the supernatant of the cultures is tested for the presence of HER2 reactive Fabs, in an ELISA essentially as in Example 4. Multiple assays are carried out with the same sample, using either anti-myc or anti-VSV secondary reagents to detect the presence of the h4D5-Fab or the 2C4-Fab, respectively.

A dual-reactive clone designated 3-8E3, which binds HER-2 in ELISA with both the anti-VSV and anti-Myc tag reagents, is chosen for further analysis. The Fab mixture of this clone is expressed to 10-L scale level and purified from *E. coli* Supernatants according to Kelley et al., 1992, supra, page 5435-5436. Briefly, the culture supernatant is microfiltered by tangential flow filtration, concentrated by ultrafiltration and filtered over DEAE-Sepharose-FF. The antibody mixture in the flow-through fraction is subjected to affinity chromatography on Protein-G-Sepharose-FF. The Fab mixture is eluted with 0.1 M glycine, pH 3.0. The total protein concentration is determined by $A_{280}$ measurements using an $\epsilon_{280}$ of 67 $mM^{-1}$ $cm^{-1}$.

The binding constant of individual Fabs or the apparent binding constant of the Fab mix are measured by ELISA essentially as described by Vajdos et al., 2002, supra, on page 426. Briefly, NUNC 96-well maxisorb immunoplates are coated overnight at 4° C. with HER2-ECD (1 microgram/ml in 50 mM carbonate buffer, pH 9.6), and the plates blocked for one hour at room temperature with 0.5% BSA in PBS-0.05% Tween 20. Serial dilutions of Fab protein are incubated on the HER2-ECD coated plates for two hours at room temperature, and the plates washed. Bound Fab is detected with biotinylated murine anti-human kappa chain antibody following by streptavidin—horseradish peroxidase conjugate (Sigma), using 3,3',5,5'-tetramethyl benzidine (TMB) as substrate (Kirsgaard and Perry Laboratories, Gaithersburg, Md.). The actual binding constant of one Fab in the mixture of two Fabs is measured by replacing the biotinylated murine anti-human kappa chain antibody of the above test with biotinylated anti-MYC-tag (for h4D5) or biotinylated anti-VSV tag (for 2C4) antibodies (antibodies similar to those described in Example 2). Titration curves are fit with a four-parameter non-linear regression curve-fitting program (KaledaGraph, Synergy Software) to determine the EC50 values, the Fab concentrations corresponding to half-maximal binding signals. Examples for h4D5, 2C4 and the 3-8E3 mixture is given in FIG. 25. The 3-8E3 mix is confirmed to contain two functional Fab antibody fragments, h4D5* and 2C4*, in which the * indicates that the light chain variable region is different from the two original humanized light chains of h4D5 and 2C4 (in FIG. 24), The ratio of the two Fab antibodies that are present in the 3-8E3 mix is analyzed by electrospray-ionization mass spectrometry essentially as described in Kelley et al., 1992, supra. There is a difference in the molecular weights of the Fabs on the basis of the heavy chains of 2C4 and h4D5 differing in approximately 68 dalton, well above the standard deviation of the assay (in the range of three to seven dalton).

Figure 25:
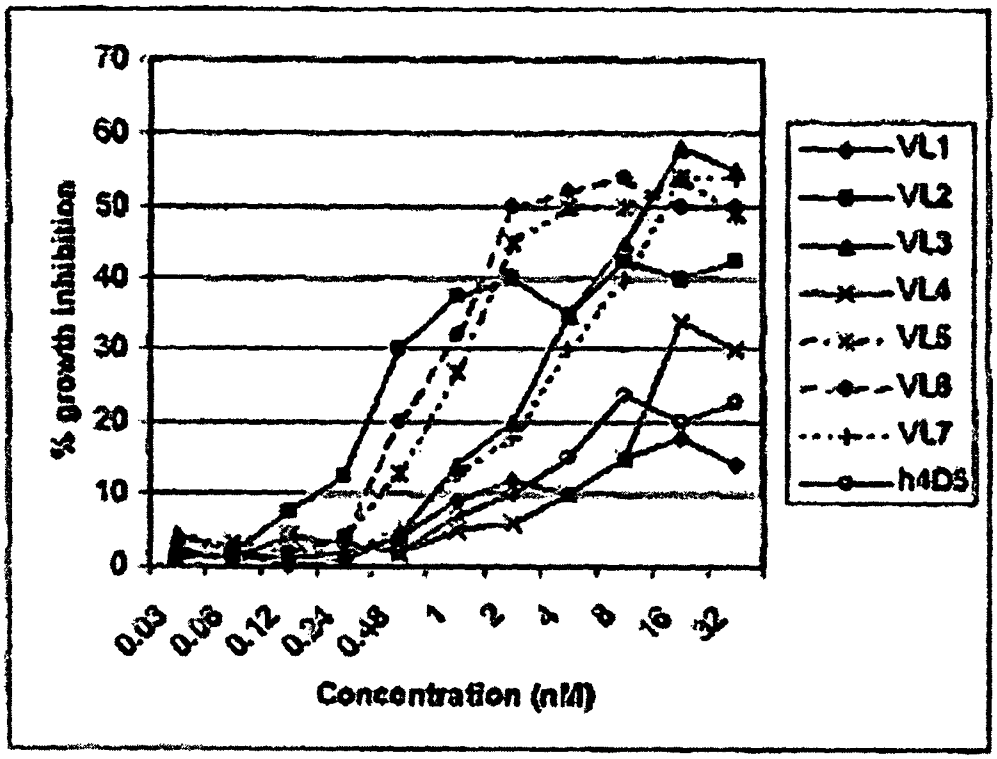
FIG. 25: Growth inhibition curves for h4D5 Fab and mixtures of 4D5* and 2C4* (see Example 17) that utilize different light chains, indicated with VL1 to VL7. Different concentrations of these Fabs are incubated with HER2-positive cells sensitive to the growth inhibitory effect of HER2-targeting antibodies.

The biological activity of the Fab mixtures is compared with that of the individual monoclonal Fab fragments. The growth inhibitory characteristics are evaluated using the breast cancer cell line, SK-BR-3 (see Hudziak et al., 1989, *Mol. Cell. Biol.* 9:1165-1172), using the assay conditions described on page 50 of WO 0100245A2. An exemplary graph in FIG. 25 shows the growth inhibition curves for h4D5 Fab and mixtures of 4D5* and 2C4* (see Example 17) that utilize different pairing-compatible light chains, indicated with VL1 to VL7. The Fabs are further evaluated for their ability to inhibit HRG-stimulated tyrosine phosphorylation of proteins in the Mr 180,000 range from whole-cell lysates of MCR7 cells, which are known to express all known ErbB receptors (as in WO 0100245A2, page 50-51). As a control, 2C4 as Fab is used; this antibody is very effective in disrupting the formation of the high affinity HER2/HER3 binding site on MCF7 cells.

Once the activity of the Fabs in the mixture confirmed, the selected, pairing-compatible VL of 3-8E3, is used to build an Oligoclonics™ of the IgG format, essentially as described in the previous Example 10. This results in the production of 30 cell clones each producing a mixture of the bivalent h4D5* and 2C4* antibodies, and the bispecific combination; the IgGs are purified from the cell supernatants by protein A column chromatography as described above, and the concentration of the total IgG present in the mixtures determined. The biological activity of the resulting IgG-mixtures is tested as in Nahta et al., *Cancer Research* 64:2343-2346 (2004), using a growth inhibition assay of BT474 breast cancer cells as described on page 2343 of this paper. Briefly BT474 cells are treated in triplicate with two-fold serial dilutions of the IgG mixtures in the range of 0.1 to 25 ng/ml. After five days, cells are trypsinized and counted by trypan blue exclusion. The growth inhibition is calculated as the fraction of viable cells compared with untreated cultures. As controls, the original antibodies hu4D5-v8 (trastuzumab) and 2C4 (Pertuzumab) are used, as well as a 1:1 mixture of these monoclonal antibodies. The mixture with the most synergic activity between the two binding sites is identified based on the dose-effect plots as described in the legend of FIG. 1 on page 2344 in Nahta et al., 2004, supra. Other tests to confirm the synergistic activity are described in this paper (in vitro tests: apoptosis induction, Akt signaling), in WO 0100245A2 (in vitro tests and in vivo tests, such as human tumor xenograft models described in Examples 5 to 7 and in FIGS. 10 to 13) and in Franklin et al., 2004, supra (in vitro HER2/HER3 heterodimerization using COS7 transfected cells).

Other examples of antibodies that can be combined with one or both of these anti-ErbB2 antibodies are antibodies with pairing-compatible chains that function as an anti-angiogenic agent (e.g., an anti-VEGF antibody); target the EGF-receptor (or ErbB1; e.g., C225 or ZD1839); or that are anti-ErbB2 antibody that strongly induce apoptosis, such as 7C2 or 7F3 (WO 0100245A2). Pairing-compatible light chains are identified using the methods described in this invention.

Example 18

Pairing-Compatible Antibodies to Produce a Mixture of Hepatocyte Growth Factor/Scatter factor (HGF/SF)-Targeting Antibodies that Block Multiple Biological Activities HGF/SF is a ligand that binds to the Met receptor tyrosine kinase. HGF/SF is composed of an α chain containing the N-terminal domain and four kringle domains covalently disulfide linked to the β chain. Binding of HGF/SF to the Met receptor tyrosine kinase induces multiple biological activities, including cell proliferation and cell invasion, and outgrowth of blood vessels (angiogenesis). In addition, binding of HGF/SF to Met prevents programmed cell death (reviewed in C. Birchmeier et. al. *Nat. Rev. Mol. Cell Biol.* 4:915-925 (2004). The Met receptor is expressed by many solid tumors and Met-HGF/SF signaling has been shown to be involved in tumor development, invasion and metastasis (J. M. Cherrington et al., *Adv. Cancer. Res.* 79:1-38 (2000); S. Rong et. al., *Mol. Cell Biol.* 12, 5152-5158 (1992).

Monoclonal antibodies against HGF/SF have been produced to study their capacity to block the diverse biological activities of HGF/SC (B. Cao et al., *Proc. Natl. Acad. Sci. U.S.A.*, 98, 7443-7448 2001). The antibodies were produced by immunizing mice with human HGF/SF and generating hybridomas secreting monoclonal antibodies. The polyclonal serum from mice immunized with HGF/SC showed potent neutralizing activity of all biologic activities of HGF/SF. In contrast a large panel of monoclonal antibodies that bind to the human HGF/SCF was shown to lack the capacity to completely block all biological activities of HGF/SC (B. Cao et al., *Proc. Natl. Acad. Sci. USA,* 98, 7443-7448 2001). Combinations of two anti-HGF/SF monoclonal antibodies still lacked full blocking activity while several mixtures of three monoclonal antibodies potently neutralized all HGF/SF activity in in vitro assays. It was concluded that blocking of the biological activities of HGF/SF requires the simultaneous binding of multiple monoclonal antibodies against different epitopes of the HGF/SF ligand (B. Cao et. al., *Proc. Natl. Acad. Sci. USA,* 98, 7443-7448 2001).

Mixtures of monoclonal antibodies directed against the same target molecule that block the complete spectrum of biological activities of the molecule are very valuable contributions to the therapeutic arsenal, especially when such blocking activities can not be achieved with monoclonal antibodies. Production of such multiple antibodies in a pharmaceutical manner and in a commercially viable way will become very important. In this example, we describe how mixtures of monoclonal antibodies against the HGF/SF ligand are isolated and used to construct an Oligoclonics™ that efficiently blocks all biological activities of this ligand.

Phage antibody scFv or Fab libraries that are formed by focusing the diversity in one variable region and keeping the other variable region invariable, preferably a germ line sequence, are particularly relevant to the invention. From such libraries it is feasible to isolate antibodies with a different heavy chain yet identical light chain, or vice versa (FIG. 3). Such antibodies are readily reformatted into an Oligoclonics™ format according to the invention. In the art, it has been described that antibodies that share the same VL gene but have different VH genes and widely varying specificities can be obtained from phage antibody display libraries (Nissim et al. (1994), *EMBO J.* 13:692-698). A sub-library of the semi-synthetic scFv library (de Kruif et al. (1995) *J. Mol. Biol.* 248:97) described in Example 7 is used to select antibodies against recombinant human HGF/SF.

The HGF/SF ligand is produced and purified from S-114 cells (NIH 3T3 cells transformed with human HGF/SF and Met) as described (S. Rong et al. (1993) *Cell Growth Differ.* 4, 563-569). For phage selections, 96-well plates are coated with 2.5 μg/ml HGF/SF in coating buffer (0.2 M $Na_2CO_3$/$NaHCO_3$, pH 9.6; 50 μl per well) overnight at 4° C. The plates were then blocked with PBS containing 1% BSA (200 μl/well) overnight at 4° C. Selections of phages binding to human HGF/SF are performed as described in the previous examples. The binding of phages selected from the library is monitored by a HGF/SF ELISA using 96-well plates coated with 2.5 μg/ml HGF/SF in coating buffer (0.2 M $Na_2CO_3$/$NaHCO_3$, pH 9.6; 50 μl per well) overnight at 4° C. The plates are then blocked with PBS containing 1% BSA (200 μl/well) overnight at 4° C.

The VH regions from individual monoclonal antibodies and the single VL region are cloned into the eukaryotic expression vector for human monoclonal antibodies as described in Example 10 and subsequently introduced into eukaryotic CHO cells by transfection. For each transfection, the plasmids encoding two or more different VH regions are mixed in various ratios and used at a concentration of 1 to 10 μg/ml. Clones secreting human antibodies are generated essentially as described in Example 10 and the supernatants monitored for HGF/SF-specific antibodies with an ELISA in 96-well plates coated with HGF/SF as described in the previous paragraph. Supernatants from clones secreting anti-HGF/SF antibodies are used to determine the capacity of mixtures to block the biological activities of HGF/SF.

Supernatants from transfectants are screened for neutralizing HGF/SF capacity in the Madin-Darby canine kidney (MDCK) scatter assay as described (B. Cao et. al., *Proc. Natl. Acad. Sci. USA,* 98, 7443-7448 2001). MDCK cells are plated at $7.5\times10^4$ cells per 100 μl per well with or without HGF (5 μg/well) in DMEM with 5% FBS. Three hundred microliters of supernatants at two-fold serial dilutions is then added to 96-well plates. A rabbit polyclonal-neutralizing antiserum (1 μl/well; ref S. Koochekpour et. al. (1997) *Cancer Res.* 57, 5391-5398) is included as control. Following overnight incubation at 37° C., cells are then stained with 0.5% crystal violet in 50% ethanol (vol/vol) for ten minutes at room temperature, and scattering is viewed using a light microscope.

Supernatants from transfectants are also screened for neutralizing HGF/SF capacity in the Branching Morphogenesis Assay as described. Branching morphogenesis assay using SK-LMS-1 cells was conducted as described (M. Jeffers et al. (1996) *Mol. Cell Biol.* 16, 1115-1125). Briefly, cell suspensions are mixed with an equal volume of GFR-Matrigel (Becton Dickinson), plated at $5\times10^4$ cells per 125 μl per well in a 96-well culture plate, and incubated for 30 minutes at 37° C. HGF/SF, with or without neutralizing mAbs, is added along with DMEM containing 10% FBS on top of the gel. After 72 to 96 hours of incubation at 37° C., representative wells are photographed at ×400 magnification.

Example 19

Pairing-Compatible Antibodies to Produce a Mixture of Antibodies that Block Vascular Endothelial Cell Growth Factor Receptor 1 (VEGF-R1) and VEGF-R2

Vascular endothelial growth factor (VEGF) is a key regulator of angiogenic processes during adult life such as wound healing, diabetic retinopathy, rheumatoid arthritis, psoriasis, inflammatory disorders and tumor growth and metastasis (N. Ferrara et. al., *Curr Top. Microbiol. Immunol.* 237-1-30 (1999); M. Klagsbrun et al., *Cytokine Rev.* 7, 259-270 (1996); G. Neufeld et al. *FASEB J.* 13, 9-22 (1999)). VEGF binds to and mediates its activity mainly through two tyrosine kinase receptors, VEGF-R1 (also named Flt-1) and VEGF-R-2 (also named KDR). Numerous studies have shown that overexpression of VEGF and its receptors plays a role in associated-associated angiogenesis and hence in tumor growth and metastasis (J. Folkman, *J. Nat. Med.* 1, 27-31 (1995); Z. Zhu et. al., *Invest. New Drugs* 17, 195-212 (1999)).

A human anti-VEGF monoclonal antibody binding to VEGF and blocking its binding to the VEGF-R1 has recently been approved by the FDA for the treatment of patients with metastatic colorectal cancer (http://www.fda.gov/cder/foi/appletter/2004/125085ltr.pdf). This shows that monoclonal antibodies that block angiogenesis provide an important tool in the treatment of solid tumors.

In WO/04003211A1, Zhu describes bispecific antibodies with one part of the molecule blocking the binding of VEGF to VEGF-R1 and another part of the molecule blocking binding of VEGF to VEGF-R2. In addition, the bi-specific antibody prevents the homodimerization of the VEGF receptors and thus blocking VEGF-R-mediated cellular signaling. Compared to binding to a single VEGF-R, dual binding can result in more potent inhibition of VEGF-stimulated cellular functions such as, for example, proliferation of endothelial cells. The bispecific antibodies described by Zhu comprise single chain Fv antibody fragments fused to the heavy and light chain constant regions of an IgG molecule. Because of the nature of the bispecific molecules, they can be expected to be immunogenic upon injection in humans, impeding their clinical effectiveness. Mixtures of human antibodies as represented in the Oligoclonics™ format that block both the VEGF-R1 and VEGR-R2 while retaining optimal clinical efficacy may be an important addition to the arsenal of anti-solid tumor drugs. Such an Oligoclonics™ is obtained as follows:

The soluble fusion protein VEGF-R2 fused to alkaline phosphatase (VEGF-R2-AP) is expressed in stably-transfected NIH 3T3 cells and purified from cell culture supernatant by affinity chromatography as described (D. Lu et al., *J. Biol. Chem.* 275, 14321-14330 (2000)). VEGF-R1-Fc fusion protein is purchased from R&D Systems (Minneapolis, Minn.). VEGF-R2-AP is coated to Maxisorp Star tubes plates at a concentration of 10 μg/ml and subsequently, the tubes are blocked with 3% milk/PBS as described in WO 003211 and D. Lu et al., *Cancer Res.* 61:7002-7008 (2001). The phage library used for selection of scFv antibody fragments specific for VEGF-R2 contains a single light chain and is diversified in the heavy chain as described in the previous Example 7. Selection of phages is carried out as described in the previous examples. The specificity of selected scFv antibody fragments is determined in ELISA with 10 μg/ml VEGF-R2-AP coated to Maxisorp 96-well plates and scFv binding, washing and detection steps as described in the previous examples. As a control for binding to the AP moiety, scFv are assayed for binding to a control AP fusion proteins such as ELF2-AP (GenHunter Corp., Nashvffle, Tn). Selection of phages binding to the VEGF-R1 is carried out by coating Maxisorp Star tubes with 10 μg/ml VEGF-R1-Fc and performing rounds of selection as described in the previous examples. The specificity of selected scFv is analyzed in ELISA with 10 μg/ml VEGF-R1-Fc coated to 96-well plates. As a control for binding to the Fc portion VEGF-R1-Fc, plates are coated with the Fc fusion protein rhsThy-1:Fc (product number ALX-203-004, Alexis Biochemicals, Lausen, Switzerland).

The VH regions from individual monoclonal antibody fragments and the single VL region are cloned into the eukaryotic expression vector for human monoclonal antibodies as described in Example 10 and subsequently introduced into eukaryotic CHO cells by transfection. For each transfection, the plasmids encoding two or more different VH regions are mixed in various ratios and used at a concentration of 1 to 10 μg/ml. Clones-secreting human antibodies are generated essentially as described in Example 10 and the supernatants monitored for VEGF-R1 and VEGF-R2-specific antibodies with an ELISA in 96-well plates coated with VEGF-R1-Fc and VEGF-R2-AP as described in the previous paragraph, and using secondary antibodies that specifically bind to the human antibodies. Supernatants from clones secreting antibodies to both receptors are used to determine the biological activity of the mixtures in VEGF-R1 and VEGF-R2 blocking assays and in an anti-mitotic and leukemia migration assays.

VEGF-R1 and VEGF-R2 blocking assays are performed as described (Z. Zhu et al., *Cancer Res.* 58:3209-14 (1998); D. Lu et al., *J. Immunol. Methods,* 230:159-71 (1999). The anti-mitotic and leukemia migration assays are performed as described in WO 04003211A1. To measure whether these antibody mixtures compete with VEGF for binding to the receptors, assays are carried out that measure the level of antibody-induced inhibition of VEGF-associated effects. For example, the effect of the antibody cocktail on VEGF-induced endothelial cell proliferation is measured using a thymidine incorporation assay. Numerous in vitro and in vivo assays have been described to measure the effect of ligands interfering with the VEGF-VEGF-receptor interaction. Some suitable assays are described in Gerbert et al., *J. Biol. Chem.* 1998, 273:30336 (cell survival assay, endothelial cell apoptosis, Akt phosphorylation assay, as on page 30337); in Mendel et al., *Clin. Cancer Res.* 2000, 6:4848-4858 (s.c. xenograft model in athymic mice, surface expression of KDR, $^{125}I$ VEGF binding assay, and Flk-1 receptor kinase assay, as on pages 4849-4850). These and other suitable assays are reviewed in Auerbach et al., 2003, *Clin. Chemistry* 49(1):32-40.

What is claimed is:

1. A method for selecting a single recombinant cell that expresses a heterogeneous combination of monospecific and bispecific antibodies, or antibody fragments thereof, wherein the monospecific and bispecific antibodies, or antibody fragments thereof, are human, humanized, or deimmunized, and wherein the heterogeneous combination has specific affinity for two target epitopes, said method comprising:

carrying out a process for producing the heterogeneous combination; the process comprising providing three different variable regions consisting of two heavy chain regions and one light chain variable region in recombinant cells, wherein antigen binding parts of the variable regions originate from an antibody from a single species and wherein one variable region is able to functionally pair with more than one other variable region, and under conditions allowing for pairing of variable regions and secretion of the paired regions from the recombinant cells resulting in the production of said heterogeneous combination, and providing two target epitopes, selecting a single recombinant cell from said recombinant cells that produces a heterogeneous combination that binds the two target epitopes, and co-purifying the heterogeneous combination therefrom utilizing a shared feature of each of the monospecific and bispecific antibodies, or antibody fragments thereof.

2. The method according to claim 1, wherein said two target epitopes are associated with a disease and/or disorder.

3. The method according to claim 2, further comprising:

subjecting a heterogeneous combination to a biological assay indicative of an effect of the combination on the disease and/or disorder.

4. The method according to claim 1, wherein the one variable region able to functionally pair with more than one other variable region does not significantly contribute to the resulting binding specificity of the resulting paired regions.

5. The method according to claim 1, wherein each variable region can only pair with one other variable region.

6. The method according to claim 1, wherein two of the three variable regions are part of one single chain Fv.

7. The method according to claim 1, wherein the expression of two of the variable regions is under the direction of different control elements.

8. The method according to claim 7, wherein the different control elements lead to differential expression.

9. The method according to claim 8, wherein the differential expression is different in levels of expression and/or time of expression.

10. The method according to claim 1, wherein the combination comprises two monospecific antibodies produced in the single recombinant cell.

11. The method according to claim 1, further comprising producing an expression system comprising nucleic acid sequences encoding variable regions; said producing comprising:

synthesizing nucleic acid sequences encoding variable regions, expressing said nucleic acid sequences and allowing the expression products to pair, and selecting nucleic acid sequences encoding variable regions having desired pairing behavior, so as to produce nucleic acid sequences encoding variable regions.

12. A method for producing a heterogeneous combination of monospecific and bispecific antibodies, or antibody fragments thereof, the method comprising:

carrying out a selection method according to claim 1, and allowing the selected cell to express the heterogeneous combination of monospecific and bispecific antibodies, or antibody fragments thereof, resulting in the production of said heterogeneous combination.

13. The method according to claim 1, wherein the shared feature is an Fc region.

* * * * *

UNITED STATES PATENT AND TRADEMARK OFFICE

CERTIFICATE OF CORRECTION

PATENT NO. : 7,919,257 B2
APPLICATION NO. : 11/292414
DATED : April 5, 2011
INVENTOR(S) : Hoogenboom et al.

It is certified that error appears in the above--identified patent and that said Letters Patent is hereby corrected as shown below:

On the title page:

| | |
|---|---|
| In ITEM (56) | |
| column 2, line 43 | after "vol. 4, pp. 1-20.*" and before "Kwaks et al.," insert paragraph break so that --Kwaks et al.,-- starts on the next line |
| Page 2, In ITEM (56) | |
| column 1, line 50 | change "a multisubunit proteins," to --a multisubunit protein,-- |

In the specification:

| | |
|---|---|
| COLUMN 25, LINE 9, | change "(e.g., CH2-0H3 region)." to --(e.g., CH2-CH3 region).-- |
| COLUMN 32, LINE 55, | change "lad," to --lacI,-- |
| COLUMN 37, LINE 40, | change "about 200 by" to --about 200 bp-- |
| COLUMN 47, LINE 17, | change "of approximately 400 by" to --of approximately 400 bp-- |
| COLUMN 49, LINE 15, | change "approximately 750-800 by" to --approximately 750-800 bp-- |
| COLUMN 52, LINE 35, | change "5′ -ACC GCC TC ACC" to --5′-ACC GCC TCC ACC-- |
| COLUMN 52, LINE 41, | change "HuV11C-BACK-A.PA" to --HuV11C-BACK-APA-- |
| COLUMN 52, LINES 42, 43 | change "GAG CCG CC-3′ (SEQ ID NO: 33)" to --CAG CCG CC-3′ (SEQ ID NO:33)-- |
| COLUMN 52, LINE 45, | change "GCG CTG ACT CAG CCT-3′" to --CCG CTG ACT CAG CCT-3′-- |
| COLUMN 52, LINE 47, | change "HuCl2-FOR.ASC" to --HuCl2-FOR-ASC-- |

Signed and Sealed this
Sixth Day of January, 2015

Michelle K. Lee

Michelle K. Lee
*Deputy Director of the United States Patent and Trademark Office*

In the specification:

| | |
|---|---|
| COLUMN 55, LINE 15, | change "a 350-400 by fragment," to --a 350-400 bp fragment,-- |
| COLUMN 59, LINE 38, | change "VH-PO1 and VL-PO 1," to --VH-PO1 and VL-PO1,-- |
| COLUMN 62, LINE 19, | after "skilled in the art." and before --Amplified VH regions are cloned-- insert paragraph break so that --Amplified VH regions are cloned-- starts on a new line and is indented |
| COLUMN 63, LINE 63, | change "Pad cloning sites)," to --PacI cloning sites),-- |
| COLUMN 64, LINE 7, | change "(SEC) ID NO:45)" to --(SEQ ID NO:45)-- |
| COLUMN 65, LINES 21, 20 | change "rabies virus ~neutralizing antibody" to --rabies virus-neutralizing antibody-- |
| COLUMN 67, LINES 36, 37 | change "is it shown that" to --it is shown that-- |
| COLUMN 69, LINE 26, | change "("hurnAMD5-8";" to --("humAMD5-8";-- |
| COLUMN 72, LINES 10, 11 | change "PDB database reference 1L71," to --PDB database reference 1L7I,-- |
| COLUMN 72, LINE 53, | change "example of h4D5 and 2C5," to --example of h4D5 and 2C4,-- |
| COLUMN 75, LINE 1, | change "HVB1 library" to --HYB1 library-- |
| COLUMN 77, LINE 38, | change "proteins in the Mr 180,000 range" to --proteins in the $M_r$ 180,000 range-- |
| COLUMN 77, LINE 39, | change "MCR7 cells." to --MCF7 cells.-- |
| COLUMN 78, LINE 39, | change "activities of HGF/SC" to --activities of HGF/SF-- |
| COLUMN 78, LINE 43, | change "immunized with HGF/SC" to --immunized with HGF/SF-- |
| COLUMN 78, LINE 46, | change "the human HGF/SCF" to --the human HGF/SF-- |
| COLUMN 78, LINE 47, | change "activities of HGF/SC" to --activities of HGF/SF-- |
| COLUMN 79, LINES 49, 50 | change "HGF (5 µg/well) in DMEM" to --HGF (5 ng/well) in DMEM-- |
| COLUMN 80, LINE 48, | change "VEGF-R1 and VEGR-R2" to --VEGF-R1 and VEGF-R2-- |
| COLUMN 81, LINE 21, | change "Clones-secreting human" to --Clones secreting human-- |

SEQUENCE LISTING

```
<160> NUMBER OF SEQ ID NOS: 64

<210> SEQ ID NO 1
<211> LENGTH: 1425
<212> TYPE: DNA
<213> ORGANISM: Artificial Sequence
<220> FEATURE:
<223> OTHER INFORMATION: heavy chain nucleotide sequence of the JA
      hybridoma

<400> SEQUENCE: 1

atggagtttg ggctgagctg gctttttctt gtggctattt taaaaggtgt ccagtgtgag     60

gtgcagctgt tggagtctgg gggaggcttg gtacagcctg gggggtccct gagactctcc    120

tgtgcagcct ctggattcac ctttagcaac tatgccatga gctgggtccg ccaggctcca    180

gggaaggggc tggagtgggt ctcagctatt agtgctagtg gtcatagcac atatttggca    240

gactccgtga agggccggtt caccatctcc agagacaatt ccaagaacac gctgtatctg    300

caaatgaaca gcctgagagc cgaggacacg gccgtatatt actgtgcgaa agatcgagag    360

gttactatga tagttgtact taatggaggc tttgactact ggggccaggg aacccgggtc    420

accgtctcct ccgcctccac caagggccca tcggtcttcc ccctggcacc ctcctccaag    480

agcacctctg gggggcacagc ggccctgggc tgcctggtca aggactactt ccccgaaccg    540

gtgacggtgt cgtggaactc aggcgccctg accagcggcg tgcacacctt cccggctgtc    600

ctacagtcct caggactcta ctccctcagc agcgtggtga ccgtgccctc cagcagcttg    660

ggcacccaga cctacatctg caacgtgaat cacaagccca gcaacaccaa ggtggacaag    720

agagttgagc ccaaatcttg tgacaaaact cacacatgcc caccgtgccc agcacctgaa    780

ctcctggggg gaccgtcagt cttcctcttc cccccaaaac ccaaggacac cctcatgatc    840

tcccggaccc ctgaggtcac atgcgtggtg gtggacgtga gccacgaaga ccctgaggtc    900

aagttcaact ggtacgtgga cggcgtggag gtgcataatg ccaagacaaa gccgcgggag    960
```

-continued

```
gagcagtaca acagcacgta ccgtgtggtc agcgtcctca ccgtcctgca ccaggactgg   1020

ctgaatggca aggagtacaa gtgcaaggtc tccaacaaag ccctcccagc ccccatcgag   1080

aaaaccatct ccaaagccaa agggcagccc cgagaaccac aggtgtacac cctgccccca   1140

tcccgggagg agatgaccaa gaaccaggtc agcctgacct gcctggtcaa aggcttctat   1200

cccagcgaca tcgccgtgga gtgggagagc aatgggcagc cggagaacaa ctacaagacc   1260

acgcctcccg tgctggactc cgacggctcc ttcttcctct atagcaagct caccgtggac   1320

aagagcaggt ggcagcaggg gaacgtcttc tcatgctccg tgatgcatga ggctctgcac   1380

aaccactaca cgcagaagag cctctccctg tccccgggta aatga                    1425
```

```
<210> SEQ ID NO 2
<211> LENGTH: 705
<212> TYPE: DNA
<213> ORGANISM: Artificial Sequence
<220> FEATURE:
<223> OTHER INFORMATION: light chain nucleotide sequence of the JA
      hybridoma

<400> SEQUENCE: 2

atggaagccc cagctcagct tctcttcctc ctgctactct ggctcccaga taccaccgga     60

gaaattgtgt tgacacagtc tccagccacc ctgtctttgt ctccagggga aagagccacc    120

ctcgcctgca gggccagtca gactgctagc aggtacttag cctggtacca acagaaacct    180

ggccaggctc ccagactcct catctatgat acatccaaca gggccactgg catcccagcc    240

aggttcagtg gcagtgggtc tgggacagac ttcactctct ccatcagcag cctggagcct    300

gaagattttg cagtttatta ctgtcagcag cgtttcaact ggccgtggac gttcggccaa    360

gggaccaagg tggaattcaa acgaactgtg gctgcaccat ctgtcttcat cttcccgcca    420

tctgatgagc agttgaaatc tggaactgcc tctgttgtgt gcctgctgaa taacttctat    480

cccagagagg ccaaagtaca gtggaaggtg gataacgccc tccaatcggg taactcccag    540

gagagtgtca cagagcagga cagcaaggac agcacctaca gcctcagcag caccctgacg    600

ctgagcaaag cagactacga gaaacacaaa gtctacgcct gcgaagtcac ccatcagggc    660

ctgagctcgc ccgtcacaaa gagcttcaac aggggagagt gttag                    705
```

```
<210> SEQ ID NO 3
<211> LENGTH: 1557
<212> TYPE: DNA
<213> ORGANISM: Artificial Sequence
<220> FEATURE:
<223> OTHER INFORMATION: heavy chain nucleotide sequence of the JB.1
      hybridoma

<400> SEQUENCE: 3

atggacacac tttgctccac gctcctgctg ctgaccatcc cttcatgggt cttgtcccaa     60

attaccttga aggagactgg tcctacgctg gtgaaaccca cacagaccct cacgctgacc    120

tgcaccttct cggggttctc actcagcact agtggagtgg gtgtgggctg gatccgtcag    180

cccccaggaa aggccctgga gtgggttaca ctcatttatt gggatgatga taagcgttac    240

agtccatctc tggagaacag ggtcaccatc aggaaggaca cctccaaaaa ccaggtggct    300

cttacaatga cgaacatgga ccctttggac acaggcacat actactgtgc gcacagacaa    360

catatcagca gcttcccgtg gttcgattcc tggggccagg gaaccctggt caccgtctcc    420

tcagcttcca ccaagggccc atcggtcttc cccctggcgc cctgctccag gagcacctct    480

gggggcacag cggccctggg ctgcctggtc aaggactact tccccgagcc ggtgacggtg    540
```

-continued

```
tcgtggaact caggcgccct gaccagcggc gtgcacacct tcccggctgt cctacagtcc    600

tcaggactct actccctcag cagcgtggtg accgtgccct ccagcagctt gggcacccag    660

acctacacct gcaacgtgaa tcacaagccc agcaacacca aggtggacaa gagagttgag    720

ctcaaaaccc cacttggtga cacaactcac acatgcccac ggtgcccaga gcccaaatct    780

tgtgacacac ctcccccgtg cccacggtgc ccagagccca aatcttgtga cacacctccc    840

ccgtgcccac ggtgcccaga gcccaaatct tgtgacacac ctcccccatg cccacggtgc    900

ccagcacctg aactcctggg aggaccgtca gtcttcctct tcccccccaaa acccaaggat    960

acccttatga tttcccggac ccctgaggtc acgtgcgtgg tggtggacgt gagccacgaa   1020

gaccccgagg tccagttcaa gtggtacgtg gacggcgtgg aggtgcataa tgccaagaca   1080

aagccgcggg aggagcagtt caacagcacg ttccgtgtgg tcagcgtcct caccgtcctg   1140

caccaggact ggctgaacgg taaggagtac aagtgcaagg tctccaacaa agccctccca   1200

gcccccatcg agaaaaccat ctccaaaacc aaaggacagc cccgagaacc acaggtgtac   1260

accctgcccc catcccggga ggagatgacc aagaaccagg tcagcctgac ctgcctggtc   1320

aaaggcttct accccagcga catcgccgtg gagtgggaga gcagcgggca gccggagaac   1380

aactacaaca ccacgcctcc catgctggac tccgacggct ccttcttcct ctacagcaag   1440

ctcaccgtgg acaagagcag gtggcagcag gggaacatct tctcatgctc cgtgatgcat   1500

gaggctctgc acaaccgctt cacgcagaag agcctctccc tgtctccggg taaatga      1557
```

<210> SEQ ID NO 4
<211> LENGTH: 699
<212> TYPE: DNA
<213> ORGANISM: Artificial Sequence
<220> FEATURE:
<223> OTHER INFORMATION: light chain nucleotide sequence of the JB.1 hybridoma

<400> SEQUENCE: 4

```
atggcctgga ccgttctcct cctcggcctc ctctctcact gcacagggtc tgtgacgtcc     60

tatgtgctga ctcagccacc ctcggtgtca gtggccccag gaaagacggc caggattaac    120

tgtgggggaa acaacattga atatagaagt gtgcactggt accagcagaa gtcaggccag    180

gcccctgtag cggtcatcta tgataatagt gaccggccct cagggatccc tgagcgattc    240

tctggttcca aatctgggaa cacggccacc ctgaccatca gcagggtcga agccggggat    300

gaggccgact attactgtca ggtgtgggat attagtagtg atgtggtctt cggcggaggg    360

accaagctga ccgtcctagg tcagcccaag gctgcccccct cggtcactct gttcccgccc    420

tcctctgagg agcttcaagc caacaaggcc acactggtgt gtctcataag tgacttctac    480

ccgggagccg tgacagtggc ctggaaggca gatagcagcc ccgtcaaggc gggagtggag    540

accaccacac cctccaaaca aagcaacaac aagtacgcgg ccagcagcta tctgagcctg    600

acgcctgagc agtggaagtc ccacagaagc tacagctgcc aggtcacgca tgaagggagc    660

accgtggaga agacagtggc ccctacagaa tgttcatag                           699
```

<210> SEQ ID NO 5
<211> LENGTH: 1431
<212> TYPE: DNA
<213> ORGANISM: Artificial Sequence
<220> FEATURE:
<223> OTHER INFORMATION: heavy chain nucleotide sequence of the M57 hybridoma

<400> SEQUENCE: 5

-continued

```
atggactgga cctggaggtt cctctttgtg gtggcagcag ctacaggtgt ccagtcccag      60
gtgcagctgg tgcagtctgg ggctgaggtg aagaagcctg ggtcctcggt gaaggtctcc     120
tgcaaggctt ctggaggcac cttcaacagg tatactgtca actgggtgcg acaggcccct     180
ggacaagggc ttgagtggat gggaggcatc atccctatct ttggtacagc aaactacgca     240
cagaggttcc agggcagact caccattacc gcggacgaat ccacgagcac agcctacatg     300
gagctgagca gcctgagatc tgatgacacg gccgtgtatt tctgtgcgag agagaatctc     360
gataattcgg ggacttatta ttatttctca ggctggttcg acccctgggg ccagggaacc     420
ctggtcaccg tctcctcagc ctccaccaag ggcccatcgg tcttccccct ggcaccctcc     480
tccaagagca cctctggggg cacagcggcc ctgggctgcc tggtcaagga ctacttcccc     540
gaaccggtga cggtgtcgtg gaactcaggc gccctgacca gcggcgtgca caccttcccg     600
gctgtcctac agtcctcagg actctactcc ctcagcagcg tggtgaccgt gccctccagc     660
agcttgggca cccagaccta catctgcaac gtgaatcaca agcccagcaa caccaaggtg     720
gacaagagag ttgagcccaa atcttgtgac aaaactcaca catgcccacc gtgcccagca     780
cctgaactcc tggggggacc gtcagtcttc ctcttccccc caaaacccaa ggacaccctc     840
atgatctccc ggacccctga ggtcacatgc gtggtggtgg acgtgagcca cgaagaccct     900
gaggtcaagt tcaactggta cgtggacggc gtggaggtgc ataatgccaa gacaaagccg     960
cgggaggagc agtacaacag cacgtaccgt gtggtcagcg tcctcaccgt cctgcaccag    1020
gactggctga atggcaagga gtacaagtgc aaggtctcca acaaagccct cccagccccc    1080
atcgagaaaa ccatctccaa agccaaaggg cagccccgag aaccacaggt gtacaccctg    1140
cccccatccc gggaggagat gaccaagaac caggtcagcc tgacctgcct ggtcaaaggc    1200
ttctatccca gcgacatcgc cgtggagtgg gagagcaatg ggcagccgga gaacaactac    1260
aagaccacgc ctcccgtgct ggactccgac ggctccttct tcctctatag caagctcacc    1320
gtggacaaga gcaggtggca gcaggggaac gtcttctcat gctccgtgat gcatgaggct    1380
ctgcacaacc actacacgca gaagagcctc tccctgtccc cgggtaaatg a             1431
```

<210> SEQ ID NO 6
<211> LENGTH: 729
<212> TYPE: DNA
<213> ORGANISM: Artificial Sequence
<220> FEATURE:
<223> OTHER INFORMATION: light chain nucleotide sequence of the M57 hybridoma

<400> SEQUENCE: 6

```
atgagtgtcc ccaccatggc ctgggctctg ctcctcctca gcctcctcac tcagggcaca      60
ggatcctggg ctcagtctgc cctgactcag cctcgctcag tgtccgggtc tcctggacag     120
tcagtcacca tctcctgcac tggaaccagc agtgatattg gtggttataa ctttgtctcc     180
tggtaccaac aacacccagg caaagccccc aaactcatga tttatgatgc cactaagcgg     240
ccctcagggg tccctgatcg cttctctggc tccaagtctg gcaacacggc ctccctgacc     300
atctctgggc tccaggctga ggatgaggct gattattact gctgctcata tgcaggcgac     360
tacacccegg gcgtggtttt cggcggaggg accaagctga ccgtcctagg tcagcccaag     420
gctgccccct cggtcactct gttcccgccc tcctctgagg agcttcaagc caacaaggcc     480
acactggtgt gtctcataag tgacttctac ccgggagccg tgacagtggc ctggaaggca     540
gatagcagcc ccgtcaaggc gggagtggag accaccacac cctccaaaca aagcaacaac     600
aagtacgcgg ccagcagcta cctgagcctg acgcctgagc agtggaagtc ccacagaagc     660
```

```
tacagctgcc aggtcacgca tgaagggagc accgtggaga agacagtggc ccctacagaa    720

tgttcatag                                                            729


<210> SEQ ID NO 7
<211> LENGTH: 125
<212> TYPE: PRT
<213> ORGANISM: Artificial Sequence
<220> FEATURE:
<223> OTHER INFORMATION: heavy chain variable region amino acid sequence
      of the JA hybridoma

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly His Ser Thr Tyr Leu Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Glu Val Thr Met Ile Val Val Leu Asn Gly Gly Phe
            100                 105                 110

Asp Tyr Trp Gly Gln Gly Thr Arg Val Thr Val Ser Ser
        115                 120                 125


<210> SEQ ID NO 8
<211> LENGTH: 109
<212> TYPE: PRT
<213> ORGANISM: Artificial Sequence
<220> FEATURE:
<223> OTHER INFORMATION: light chain variable region amino acid sequence
      of the JA hybridoma

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ala Cys Arg Ala Ser Gln Thr Ala Ser Arg Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Ser Ile Ser Ser Leu Glu Pro
65                  70                  75                  80

Glu Asp Phe Ala Val Tyr Tyr Cys Gln Gln Arg Phe Asn Trp Pro Trp
                85                  90                  95

Thr Phe Gly Gln Gly Thr Lys Val Glu Phe Lys Arg Thr
            100                 105


<210> SEQ ID NO 9
<211> LENGTH: 122
<212> TYPE: PRT
<213> ORGANISM: Artificial Sequence
<220> FEATURE:
<223> OTHER INFORMATION: heavy chain variable region amino acid sequence
      of the JB.1 hybridoma
```

<400> SEQUENCE: 9

```
Gln Ile Thr Leu Lys Glu Thr Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Val Thr Leu Ile Tyr Trp Asp Asp Asp Lys Arg Tyr Ser Pro Ser
    50                  55                  60

Leu Glu Asn Arg Val Thr Ile Arg Lys Asp Thr Ser Lys Asn Gln Val
65                  70                  75                  80

Ala Leu Thr Met Thr Asn Met Asp Pro Leu Asp Thr Gly Thr Tyr Tyr
                85                  90                  95

Cys Ala His Arg Gln His Ile Ser Ser Phe Pro Trp Phe Asp Ser Trp
            100                 105                 110

Gly Gln Gly Thr Leu Val Thr Val Ser Ser
        115                 120
```

<210> SEQ ID NO 10
<211> LENGTH: 107
<212> TYPE: PRT
<213> ORGANISM: Artificial Sequence
<220> FEATURE:
<223> OTHER INFORMATION: light chain variable region amino acid sequence of the JB.1 hybridoma

<400> SEQUENCE: 10

```
Ser Tyr Val Leu Thr Gln Pro Pro Ser Val Ser Val Ala Pro Gly Lys
1               5                   10                  15

Thr Ala Arg Ile Asn Cys Gly Gly Asn Asn Ile Glu Tyr Arg Ser Val
            20                  25                  30

His Trp Tyr Gln Gln Lys Ser Gly Gln Ala Pro Val Ala Val Ile Tyr
        35                  40                  45

Asp Asn Ser Asp Arg Pro Ser Gly Ile Pro Glu Arg Phe Ser Gly Ser
    50                  55                  60

Lys Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ile Ser Ser Asp Val
                85                  90                  95

Val Phe Gly Gly Gly Thr Lys Leu Thr Val Leu
            100                 105
```

<210> SEQ ID NO 11
<211> LENGTH: 127
<212> TYPE: PRT
<213> ORGANISM: Artificial Sequence
<220> FEATURE:
<223> OTHER INFORMATION: heavy chain variable region amino acid sequence of the M57 hybridoma

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Arg Tyr
            20                  25                  30

Thr Val Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Arg Phe
```

```
    50                  55                  60

Gln Gly Arg Leu Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ala Arg Glu Asn Leu Asp Asn Ser Gly Thr Tyr Tyr Tyr Phe Ser Gly
            100                 105                 110

Trp Phe Asp Pro Trp Gly Gln Gly Thr Leu Val Thr Val Ser Ser
        115                 120                 125


<210> SEQ ID NO 12
<211> LENGTH: 112
<212> TYPE: PRT
<213> ORGANISM: Artificial Sequence
<220> FEATURE:
<223> OTHER INFORMATION: light chain variable region amino acid sequence
      of the M57 hybridoma

<400> SEQUENCE: 12

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Phe Val Ser Trp Tyr Gln Gln His Pro Gly Lys Ala Pro Lys Leu
        35                  40                  45

Met Ile Tyr Asp Ala Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Asp
                85                  90                  95

Tyr Thr Pro Gly Val Val Phe Gly Gly Gly Thr Lys Leu Thr Val Leu
            100                 105                 110


<210> SEQ ID NO 13
<211> LENGTH: 6720
<212> TYPE: DNA
<213> ORGANISM: Artificial Sequence
<220> FEATURE:
<223> OTHER INFORMATION: VHExpress with the CMV promotor

<400> SEQUENCE: 13

gtggccacca tgggatggag ctgtatcatc ctcttcttgg tagcaacagc tacaggtaag      60

gggttaacag tagcaggctt gaggtctgga catatatatg ggtgacaatg acatccactt     120

tgcctttctc tccacaggcg cgcactccca ggtccaactg caggagagcg ggtcaccgt      180

ctcctcaggt gagtcctgtc gacggatcca cccaatgccc atgagcccag acactggacg     240

ctgaacctcg cggacagtta agaacccagg ggcctctgcg ccctgggccc agctctgtcc     300

cacaccgcgg tcacatggca ccacctctct tgcagcctcc accaagggcc catcggtctt     360

ccccctggca ccctcctcca agagcacctc tgggggcaca gcggccctgg gctgcctggt     420

caaggactac ttccccgaac cggtgacggt gtcgtggaac tcaggcgccc tgaccagcgg     480

cgtccacacc ttcccggctg tcctacagtc ctcaggactc tactccctca gcagcgtagt     540

gaccgtgccc tccagcagct tgggcaccca gacctacatc tgcaacgtga atcacaagcc     600

cagcaacacc aaggtggaca agaaagttgg tgagaggcca gcacagggag ggagggtgtc     660

tgctggaagc caggctcagc gctcctgcct ggacgcatcc cggctatgca gccccagtcc     720
```

-continued agggcagcaa ggcaggcccc gtctgcctct tcacccggag gcctctgccc gccccactca 780
tgctcaggga gagggtcttc tggctttttc cccaggctct gggcaggcac aggctaggtg 840
cccctaaccc aggccctgca cacaaagggg caggtgctgg gctcagacct gccaagagcc 900
atatccggga ggaccctgcc cctgacctaa gcccacccca aaggccaaac tctccactcc 960
ctcagctcgg acaccttctc tcctcccaga ttccagtaac tcccaatctt ctctctccag 1020
agcccaaatc ttgtgacaaa actcacacat gcccaccgtg cccaggtaag ccagcccagg 1080
cctcgccctc cagctcaagg cgggacaggt gccctagggt agcctgcatc cagggacagg 1140
ccccagccgg gtgctgacac gtccacctcc atctcttcct cagcacctga actcctgggg 1200
ggaccgtcag tcttcctctt ccccccaaaa cccaaggaca ccctcatgat ctcccggacc 1260
cctgaggtca catgcgtggt ggtggacgtg agccacgaag accctgaggt caagttcaac 1320
tggtacgtgg acggcgtgga ggtgcataat gccaagacaa agccgcggga ggagcagtac 1380
aacagcacgt accgtgtggt cagcgtcctc accgtcctgc accaggactg gctgaatggc 1440
aaggagtaca agtgcaaggt ctccaacaaa gccctcccag cccccatcga gaaaaccatc 1500
tccaaagcca aaggtgggac ccgtggggtg cgagggccac atggacagag gccggctcgg 1560
cccaccctct gccctgagag tgaccgctgt accaacctct gtccctacag ggcagccccg 1620
agaaccacag gtgtacaccc tgcccccatc ccgggatgag ctgaccaaga accaggtcag 1680
cctgacctgc ctggtcaaag gcttctatcc cagcgacatc gccgtggagt gggagagcaa 1740
tgggcagccg gagaacaact acaagaccac gcctcccgtg ctggactccg acggctcctt 1800
cttcctctac agcaagctca ccgtggacaa gagcaggtgg cagcagggga acgtcttctc 1860
atgctccgtg atgcatgagg ctctgcacaa ccactacacg cagaagagcc tctccttaag 1920
tccgggaaaa taatctagaa gctcgctgat cagcctcgac tgtgccttct agttgccagc 1980
catctgttgt ttgcccctcc cccgtgcctt ccttgaccct ggaaggtgcc actcccactg 2040
tcctttccta ataaaatgag gaaattgcat cgcattgtct gagtaggtgt cattctattc 2100
tggggggtgg ggtggggcag gacagcaagg gggaggattg ggaagacaat agcaggcatg 2160
ctggggatgg cccgggctct atggcttctg aggcggaaag aaccagctgg ggctctaggg 2220
ggtatcccca cgcgccctgt agcggcgcat taagcgcggc gggtgtggtg gttacgcgca 2280
gcgtgaccgc tacacttgcc agcgccctag cgcccgctcc tttcgctttc ttcccttcct 2340
ttctcgccac gttcgccggc tttccccgtc aagctctaaa tcggggcatc cctttagggt 2400
tccgatttag tgctttacgg cacctcgacc ccaaaaaact tgattagggt gatggttcac 2460
gtagtgggcc atcgccctga tagacggttt ttcgcccttt gacgttggag tccacgttct 2520
ttaatagtgg actcttgttc caaactggaa caacactcaa ccctatctcg gtctattctt 2580
ttgatttata agggattttg gggatttcgg cctattggtt aaaaaatgag ctgatttaac 2640
aaaaatttaa cgcgaattaa ttctgtggaa tgtgtgtcag ttagggtgtg gaaagtcccc 2700
aggctcccca ggcaggcaga agtatgcaaa gcatgcatct caattagtca gcaaccaggt 2760
gtggaaagtc cccaggctcc ccagcaggca gaagtatgca aagcatgcat ctcaattagt 2820
cagcaaccat agtcccgccc ctaactccgc ccatcccgcc cctaactccg cccagttccg 2880
cccattctcc gccccatggc tgactaattt tttttattta tgcagaggcc gaggccgcct 2940
ctgcctctga gctattccag aagtagtgag gaggcttttt tggaggccta ggcttttgca 3000
aaaagctccc gggaggtcca caatgattga acaagatgga ttgcacgcag gttctccggc 3060
cgcttgggtg gagaggctat tcggctatga ctgggcacaa cagacaatcg gctgctctga 3120

-continued

```
tgccgccgtg ttccggctgt cagcgcaggg gcgcccggtt ctttttgtca agaccgacct   3180
gtccggtgcc ctgaatgaac tccaggacga ggcagcgcgg ctatcgtggc tggccacgac   3240
gggcgttcct tgcgcagctg tgctcgacgt tgtcactgaa gcgggaaggg actggctgct   3300
attgggcgaa gtgccggggc aggatctcct gtcatctcac cttgctcctg ccgagaaagt   3360
atccatcatg gctgatgcaa tgcggcggct gcatacgctt gatccggcta cctgcccatt   3420
cgaccaccaa gcgaaacatc gcatcgagcg agcacgtact cggatggaag ccggtcttgt   3480
cgatcaggat gatctggacg aagagcatca ggggctcgcg ccagccgaac tgttcgccag   3540
gctcaaggcg cgtatgcccg acggcgagga tctcgtcgtg actcatggcg atgcctgctt   3600
gccgaatatc atggtggaaa atggccgctt ttctggattc atcgactgtg gccggctggg   3660
tgtggcggac cgctatcagg acatagcgtt ggctacccgt gatattgctg aagagcttgg   3720
cggcgaatgg gctgaccgct tcctcgtgct ttacggtatc gccgctcccg attcgcagcg   3780
catcgccttc tatcgccttc ttgacgagtt cttctgagcg ggactctggg gttcgaaatg   3840
accgaccaag cgacgcccaa cctgccatca cgagatttcg attccaccgc cgccttctat   3900
gaaaggttgg gcttcggaat cgttttccgg gacgccggct ggatgatcct ccagcgcggg   3960
gatctcatgc tggagttctt cgcccacccc aacttgttta ttgcagctta taatggttac   4020
aaataaagca atagcatcac aaatttcaca aataaagcat ttttttcact gcattctagt   4080
tgtggtttgt ccaaactcat caatgtatct tatcatgtct gtataccgga tctttccgct   4140
tcctcgctca ctgactcgct gcgctcggtc gttcggctgc ggcgagcggt atcagctcac   4200
tcaaaggcgg taatacggtt atccacagaa tcaggggata acgcaggaaa gaacatgtga   4260
gcaaaaggcc agcaaaaggc caggaaccgt aaaaaggccg cgttgctggc gtttttccat   4320
aggctccgcc cccctgacga gcatcacaaa aatcgacgct caagtcagag gtggcgaaac   4380
ccgacaggac tataaagata ccaggcgttt ccccctggaa gctccctcgt gcgctctcct   4440
gttccgaccc tgccgcttac cggatacctg tccgcctttc tcccttcggg aagcgtggcg   4500
ctttctcaat gctcacgctg taggtatctc agttcggtgt aggtcgttcg ctccaagctg   4560
ggctgtgtgc acgaaccccc cgttcagccc gaccgctgcg ccttatccgg taactatcgt   4620
cttgagtcca acccggtaag acacgactta tcgccactgg cagcagccac tggtaacagg   4680
attagcagag cgaggtatgt aggcggtgct acagagttct tgaagtggtg gcctaactac   4740
ggctacacta gaaggacagt atttggtatc tgcgctctgc tgaagccagt taccttcgga   4800
aaaagagttg gtagctcttg atccggcaaa caaaccaccg ctggtagcgg tggttttttt   4860
gtttgcaagc agcagattac gcgcagaaaa aaaggatctc aagaagatcc tttgatcttt   4920
tctacggggt ctgacgctca gtggaacgaa aactcacgtt aagggatttt ggtcatgaga   4980
ttatcaaaaa ggatcttcac ctagatcctt ttaaattaaa aatgaagttt taaatcaatc   5040
taaagtatat atgagtaaac ttggtctgac agttaccaat gcttaatcag tgaggcacct   5100
atctcagcga tctgtctatt tcgttcatcc atagttgcct gactccccgt cgtgtagata   5160
actacgatac gggagggctt accatctggc cccagtgctg caatgatacc gcgagaccca   5220
cgctcaccgg ctccagattt atcagcaata aaccagccag ccggaagggc cgagcgcaga   5280
agtggtcctg caactttatc cgcctccatc cagtctatta attgttgccg ggaagctaga   5340
gtaagtagtt cgccagttaa tagtttgcgc aacgttgttg ccattgctac aggcatcgtg   5400
gtgtcacgct cgtcgtttgg tatggcttca ttcagctccg gttcccaacg atcaaggcga   5460
gttacatgat cccccatgtt gtgcaaaaaa gcggttagct ccttcggtcc tccgatcgtt   5520
```

```
gtcagaagta agttggccgc agtgttatca ctcatggtta tggcagcact gcataattct   5580

cttactgtca tgccatccgt aagatgcttt tctgtgactg gtgagtactc aaccaagtca   5640

ttctgagaat agtgtatgcg gcgaccgagt tgctcttgcc cggcgtcaat acgggataat   5700

accgcgccac atagcagaac tttaaaagtg ctcatcattg gaaaacgttc ttcggggcga   5760

aaactctcaa ggatcttacc gctgttgaga tccagttcga tgtaacccac tcgtgcaccc   5820

aactgatctt cagcatcttt tactttcacc agcgtttctg ggtgagcaaa aacaggaagg   5880

caaaatgccg caaaaaaggg aataagggcg acacggaaat gttgaatact catactcttc   5940

ctttttcaat attattgaag catttatcag ggttattgtc tcatgagcgg atacatattt   6000

gaatgtattt agaaaaataa acaaataggg gttccgcgca catttccccg aaaagtgcca   6060

cctgacgtca gatcgacgga tcgggagatc aggtaccgaa ttcacattga ttattgagta   6120

gttattaata gtaatcaatt acggggtcat tagttcatag cccatatatg gagttccgcg   6180

ttacataact tacggtaaat ggcccgcctg gctgaccgcc caacgacccc cgcccattga   6240

cgtcaataat gacgtatgtt cccatagtaa cgccaatagg gactttccat tgacgtcaat   6300

gggtggacta tttacggtaa actgcccact tggcagtaca tcaagtgtat catatgccaa   6360

gtacgccccc tattgacgtc aatgacggta aatggcccgc ctggcattat gcccagtaca   6420

tgaccttatg ggactttcct acttggcagt acatctacgt gttagtcatc gctattacca   6480

tagtgatgcg gttttggcag tacatcaatg ggcgtggata gcggtttgac tcacggggat   6540

ttccaagtct ccaccccatt gacgtcaatg ggagtttgtt ttggcaccaa aatcaacggg   6600

actttccaaa atgtcgtaac aactccgccc cattgacgca aatgggcggt aggcgtgtac   6660

ggtgggaggt ctatataagc agagctttct ggctaactag agaacccact gcttactggc   6720
```

```
<210> SEQ ID NO 14
<211> LENGTH: 340
<212> TYPE: DNA
<213> ORGANISM: Artificial Sequence
<220> FEATURE:
<223> OTHER INFORMATION: VH-N, DP-47 based coding sequence

<400> SEQUENCE: 14

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaaggcggt    300

gcagtctact ggggccaggg aaccctggtc accgtctcct                          340


<210> SEQ ID NO 15
<211> LENGTH: 1031
<212> TYPE: DNA
<213> ORGANISM: Artificial Sequence
<220> FEATURE:
<223> OTHER INFORMATION: anti-repressor element 40 (accession number
      AY190756)

<400> SEQUENCE: 15

gatcaagaaa gcactccggg ctccagaagg agccttccag gccagctttg agcataagct     60

gctgatgagc agtgagtgtc ttgagtagtg ttcagggcag catgttacca ttcatgcttg    120

acttctagcc agtgtgacga gaggctggag tcaggtctct agagagttga gcagctccag    180

ccttagatct cccagtctta tgcggtgtgc ccattcgctt tgtgtctgca gtcccctggc    240
```

cacacccagt aacagttctg ggatctatgg gagtagcttc cttagtgagc tttcccttca 300
aatactttgc aaccaggtag agaagtttgg agtgaaggtt ttgttcttcg tttcttcaca 360
atatggatat gcatcttctt ttgaaaatgt taaagtaaat tacctctctt ttcagatact 420
gtcttcatgc gaacttggta tcctgtttcc atcccagcct tctataaccc agtaacatct 480
tttttgaaac cagtgggtga gaaagacacc tggtcaggaa cgcggaccac aggacaactc 540
aggctcaccc acggcatcag actaaaggca aacaaggact ctgtataaag taccggtggc 600
atgtgtatta gtggagatgc agcctgtgct ctgcagacag ggagtcacac agacactttt 660
ctataatttc ttaagtgctt tgaatgttca agtagaaagt ctaacattaa atttgattga 720
acaattgtat attcatggaa tattttggaa cggaatacca aaaaatggca atagtggttc 780
tttctggatg gaagacaaac ttttcttctt taaaataaat tttattttat atatttgagg 840
ttgaccacat gaccttaagg atacatatag acagtaaact ggttactaca gtgaagcaaa 900
ttaacatatc taccatcgta catagttaca ttttttgtg tgacaggaac agctaaaatc 960
tacgtattta acaaaactcc taaagacaat acatttttat taactatagc cctcatgatg 1020
tacattagat c 1031

<210> SEQ ID NO 16
<211> LENGTH: 748
<212> TYPE: DNA
<213> ORGANISM: Artificial Sequence
<220> FEATURE:
<223> OTHER INFORMATION: PacI-EcoRI insert containing VLCL in p2Fab-HER2

<400> SEQUENCE: 16
ttaattaaaa ttctatttca aggagacagt cataatgaaa aaattattat tcgcaattcc 60
tttagttgtt cctttctatt ctcacagtgc agatatccag atgacccagt ccccgagctc 120
cctgtccgcc tctgtgggcg atagggtcac tatcacctgc cgtgccagtc aggatgtgag 180
tactgctgta gcctggtatc aacagaaacc aggaaaagct ccgaaactac tgatttactc 240
ggcatccttc ctctaatctg gagtcccttc tcgcttctct ggatccagat ctgggacgga 300
tttcactctg accatcagca gtctgcagcc ggaagacttc gcaacttatt actgtcagca 360
attctatact actcctccca cgttcggaca gggtaccaag gtggagatca aacgtggaac 420
tgtggctgca ccatctgtct tcatcttccc gccatctgat gagcagttga aatctggaac 480
tgcctctgtt gtgtgcctgc tgaataactt ctatcccaga gaggccaaag tacagtggaa 540
ggtggataac gccctccaat cgggtaactc ccaggagagt gtcacagagc aggacagcaa 600
ggacagcacc tacagcctca gcagcaccct gacgctgagc aaagcagact acgagaaaca 660
caaagtctac gcctgcgaag tcacccatca gggcctgagt tcaccggtga caaagagctt 720
caacagggga gagtgttaat aagaattc 748

<210> SEQ ID NO 17
<211> LENGTH: 1609
<212> TYPE: DNA
<213> ORGANISM: Artificial Sequence
<220> FEATURE:
<223> OTHER INFORMATION: HindIII-NotI insert containing two VHCH1 in
p2Fab-HER2

<400> SEQUENCE: 17
aagctttgga gccttttttt tggagatttt caacatgaaa tacctattgc ctacggcagc 60
cgctggattg ttattactcg cggcccagcc ggccatggcc gaggttcagc tggtggagtc 120

```
tggcggtggc ctggtgcagc cagggggctc actccgtttg tcctgtgcag cttctggctt    180

caacattaaa gacacctata tacactgggt gcgtcaggcc ccgggtaagg gcctggaatg    240

ggttgcaagg atttatccta cgaatggtta tactagatat gccgatagcg tcaagggccg    300

tttcactata agcgcagaca catccaaaaa cacagcctac ctgcagatga acagcctgcg    360

tgctgaggac actgccgtct attattgttc tagatgggga ggggacggct tctatgctat    420

ggacgtgtgg ggtcaaggaa ccctggtcac cgtctcaagc gcctccacca agggcccatc    480

ggtcttcccc ctggcaccct cctccaagag cacctctggg ggcacagcgg ccctgggctg    540

cctggtcaag gactacttcc ccgaaccggt gacggtgtcg tggaactcag gcgccctgac    600

cagcggcgtc cacaccttcc cggctgtcct acagtcctca ggactctact ccctcagcag    660

cgtagtgacc gtgccctcca gcagcttggg cacccagacc tacatctgca acgtgaatca    720

caagcccagc aacaccaagg tggacaagaa agttgagccc aaatcttgtg cggcagcaga    780

acaaaaactc atctcagaag aggatctgaa tgacgccgca caccatcatc atcaccatta    840

ataaggcgcg ccaattctat ttcaaggaga cagtcataat gaaaaaatta ttattcgcaa    900

ttcctttagt tgttcctttc tattctcaca gtgcagaggt tcagctggtg gagtctggcg    960

gtggcctggt gcagccaggg ggctcactcc gtttgtcctg tgcagcttct ggcttcacct   1020

tcacagacta taccatggac tgggtgcgtc aggccccggg taagggcctg gaatgggttg   1080

cagacgtgaa cccaaactct gggggctcta tctacaacca gcgcttcaag ggtcgtttca   1140

ctctgagcgt agacagatcc aaaaacacac tgtacctgca gatgaacagc ctgcgtgctg   1200

aggacactgc cgtctattat tgtgctagaa acctgggacc ctctttctac ttcgattact   1260

ggggtcaagg aaccctggtc accgtctcaa gcgcctccac caagggccca tcggtcttcc   1320

ccctggcacc ctcctccaag agcacctctg ggggcacagc ggccctgggc tgcctggtca   1380

aggactactt ccccgaaccg gtgacggtgt cgtggaactc aggcgccctg accagcggcg   1440

tccacacctt cccggctgtc ctacagtcct caggactcta ctccctcagc agcgtagtga   1500

ccgtgccctc cagcagcttg ggcacccaga cctacatctg caacgtgaat cacaagccca   1560

gcaacaccaa ggtggacaag aaagttgagc ccaaatcttg tgcggccgc               1609


<210> SEQ ID NO 18
<211> LENGTH: 59
<212> TYPE: DNA
<213> ORGANISM: Artificial Sequence
<220> FEATURE:
<223> OTHER INFORMATION: primer

<400> SEQUENCE: 18

gtcctcgcaa ctgcggccca gccggccatg gcagaggtgc agctgttgga gtctggggg      59


<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19

acccgggtca ccgtctcctc c                                               21


<210> SEQ ID NO 20
<211> LENGTH: 10
<212> TYPE: PRT
<213> ORGANISM: Artificial Sequence
<220> FEATURE:
```

<223> OTHER INFORMATION: c-myc tag

<400> SEQUENCE: 20

Glu Gln Lys Leu Ile Ser Glu Glu Asp Leu
1 5 10

<210> SEQ ID NO 21
<211> LENGTH: 11
<212> TYPE: PRT
<213> ORGANISM: Artificial Sequence
<220> FEATURE:
<223> OTHER INFORMATION: VSV-tag

<400> SEQUENCE: 21

Tyr Thr Asp Ile Glu Met Asn Arg Leu Gly Lys
1 5 10

<210> SEQ ID NO 22
<211> LENGTH: 9
<212> TYPE: PRT
<213> ORGANISM: Artificial Sequence
<220> FEATURE:
<223> OTHER INFORMATION: influenza Hemagglutinin (HA)-tag

<400> SEQUENCE: 22

Tyr Pro Tyr Asp Val Pro Asp Tyr Ala
1 5

<210> SEQ ID NO 23
<211> LENGTH: 42
<212> TYPE: DNA
<213> ORGANISM: Artificial Sequence
<220> FEATURE:
<223> OTHER INFORMATION: primer

<400> SEQUENCE: 23
tatccgcgcg cactccgagg tgcagctgtt ggagtctggg gg 42

<210> SEQ ID NO 24
<211> LENGTH: 43
<212> TYPE: DNA
<213> ORGANISM: Artificial Sequence
<220> FEATURE:
<223> OTHER INFORMATION: primer

<400> SEQUENCE: 24
acccgggtca ccgtctcctc cggtgagtcc tagcgctttt cgt 43

<210> SEQ ID NO 25
<211> LENGTH: 23
<212> TYPE: DNA
<213> ORGANISM: Artificial Sequence
<220> FEATURE:
<223> OTHER INFORMATION: primer HuVl1A-BACK

<400> SEQUENCE: 25
cagtctgtgc tgactcagcc acc 23

<210> SEQ ID NO 26
<211> LENGTH: 23
<212> TYPE: DNA
<213> ORGANISM: Artificial Sequence
<220> FEATURE:
<223> OTHER INFORMATION: primer HuVl1B-BACK

<400> SEQUENCE: 26
cagtctgtgy tgacgcagcc gcc 23

<210> SEQ ID NO 27
<211> LENGTH: 23
<212> TYPE: DNA
<213> ORGANISM: Artificial Sequence
<220> FEATURE:
<223> OTHER INFORMATION: primer HuVl1C-BACK

<400> SEQUENCE: 27
cagtctgtcg tgacgcagcc gcc 23

<210> SEQ ID NO 28
<211> LENGTH: 21
<212> TYPE: DNA
<213> ORGANISM: Artificial Sequence
<220> FEATURE:
<223> OTHER INFORMATION: primer HuVl2-BACK

<400> SEQUENCE: 28
cartctgccc tgactcagcc t 21

<210> SEQ ID NO 29
<211> LENGTH: 23
<212> TYPE: DNA
<213> ORGANISM: Artificial Sequence
<220> FEATURE:
<223> OTHER INFORMATION: primer HuCl2-FOR

<400> SEQUENCE: 29
tgaacattct gtaggggcca ctg 23

<210> SEQ ID NO 30
<211> LENGTH: 23
<212> TYPE: DNA
<213> ORGANISM: Artificial Sequence
<220> FEATURE:
<223> OTHER INFORMATION: primer HuCL7-FOR

<400> SEQUENCE: 30
agagcattct gcaggggcca ctg 23

<210> SEQ ID NO 31
<211> LENGTH: 41
<212> TYPE: DNA
<213> ORGANISM: Artificial Sequence
<220> FEATURE:
<223> OTHER INFORMATION: primer HuVl1A-BACK-APA

<400> SEQUENCE: 31
accgcctcca ccagtgcaca gtctgtgctg actcagccac c 41

<210> SEQ ID NO 32
<211> LENGTH: 41
<212> TYPE: DNA
<213> ORGANISM: Artificial Sequence
<220> FEATURE:
<223> OTHER INFORMATION: primer HuVl1B-BACK-APA

<400> SEQUENCE: 32
accgcctcca ccagtgcaca gtctgtgytg acgcagccgc c 41

<210> SEQ ID NO 33
<211> LENGTH: 41
<212> TYPE: DNA
<213> ORGANISM: Artificial Sequence
<220> FEATURE:
<223> OTHER INFORMATION: primer HuVl1C-BACK-APA

<400> SEQUENCE: 33
accgcctcca ccagtgcaca gtctgtcgtg acgcagccgc c 41

<210> SEQ ID NO 34
<211> LENGTH: 39
<212> TYPE: DNA
<213> ORGANISM: Artificial Sequence
<220> FEATURE:
<223> OTHER INFORMATION: primer HuVl2-BACK-APA

<400> SEQUENCE: 34
accgcctcca ccagtgcaca rtctgccctg actcagcct 39

<210> SEQ ID NO 35
<211> LENGTH: 50
<212> TYPE: DNA
<213> ORGANISM: Artificial Sequence
<220> FEATURE:
<223> OTHER INFORMATION: primer HuCl2-FOR-ASC

<400> SEQUENCE: 35
accgcctcca ccgggcgcgc cttattatga acattctgta ggggccactg 50

<210> SEQ ID NO 36
<211> LENGTH: 50
<212> TYPE: DNA
<213> ORGANISM: Artificial Sequence
<220> FEATURE:
<223> OTHER INFORMATION: primer HuCl7-FOR-ASC

<400> SEQUENCE: 36
accgcctcca ccgggcgcgc cttattaaga gcattctgca ggggccactg 50

<210> SEQ ID NO 37
<211> LENGTH: 24
<212> TYPE: DNA
<213> ORGANISM: Artificial Sequence
<220> FEATURE:
<223> OTHER INFORMATION: primer CH1FOR

<400> SEQUENCE: 37
gtccttgacc aggcagccca gggc 24

<210> SEQ ID NO 38
<211> LENGTH: 17
<212> TYPE: DNA
<213> ORGANISM: Artificial Sequence
<220> FEATURE:
<223> OTHER INFORMATION: primer M13REV

<400> SEQUENCE: 38
caggaaacag ctatgac 17

<210> SEQ ID NO 39
<211> LENGTH: 59
<212> TYPE: DNA
<213> ORGANISM: Artificial Sequence
<220> FEATURE:
<223> OTHER INFORMATION: primer

<400> SEQUENCE: 39
gtcctcgcaa ctgcggccca gccggccatg gcagaggtgc agctgttgga gtctggggg 59

<210> SEQ ID NO 40
<211> LENGTH: 104

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(104)
<223> OTHER INFORMATION: /Note="mutagenic oligonucleotide"

<400> SEQUENCE: 40
cacggccgta tattactgtg cgaaagatcg agaggttact atgatagttg tacttaatgg 60
aggctttgac tactggggcc agggaacccg ggtcaccgtc tcct 104

<210> SEQ ID NO 41
<211> LENGTH: 5
<212> TYPE: PRT
<213> ORGANISM: Artificial Sequence
<220> FEATURE:
<223> OTHER INFORMATION: part of antibody CDR3

<400> SEQUENCE: 41

Gly Gly Ala Val Tyr
1 5

<210> SEQ ID NO 42
<211> LENGTH: 34
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(34)
<223> OTHER INFORMATION: oligo incorporating restriction sites

<400> SEQUENCE: 42
gtccctagga attcgatcaa gaaagcactc cggg 34

<210> SEQ ID NO 43
<211> LENGTH: 35
<212> TYPE: DNA
<213> ORGANISM: Artificial Sequence
<220> FEATURE:
<223> OTHER INFORMATION: oligo incorporating restriction sites

<400> SEQUENCE: 43
cctcatgatg tacattagat cgaattcgta atacg 35

<210> SEQ ID NO 44
<211> LENGTH: 6
<212> TYPE: DNA
<213> ORGANISM: Artificial Sequence
<220> FEATURE:
<223> OTHER INFORMATION: restriction site

<400> SEQUENCE: 44 gaattc 6

<210> SEQ ID NO 45
<211> LENGTH: 16
<212> TYPE: DNA
<213> ORGANISM: Artificial Sequence
<220> FEATURE:
<223> OTHER INFORMATION: oligo
<220> FEATURE:
<221> NAME/KEY: misc_feature
<222> LOCATION: (1)..(16)
<223> OTHER INFORMATION: /Note="sequence appended to primer"

<400> SEQUENCE: 45
tatccgcgcg cactcc 16

<210> SEQ ID NO 46
<211> LENGTH: 168
<212> TYPE: DNA
<213> ORGANISM: Artificial Sequence
<220> FEATURE:
<223> OTHER INFORMATION: polylinker sequence of pSCFV

<400> SEQUENCE: 46
gcggcccagc cggccatggc acaggtccaa ctgcaggtca ccgtctcgag tggtggaggc 60
ggttcaggcg gaggtggctc tggcggtggc ggatcggata tcgagctcac tgagatcaaa 120
cgggcggccg cagaacaaaa actcatctca gaagaggatc tgaattaa 168

<210> SEQ ID NO 47
<211> LENGTH: 55
<212> TYPE: PRT
<213> ORGANISM: Artificial Sequence
<220> FEATURE:
<223> OTHER INFORMATION: polylinker sequence of pSCFV

<400> SEQUENCE: 47

Ala Ala Ala Pro Ala Met Ala Gln Val Gln Leu Gln Val Thr Val Ser
1 5 10 15

Ser Gly Gly Gly Gly Ser Gly Gly Gly Gly Ser Gly Gly Gly Gly Ser
20 25 30

Asp Ile Glu Leu Thr Glu Ile Lys Arg Ala Ala Ala Glu Gln Lys Leu
35 40 45

Ile Ser Glu Glu Asp Leu Asn
50 55

<210> SEQ ID NO 48
<211> LENGTH: 13
<212> TYPE: DNA
<213> ORGANISM: Artificial Sequence
<220> FEATURE:
<223> OTHER INFORMATION: enzyme site SfiI
<220> FEATURE:
<221> NAME/KEY: misc_feature
<222> LOCATION: (5)..(9)
<223> OTHER INFORMATION: "n" stands for any nucleic acid

<400> SEQUENCE: 48
ggccnnnnng gcc 13

<210> SEQ ID NO 49
<211> LENGTH: 8
<212> TYPE: DNA
<213> ORGANISM: Artificial Sequence
<220> FEATURE:
<223> OTHER INFORMATION: enzyme site NotI

<400> SEQUENCE: 49 gcggccgc 8

<210> SEQ ID NO 50
<211> LENGTH: 6
<212> TYPE: DNA
<213> ORGANISM: Artificial Sequence
<220> FEATURE:
<223> OTHER INFORMATION: enzyme site ApaII

<400> SEQUENCE: 50 gtgcac 6

<210> SEQ ID NO 51
<211> LENGTH: 6
<212> TYPE: DNA
<213> ORGANISM: Artificial Sequence
<220> FEATURE:
<223> OTHER INFORMATION: enzyme site XhoI

<400> SEQUENCE: 51 ctcgag 6

<210> SEQ ID NO 52
<211> LENGTH: 6
<212> TYPE: DNA
<213> ORGANISM: Artificial Sequence
<220> FEATURE:
<223> OTHER INFORMATION: enzyme site SacI

<400> SEQUENCE: 52 gagctc 6

<210> SEQ ID NO 53
<211> LENGTH: 6
<212> TYPE: DNA
<213> ORGANISM: Artificial Sequence
<220> FEATURE:
<223> OTHER INFORMATION: enzyme site PstI

<400> SEQUENCE: 53 ctgcag 6

<210> SEQ ID NO 54
<211> LENGTH: 6
<212> TYPE: DNA
<213> ORGANISM: Artificial Sequence
<220> FEATURE:
<223> OTHER INFORMATION: enzyme site NcoI

<400> SEQUENCE: 54 ccatgg 6

<210> SEQ ID NO 55
<211> LENGTH: 6
<212> TYPE: DNA
<213> ORGANISM: Artificial Sequence
<220> FEATURE:
<223> OTHER INFORMATION: enzyme site SalI

<400> SEQUENCE: 55 gtcgac 6

<210> SEQ ID NO 56
<211> LENGTH: 7
<212> TYPE: DNA
<213> ORGANISM: Artificial Sequence
<220> FEATURE:
<223> OTHER INFORMATION: enzyme site BstEII
<220> FEATURE:
<221> NAME/KEY: misc_feature
<222> LOCATION: (4)..(4)
<223> OTHER INFORMATION: “n” stands for any nucleic acid

<400> SEQUENCE: 56 ggtnacc 7

<210> SEQ ID NO 57

<211> LENGTH: 6
<212> TYPE: DNA
<213> ORGANISM: Artificial Sequence
<220> FEATURE:
<223> OTHER INFORMATION: enzyme site EcoRV

<400> SEQUENCE: 57 gatatc 6

<210> SEQ ID NO 58
<211> LENGTH: 355
<212> TYPE: DNA
<213> ORGANISM: Artificial Sequence
<220> FEATURE:
<223> OTHER INFORMATION: part of plasmid comprising 3 antibody-regions
<220> FEATURE:
<221> NAME/KEY: misc_feature
<222> LOCATION: (91)..(93)
<223> OTHER INFORMATION: "n" stands for unknown nucleic acid
<220> FEATURE:
<221> NAME/KEY: misc_feature
<222> LOCATION: (257)..(259)
<223> OTHER INFORMATION: "n" stands for unknown nucleic acid
<220> FEATURE:
<221> NAME/KEY: CDS
<222> LOCATION: (1)..(102)
<223> OTHER INFORMATION: part of plasmid comprising 3 antibody-regions
<220> FEATURE:
<221> NAME/KEY: CDS
<222> LOCATION: (143)..(355)
<223> OTHER INFORMATION: part of plasmid comprising 3 antibody-regions

<400> SEQUENCE: 58

```
tta ttc gca att cct tta gtt gtt cct ttc tat tct cac agt gca cag       48
Leu Phe Ala Ile Pro Leu Val Val Pro Phe Tyr Ser His Ser Ala Gln
1               5                   10                  15

gtc caa ctg cag gtc gac ctc gag atc aaa cgt gga act gtg nnn gga       96
Val Gln Leu Gln Val Asp Leu Glu Ile Lys Arg Gly Thr Val Xaa Gly
            20                  25                  30

gag tgt taataaggcg cgccaattct atttcaagga gacagtcata atg aaa tac      151
Glu Cys                                             Met Lys Tyr
                                                    35

cta ttg cct acg gca gcc gct gga ttg tta tta ctc gcg gcc cag ccg      199
Leu Leu Pro Thr Ala Ala Ala Gly Leu Leu Leu Leu Ala Ala Gln Pro
        40                  45                  50

gcc atg gcc cag gtg cag ctg cag gag agc ggg gtc acc gtc tca agc      247
Ala Met Ala Gln Val Gln Leu Gln Glu Ser Gly Val Thr Val Ser Ser
    55                  60                  65

gcc tcc acc nnn aaa tct tgt gcg gcc gca cat cat cat cat cat cac      295
Ala Ser Thr Xaa Lys Ser Cys Ala Ala Ala His His His His His His
70                  75                  80                  85

ggg gcc gca gaa caa aaa ctc atc tca gaa gag gat ctg aat ggg gcc      343
Gly Ala Ala Glu Gln Lys Leu Ile Ser Glu Glu Asp Leu Asn Gly Ala
                90                  95                  100

gca tag act gtt                                                      355
Ala     Thr Val
```

<210> SEQ ID NO 59
<211> LENGTH: 34
<212> TYPE: PRT
<213> ORGANISM: Artificial Sequence
<220> FEATURE:
<221> NAME/KEY: misc_feature
<222> LOCATION: (31)..(31)
<223> OTHER INFORMATION: The 'Xaa' at location 31 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<220> FEATURE:
<223> OTHER INFORMATION: part of plasmid comprising 3 antibody-regions

<400> SEQUENCE: 59

Leu Phe Ala Ile Pro Leu Val Val Pro Phe Tyr Ser His Ser Ala Gln
1 5 10 15

Val Gln Leu Gln Val Asp Leu Glu Ile Lys Arg Gly Thr Val Xaa Gly
20 25 30

Glu Cys

<210> SEQ ID NO 60
<211> LENGTH: 68
<212> TYPE: PRT
<213> ORGANISM: Artificial Sequence
<220> FEATURE:
<221> NAME/KEY: misc_feature
<222> LOCATION: (39)..(39)
<223> OTHER INFORMATION: The 'Xaa' at location 39 stands for Lys, Asn, Arg, Ser, Thr, Ile, Met, Glu, Asp, Gly, Ala, Val, Gln, His, Pro, Leu, a stop codon, Tyr, Trp, Cys, or Phe.
<220> FEATURE:
<223> OTHER INFORMATION: part of plasmid comprising 3 antibody-regions

<400> SEQUENCE: 60

Met Lys Tyr Leu Leu Pro Thr Ala Ala Ala Gly Leu Leu Leu Leu Ala
1 5 10 15

Ala Gln Pro Ala Met Ala Gln Val Gln Leu Gln Glu Ser Gly Val Thr
20 25 30

Val Ser Ser Ala Ser Thr Xaa Lys Ser Cys Ala Ala Ala His His His
35 40 45

His His His Gly Ala Ala Glu Gln Lys Leu Ile Ser Glu Glu Asp Leu
50 55 60

Asn Gly Ala Ala
65

<210> SEQ ID NO 61
<211> LENGTH: 108
<212> TYPE: PRT
<213> ORGANISM: Artificial Sequence
<220> FEATURE:
<223> OTHER INFORMATION: Hybrid light chain

<400> SEQUENCE: 61

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg
100 105

<210> SEQ ID NO 62
<211> LENGTH: 108
<212> TYPE: PRT
<213> ORGANISM: Artificial Sequence
<220> FEATURE:
<223> OTHER INFORMATION: Hybrid light chain

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg
            100                 105
```

<210> SEQ ID NO 63
<211> LENGTH: 108
<212> TYPE: PRT
<213> ORGANISM: Artificial Sequence
<220> FEATURE:
<223> OTHER INFORMATION: Hybrid light chain
<220> FEATURE:
<221> NAME/KEY: MISC_FEATURE
<222> LOCATION: (24)..(96)
<223> OTHER INFORMATION: "Xaa" means positions to be targeted for diversification in a library approach

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asp Val Xaa Xaa Xaa
            20                  25                  30

Val Ala Trp Tyr Gln Gln Lys Pro Gly Lys Ala Pro Lys Leu Leu Ile
        35                  40                  45

Tyr Ser Ala Ser Xaa Xaa Tyr Xaa Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Tyr Xaa Xaa Pro Xaa
                85                  90                  95

Thr Phe Gly Gln Gly Thr Lys Val Glu Ile Lys Arg
            100                 105
```

<210> SEQ ID NO 64
<211> LENGTH: 108
<212> TYPE: PRT
<213> ORGANISM: Artificial Sequence
<220> FEATURE:
<223> OTHER INFORMATION: Hybrid light chain
<220> FEATURE:
<221> NAME/KEY: MISC_FEATURE
<222> LOCATION: (53)..(56)
<223> OTHER INFORMATION: "Xaa" means positions to be targeted for diversification in a library approach

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

-continued

```
Val Ala Trp Tyr Gln Gln Lys Pro Gly Lys Ala Pro Lys Leu Leu Ile
        35                  40                  45

Tyr Ser Ala Ser Xaa Xaa Tyr Xaa Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Thr Thr Pro Pro
                85                  90                  95

Thr Phe Gly Gln Gly Thr Lys Val Glu Ile Lys Arg
            100                 105
```